United States Patent
Abraham et al.

(10) Patent No.: US 10,851,347 B2
(45) Date of Patent: Dec. 1, 2020

(54) ALTERED ADHERENT STROMAL CELLS AND METHODS OF PRODUCING AND USING SAME

(71) Applicant: PLURISTEM LTD., Haifa (IL)

(72) Inventors: Eytan Abraham, Frederick, MD (US); Lior Raviv, Kfar-Monash (IL); Maya Wadamany, Haifa (IL); Nadav Eshkol, Haifa (IL)

(73) Assignee: PLURISTEM LTD., Haifa (IL)

( * ) Notice: Subject to any disclaimer, the term of this patent is extended or adjusted under 35 U.S.C. 154(b) by 42 days.

(21) Appl. No.: 16/307,015

(22) PCT Filed: Jun. 6, 2016

(86) PCT No.: PCT/IB2016/053310
§ 371 (c)(1),
(2) Date: Dec. 4, 2018

(87) PCT Pub. No.: WO2017/212309
PCT Pub. Date: Dec. 14, 2017

(65) Prior Publication Data
US 2020/0131481 A1   Apr. 30, 2020

(51) Int. Cl.
*A61K 35/12* (2015.01)
*C12N 5/00* (2006.01)
*C12N 5/0775* (2010.01)
*A61K 35/50* (2015.01)
*C12M 1/00* (2006.01)

(52) U.S. Cl.
CPC ............ *C12N 5/0668* (2013.01); *A61K 35/12* (2013.01); *A61K 35/50* (2013.01); *C12M 21/00* (2013.01); *C12M 23/14* (2013.01); *C12N 2501/052* (2013.01); *C12N 2501/24* (2013.01); *C12N 2501/25* (2013.01); *C12N 2513/00* (2013.01); *C12N 2533/30* (2013.01)

(58) Field of Classification Search
CPC ...... A61K 35/12; A61K 2121/00; C12N 5/00; C12N 5/0607; C12N 5/0647; C12N 5/0653; C12N 2500/00; C12N 2501/00; C12N 2501/24; C12N 2501/25; C12N 2513/00; C12M 21/00
See application file for complete search history.

(56) References Cited

U.S. PATENT DOCUMENTS

2014/0017209 A1   1/2014   Aberman et al.

FOREIGN PATENT DOCUMENTS

| WO | 2007108003 | A2 |   | 9/2007 |
| WO | 2009037690 | A1 |   | 3/2009 |
| WO | 2010026573 | A1 |   | 3/2010 |
| WO | 2010026575 | A2 |   | 3/2010 |
| WO | WO 10/026575 |   | * | 3/2010 |
| WO | 2011132087 | A1 |   | 10/2011 |
| WO | 2014128634 | A1 |   | 8/2014 |
| WO | WO 14/128634 |   | * | 8/2014 |
| WO | 2015004609 | A2 |   | 1/2015 |
| WO | 2016001845 | A1 |   | 1/2016 |
| WO | 2016098061 | A1 |   | 6/2016 |

OTHER PUBLICATIONS

Donnenberg et al, Cytometry Part A (87A): 665-674, 2015; available online Apr. 30, 2015.*
Mohammadpour et al, Immunopharmacol. & Immunotoxicol. 38(2): 68-76, 2016; available online Nov. 24, 2015.*
Zimmermann et al, Cytotherapy 16: 331-345, 2014.*
Ren et al, Cell Stem Cell 11: 812-824, 2012.*
Song et al, Int. J. Biochem. & Cell Biol. 37: 2357-2365, 2005.*
Eibes et al, J. Biotechnol. 146:194-197, 2010.*
Chen et al., "The effect of conditioned medium derived from human placental multipotent mesenchymal stromal cells on neutrophils: possible implications for placental infection," Molecular Human Reproduction (2014) vol. 20, No. 11, pp. 1117-1125.
International Search Report and Written Opinion issued in PCT/IB2016/053310, dated Oct. 21, 2016.
Nielsen, "Pathogenicity and immunity studies of Haemophilus parasuis serotypes," Acta Veterinaria Scandinavica (1993) vol. 34, No. 2, pp. 193-198.
Prather et al., "The role of placental-derived adherent stromal cell (PLX-PAD) in the treatment of critical limb schemi," Cytotherapy (2009) vol. 11, No. 4, pp. 427-434.
Prather, "Company Profile: Pluristem Therapeutics, Inc." Regen Med (2008) vol. 3, No. 1, pp. 117-122.
François et al., "Human MSC Suppression Correlates With Cytokine Induction of Indoleamine 2,3-Dioxygenase and Bystander M2 Macrophage Differentiation," Molecular Therapy (2012) vol. 20, No. 1, pp. 187-195.
Jeon et al., "Comparative Analysis of Human Mesenchymal Stem Cells Derived From Bone Marrow, Placenta, and Adipose Tissue as Sources of Cell Therapy," J Cell Biochem (2016) vol. 117, pp. 1112-1125.
Kavanagh et al., "Pretreatment of Mesenchymal Stem Cells Manipulates Their Vasculoprotective Potential While Not Altering Their Homing Within the Injured Gut," Stem Cells (2015) vol. 33, pp. 2785-2797.
Li et al., "Interferon-gamma and tumor necrosis factor-alpha promote the ability of human placenta-derived mesenchymal stromal cells to express programmed death ligand-2 and induce the differentiation of CD4+interleukin-10+and CD8+interleukin-10+Treg subsets," Cytotherapy (2015) vol. 17, pp. 1560-1571.
Sivanathan et al., "Interleukin-17A-Induced Human Mesenchymal Stem Cells Are Superior Modulators of Immunological Function," Stem Cells (2015) vol. 33, pp. 2850-2863.
Strober et al., "Pro-Inflammatory Cytokines in the Pathogenesis of IBD," Gastroenterology (2011) vol. 140, No. 6, pp. 1756-1767.
Zhang et al., "Exomes originating from MSCs stimulated with TGF-beta and IFN-gamma," Journal of Cellular Physiology (2018) vol. 23, No. 9, pp. 6832-6840.

* cited by examiner

Primary Examiner — Kevin K Hill
(74) Attorney, Agent, or Firm — Lando & Anastasi, LLP

(57) ABSTRACT

Disclosed herein are altered adherent stromal cells and methods of producing and utilizing same.

21 Claims, 58 Drawing Sheets

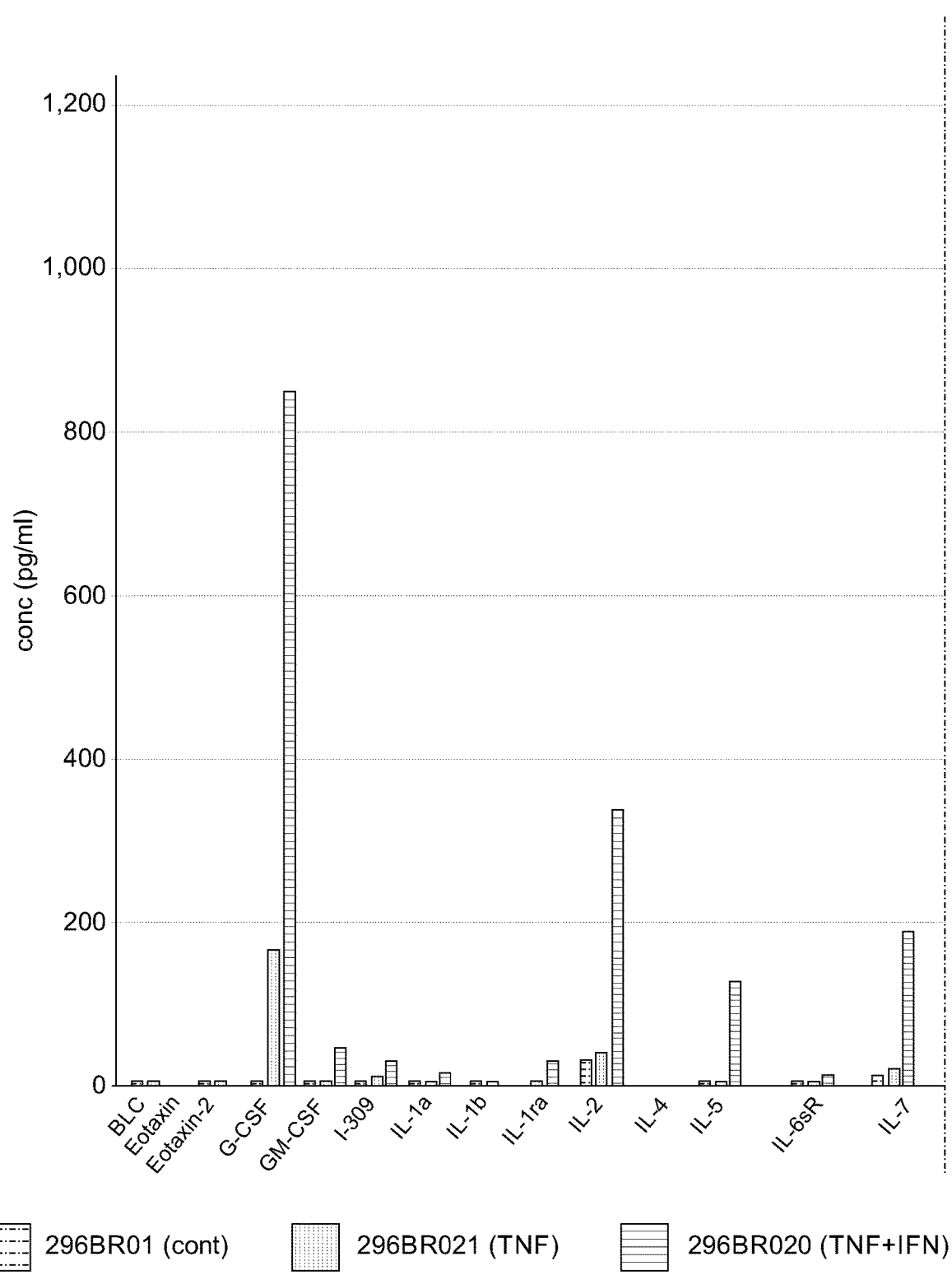
Figure 9C I

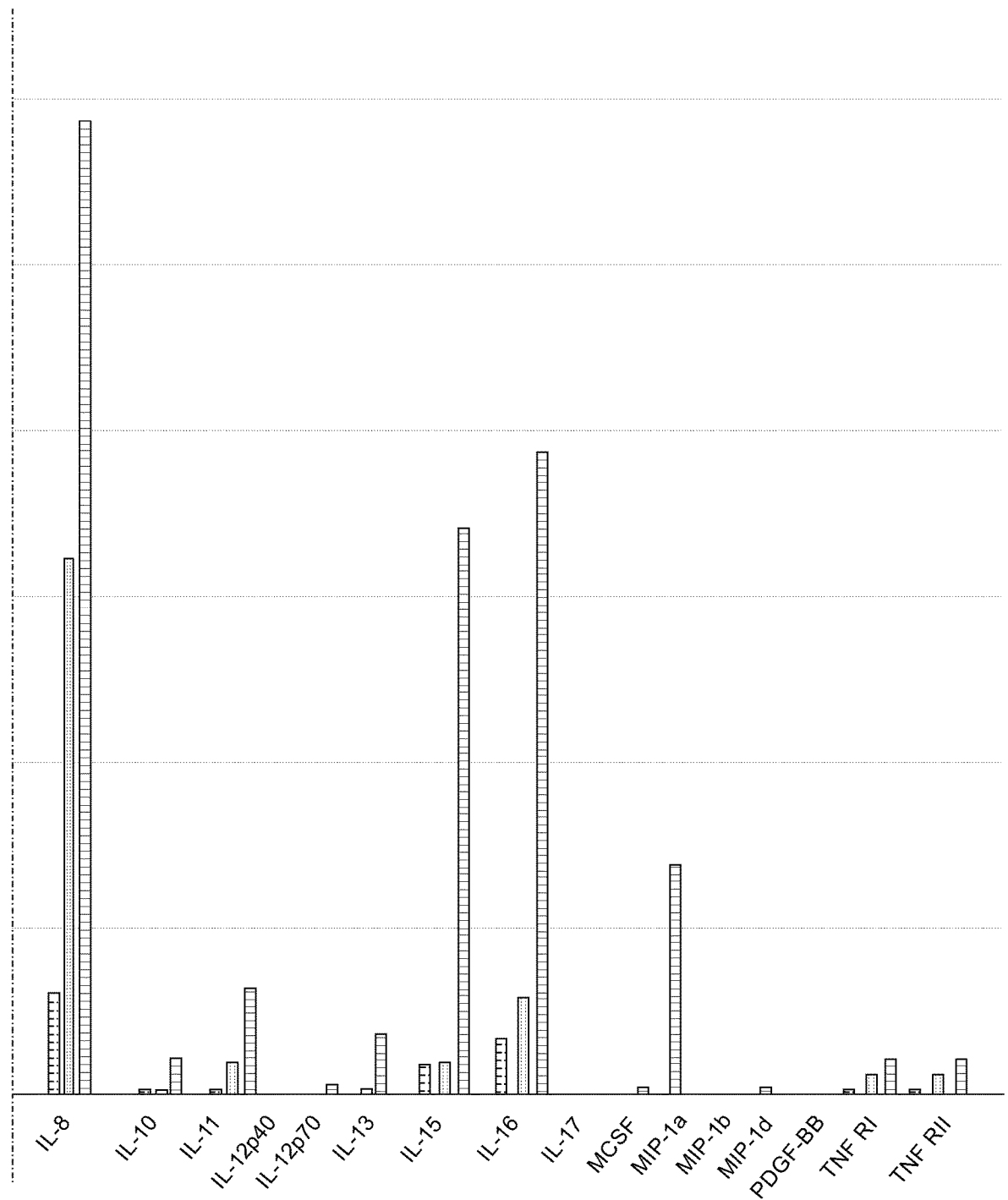
Figure 9C II

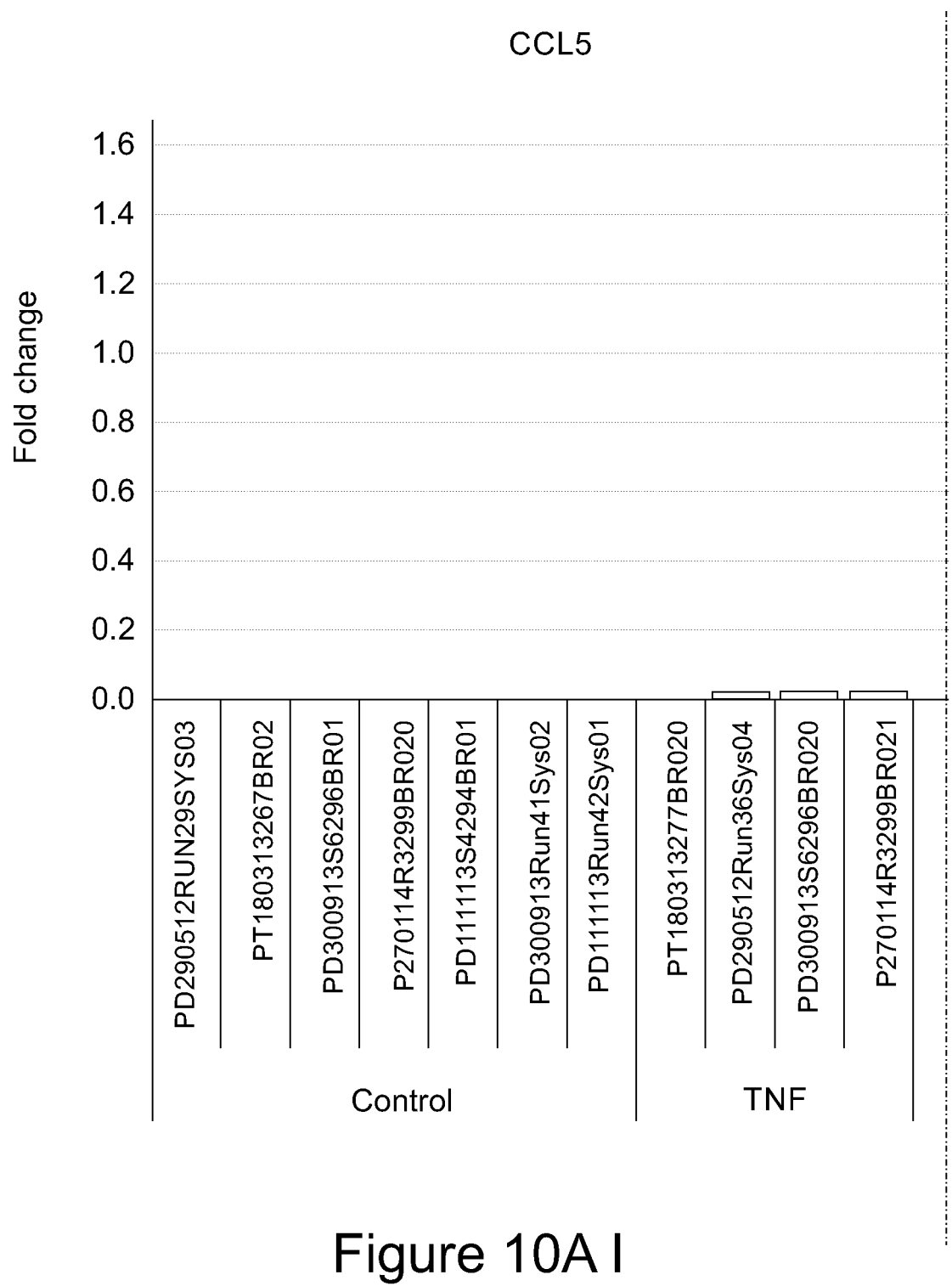
Figure 10A I

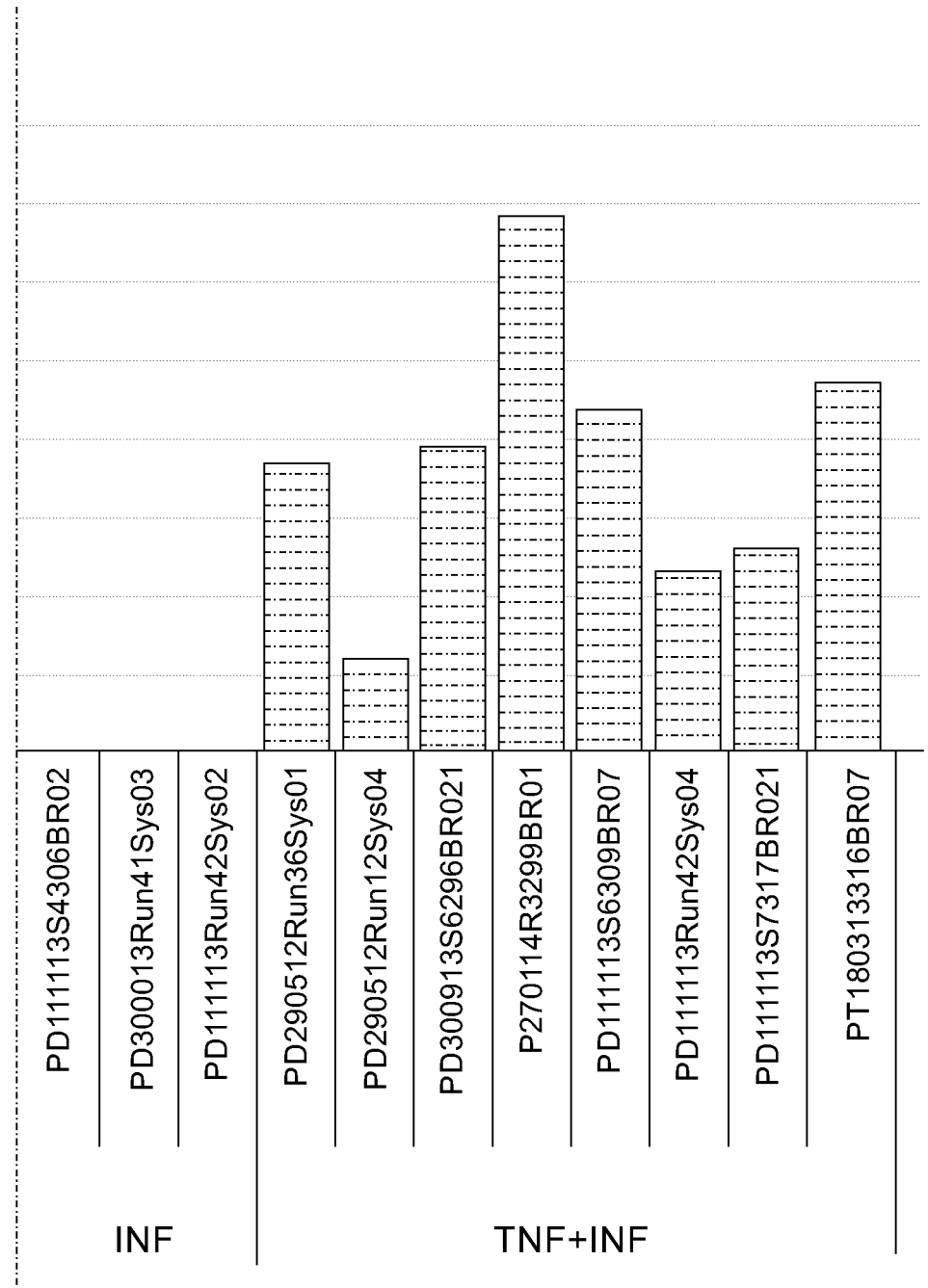
Figure 10A II

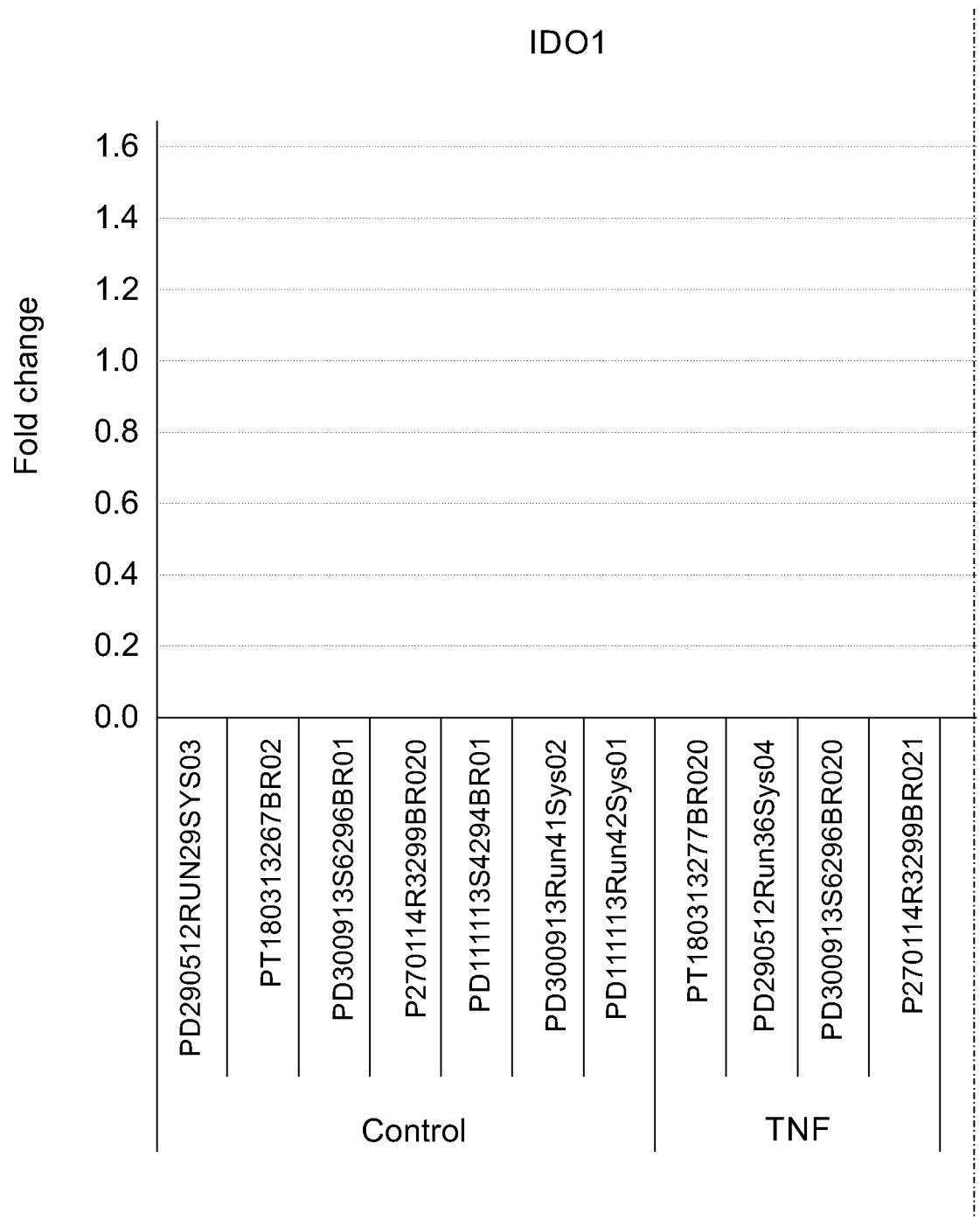
Figure 11A I

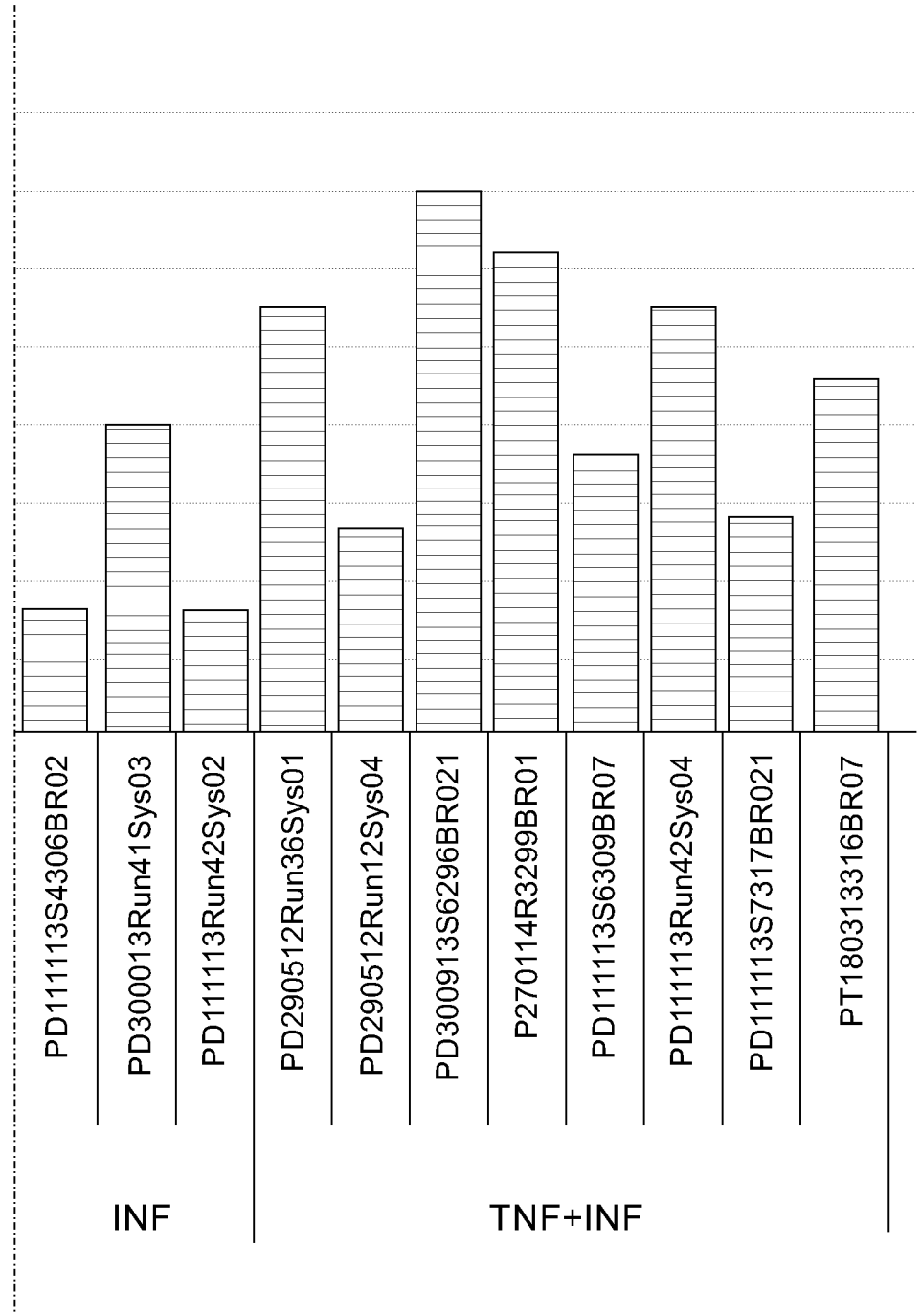
Figure 11A II

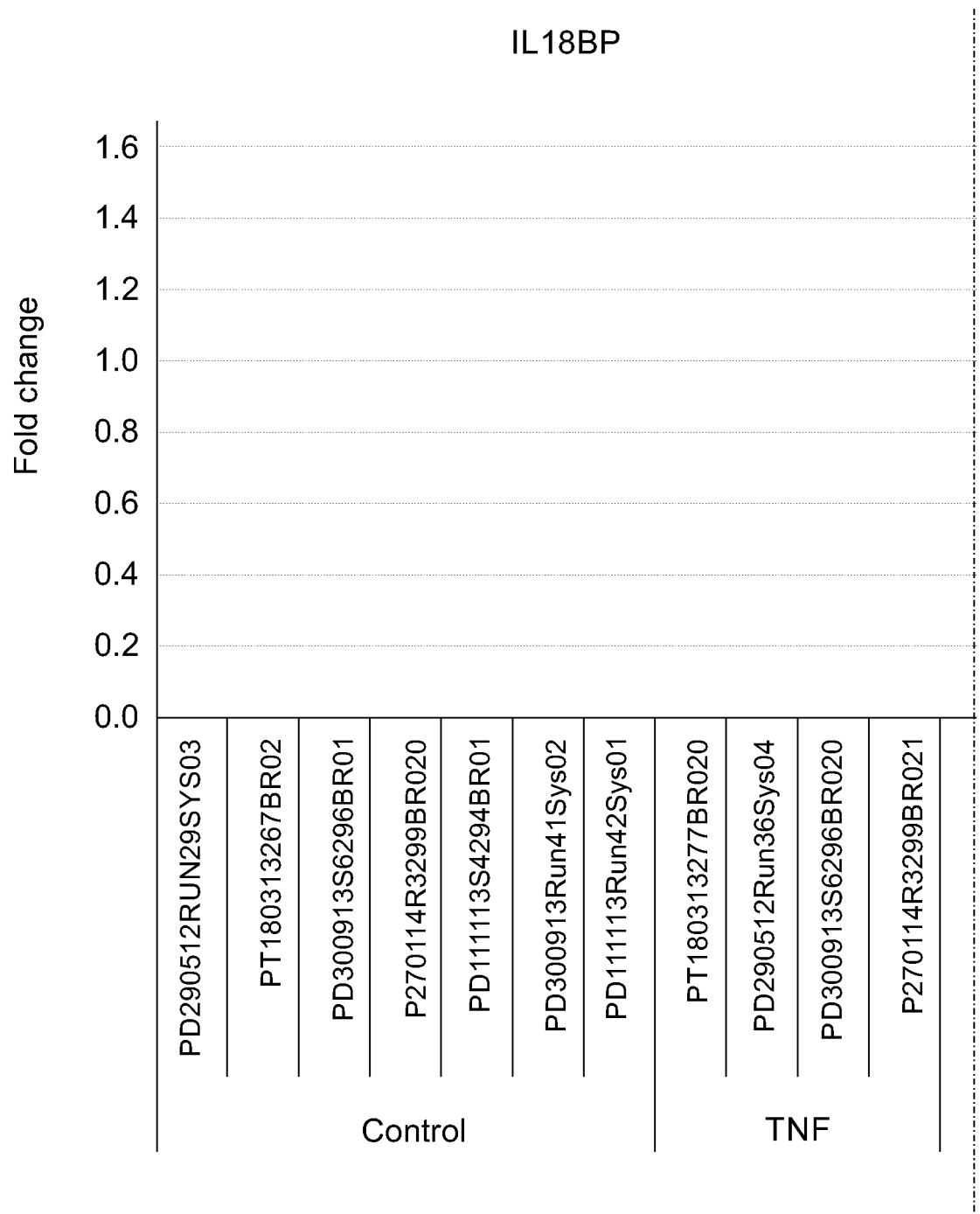
Figure 11B I

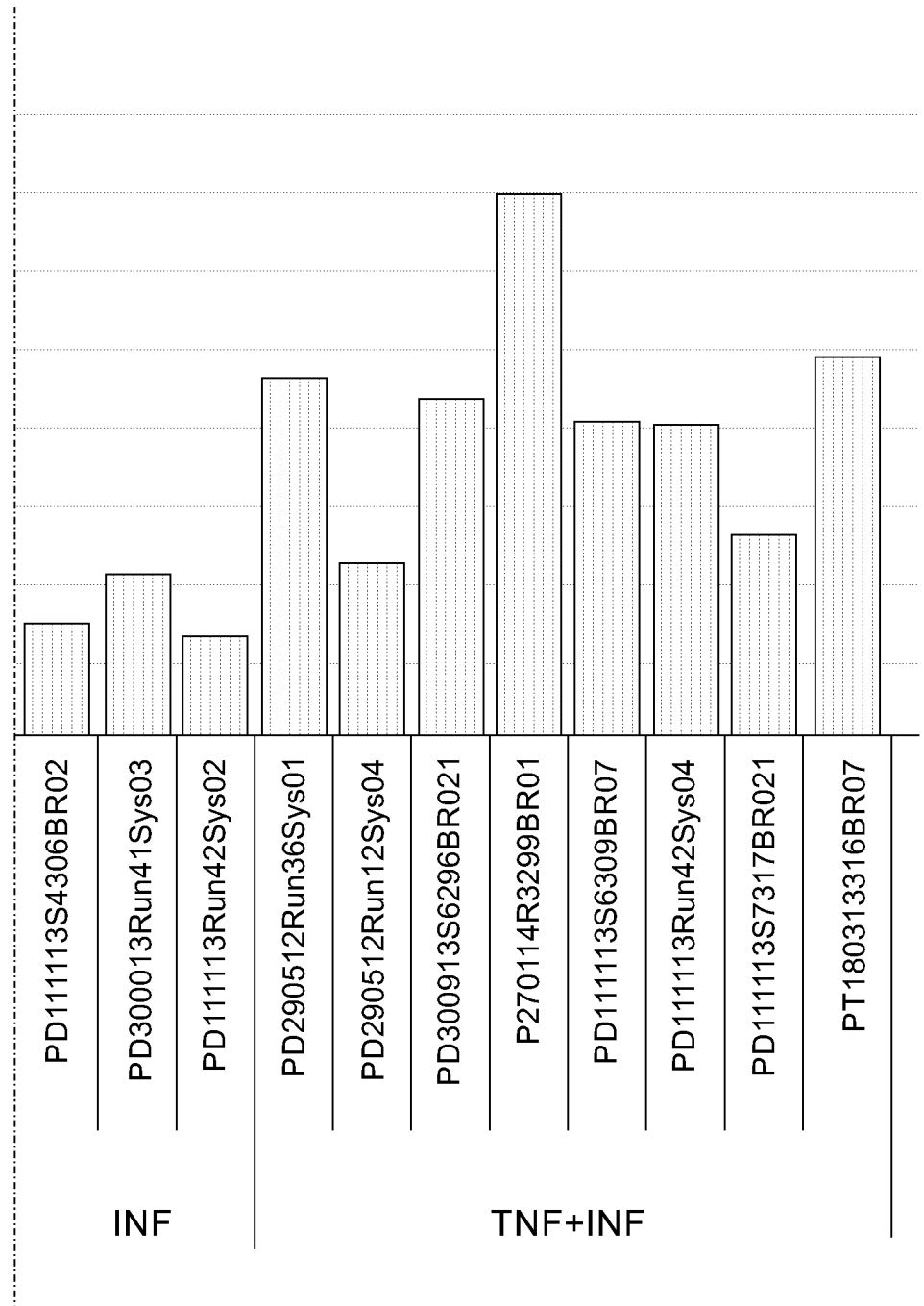
Figure 11B II

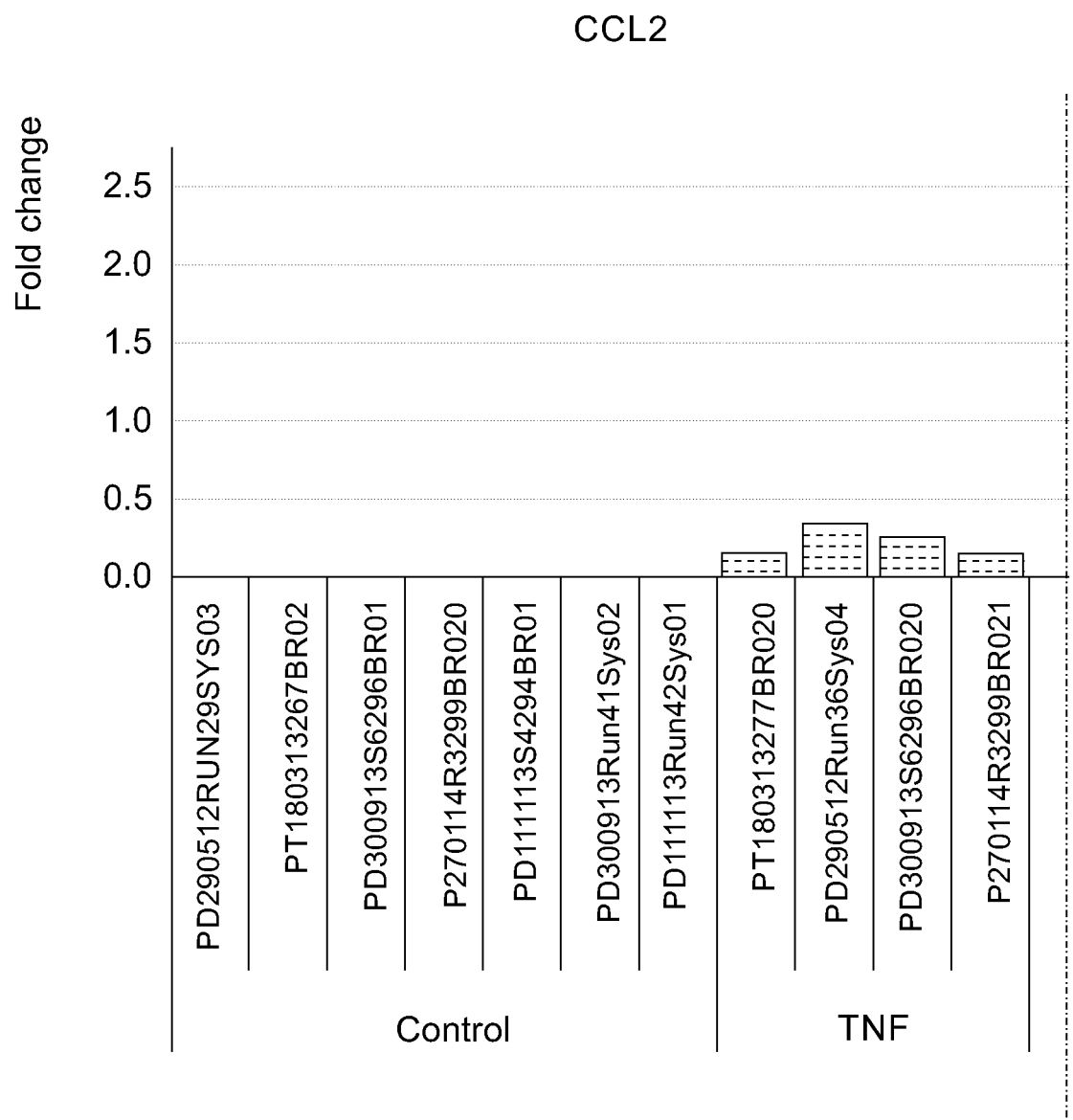
Figure 11C I

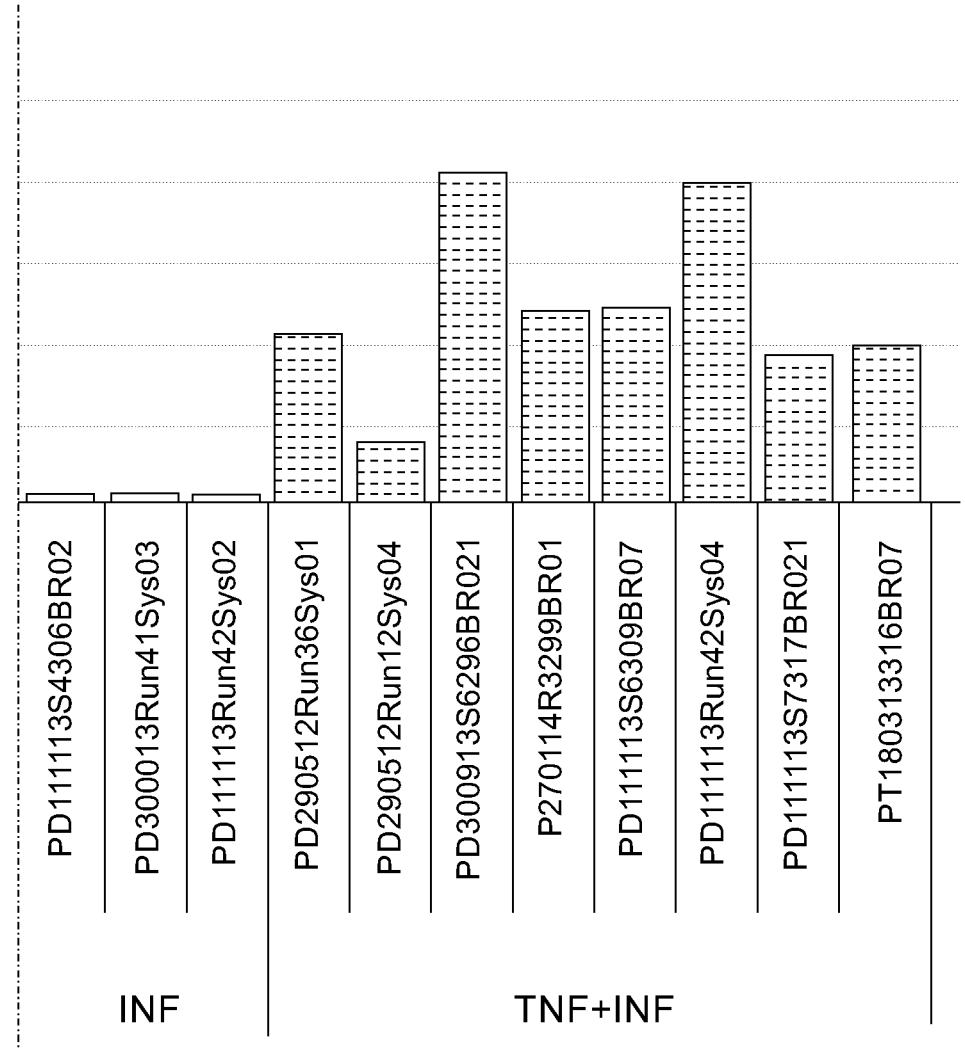
Figure 11C II

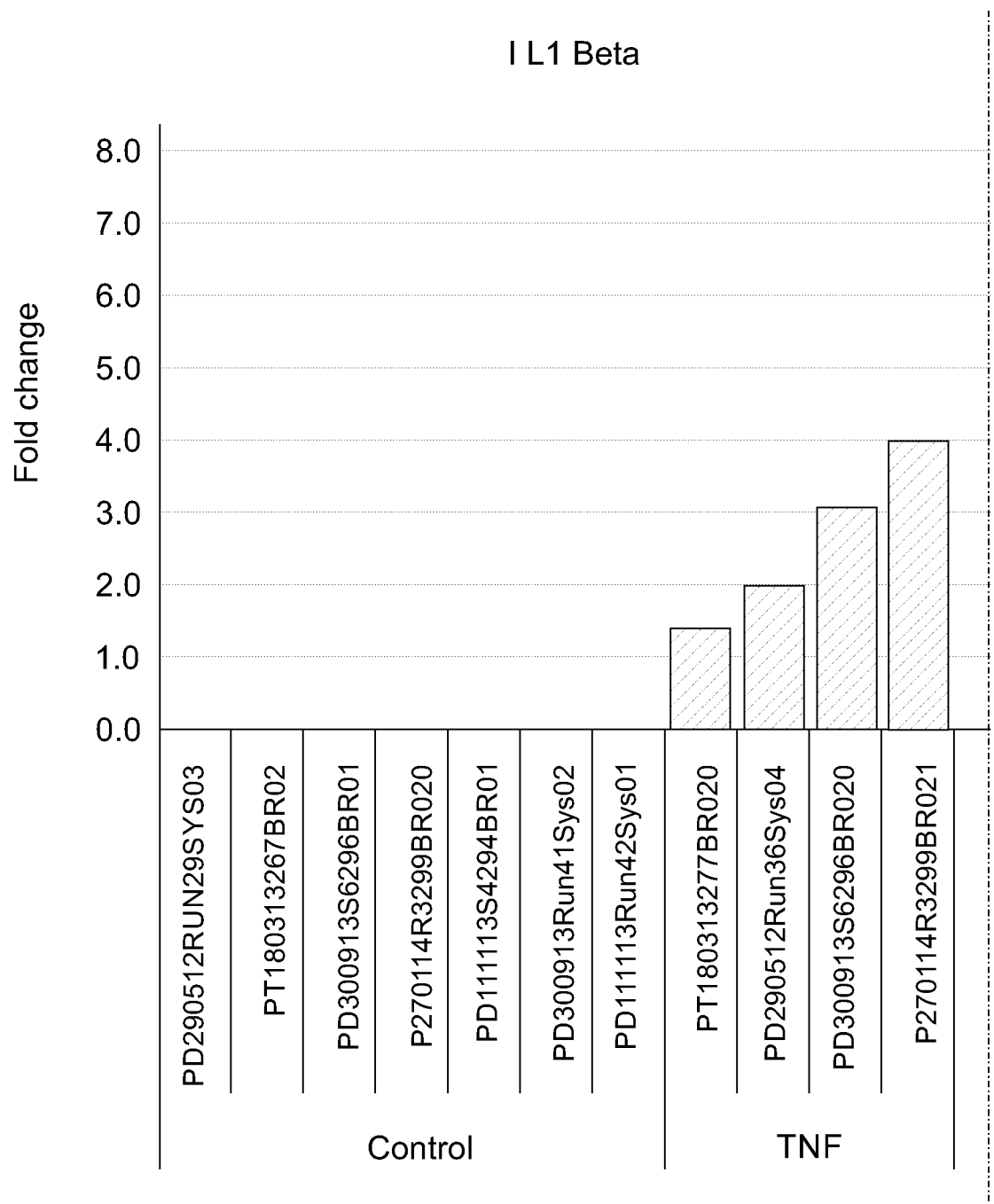
Figure 11D I

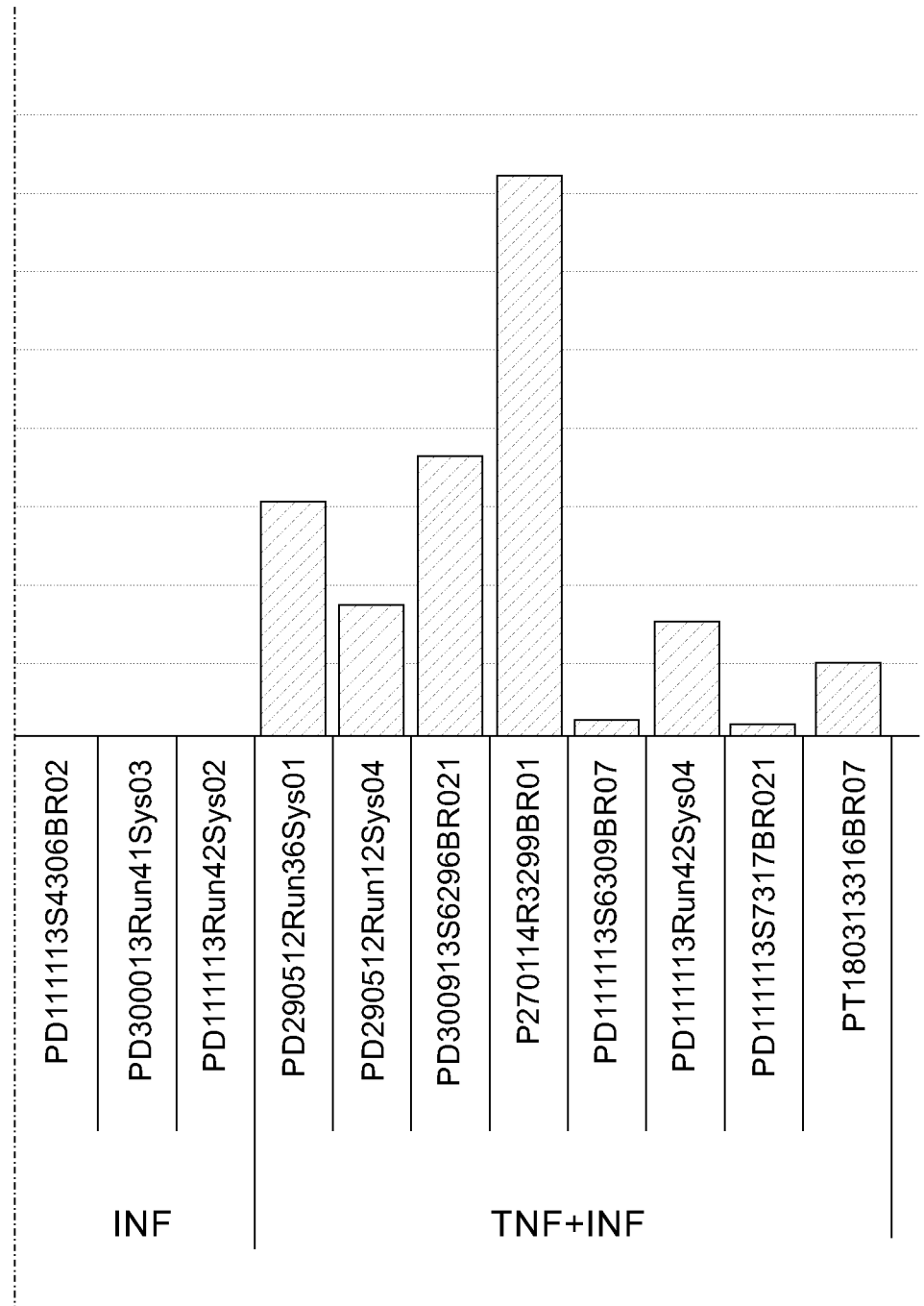
Figure 11D II

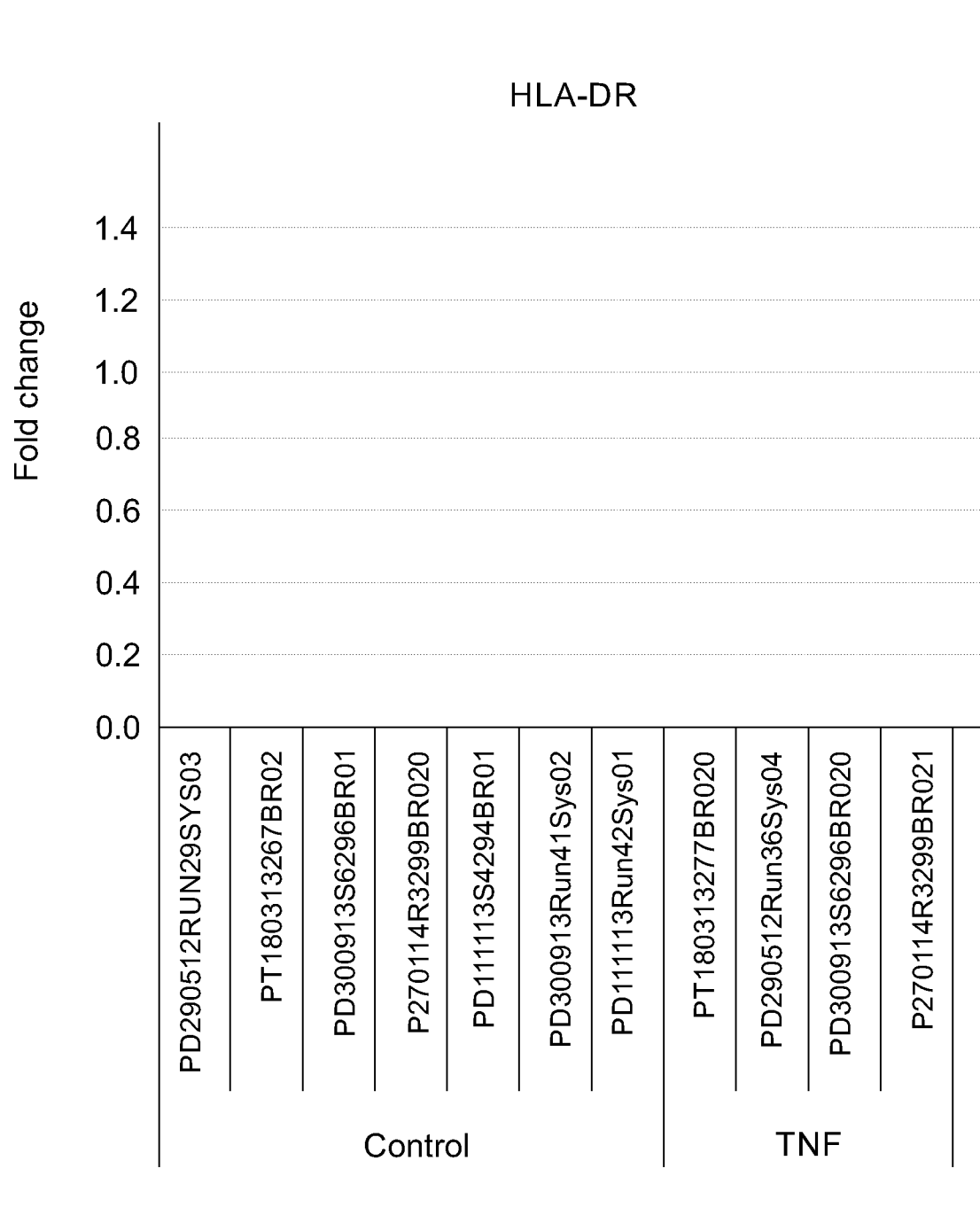
Figure 11E I

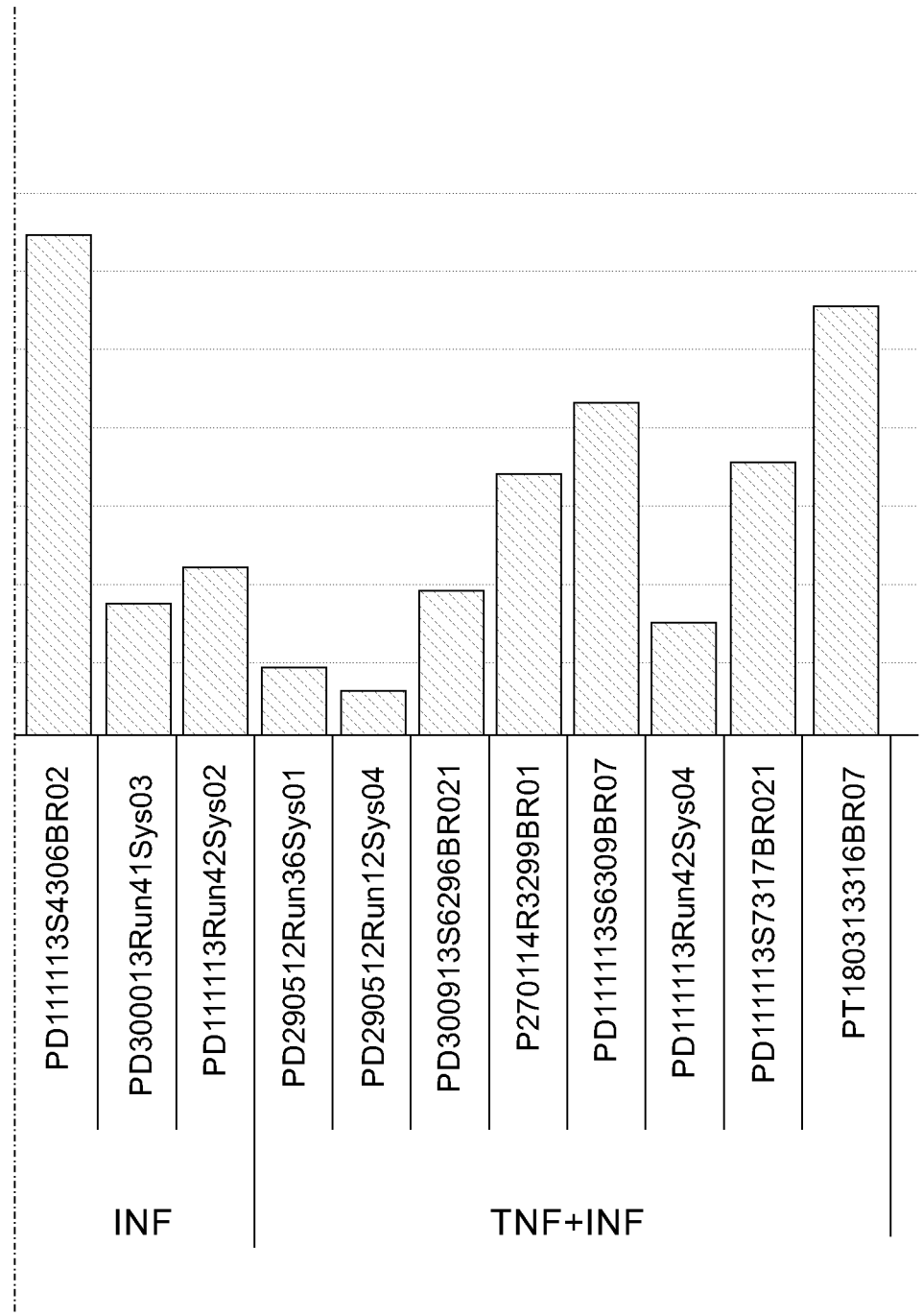
Figure 11E II

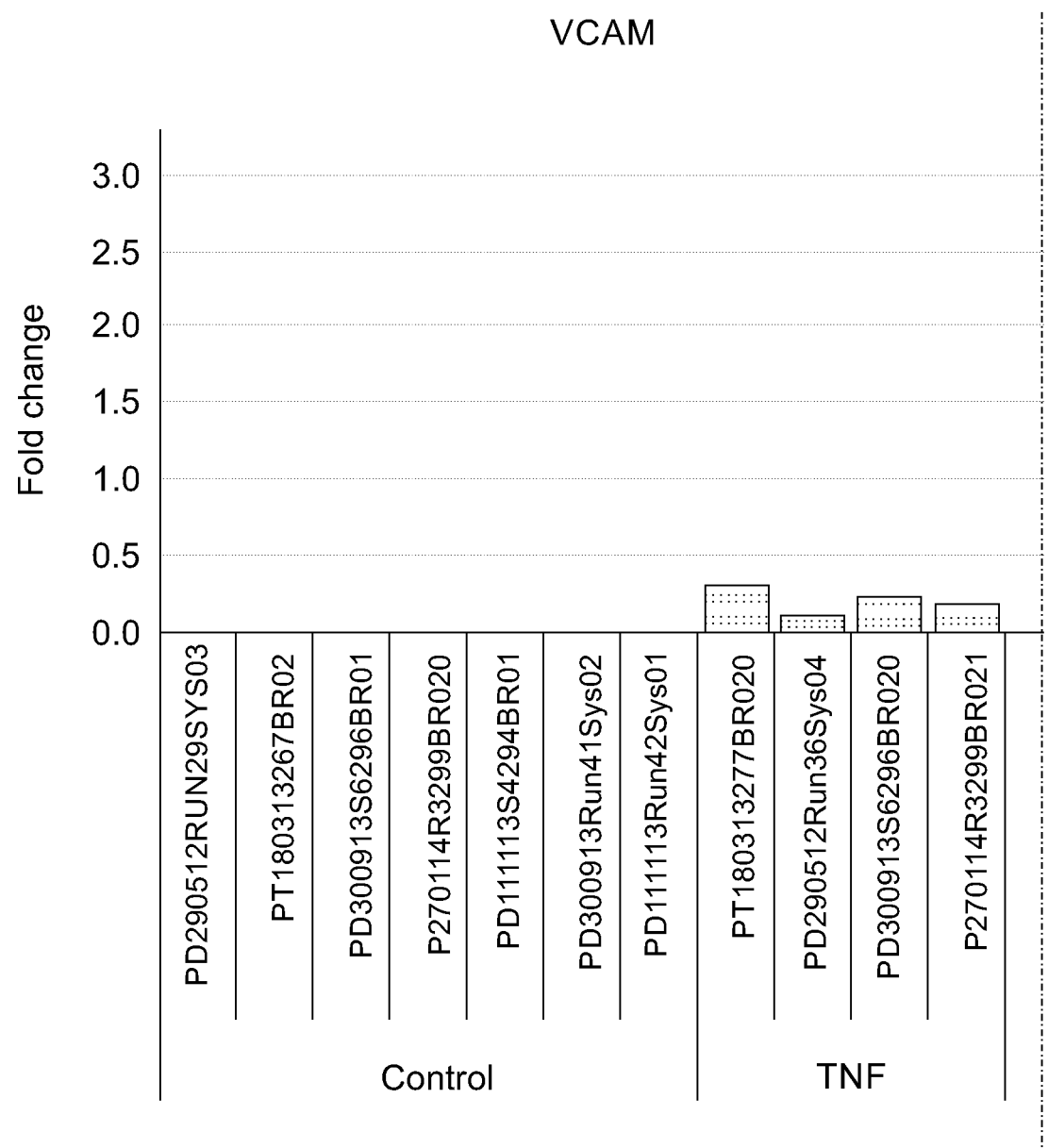
Figure 11F I

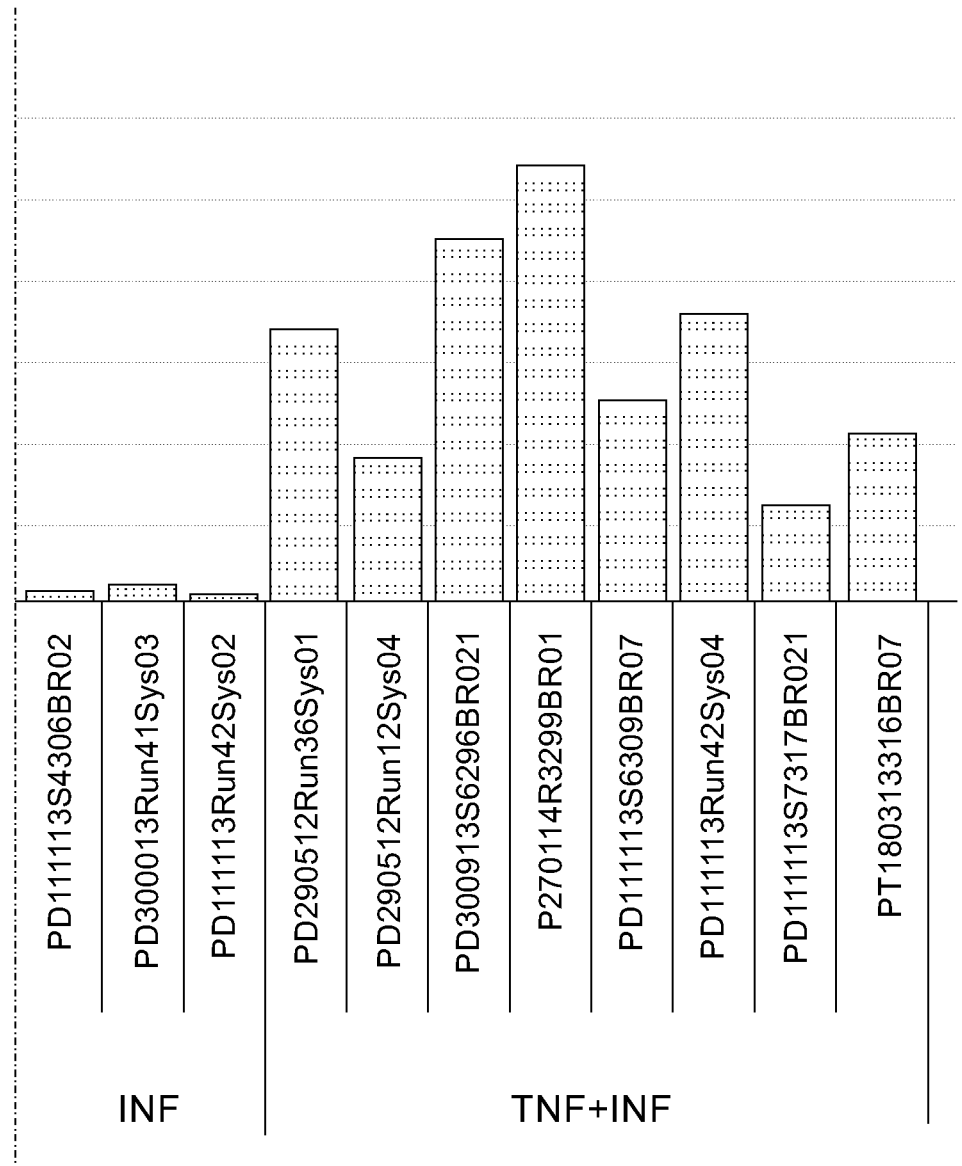
Figure 11F II

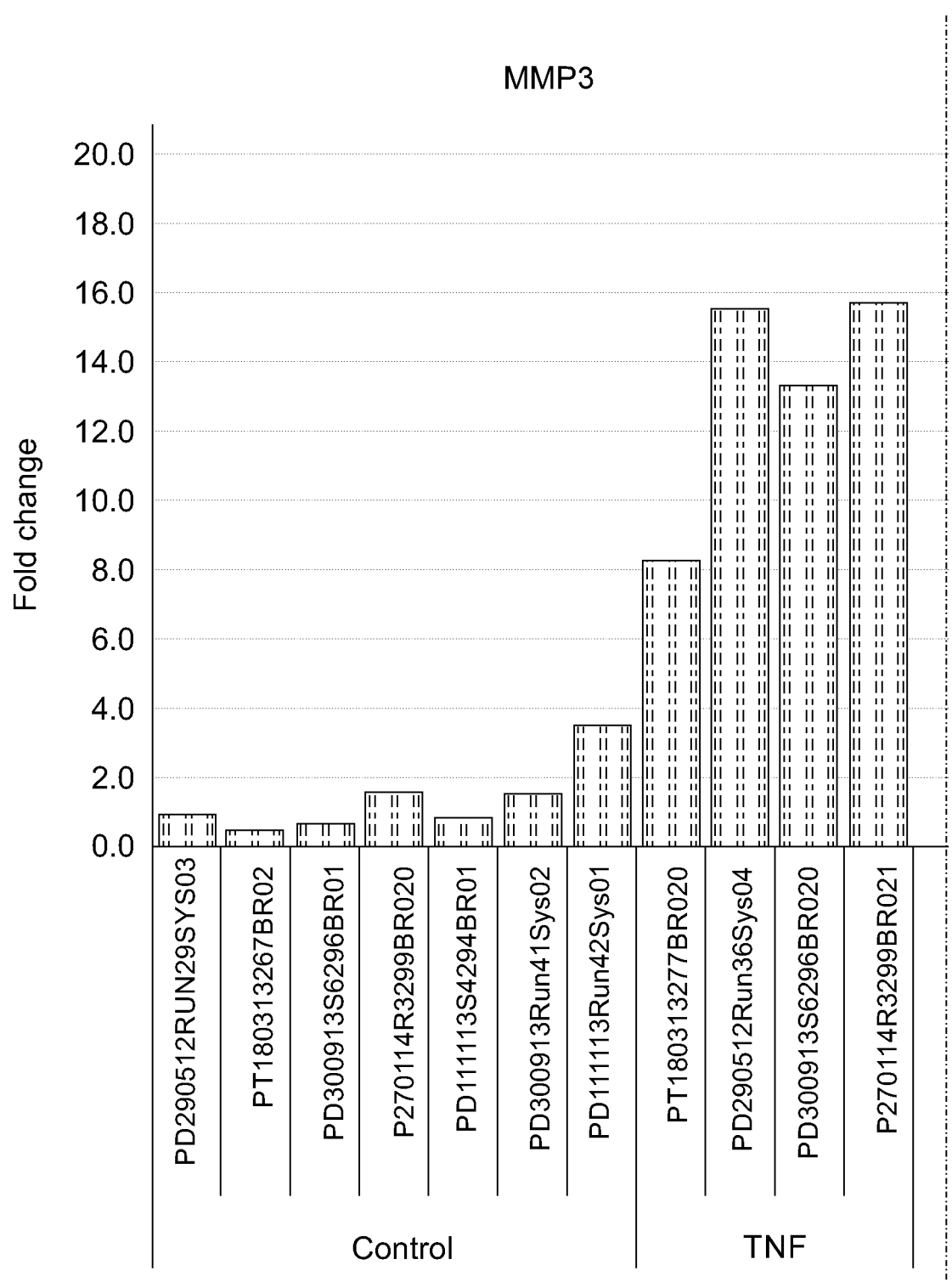
Figure 11G I

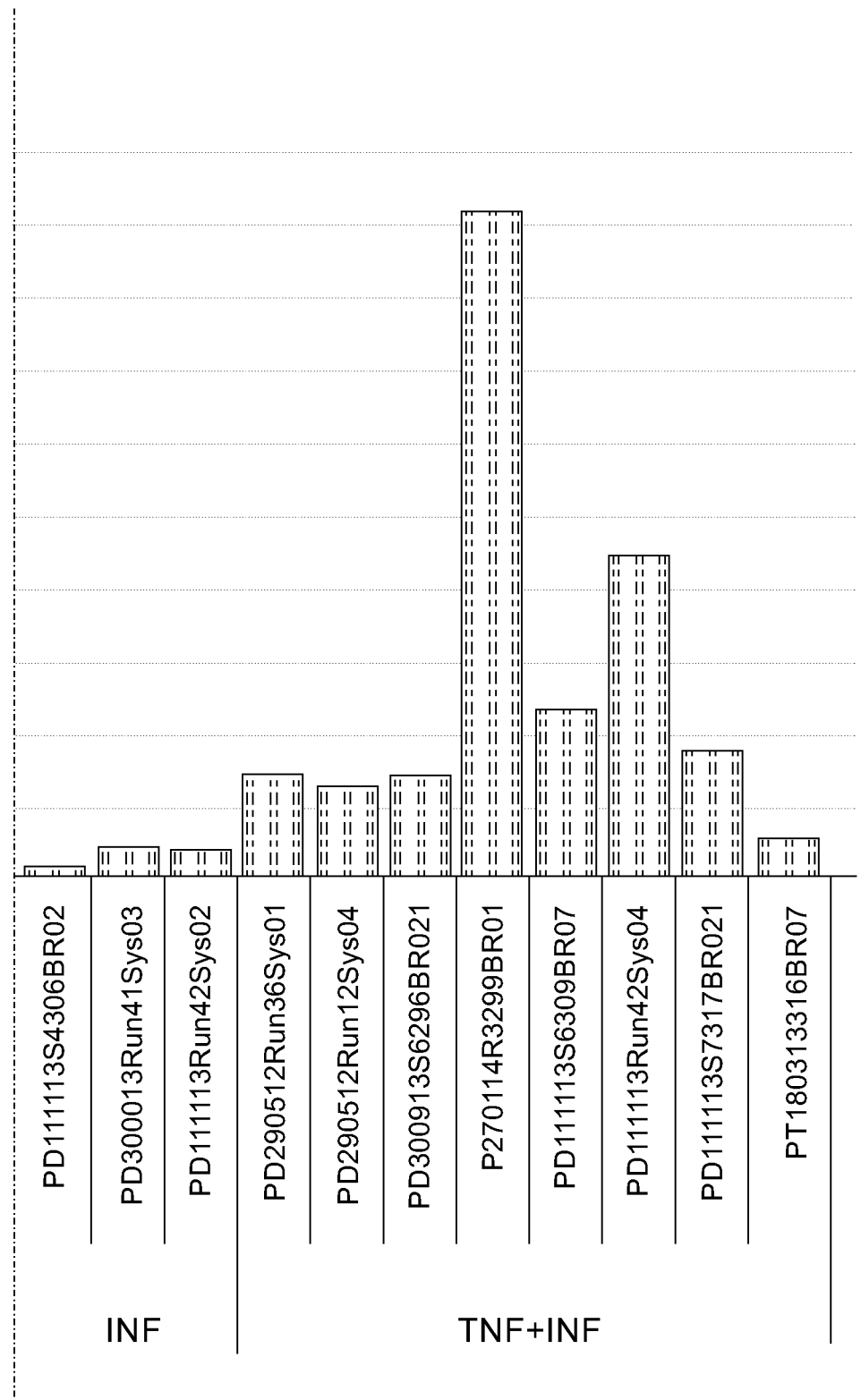
Figure 11G II

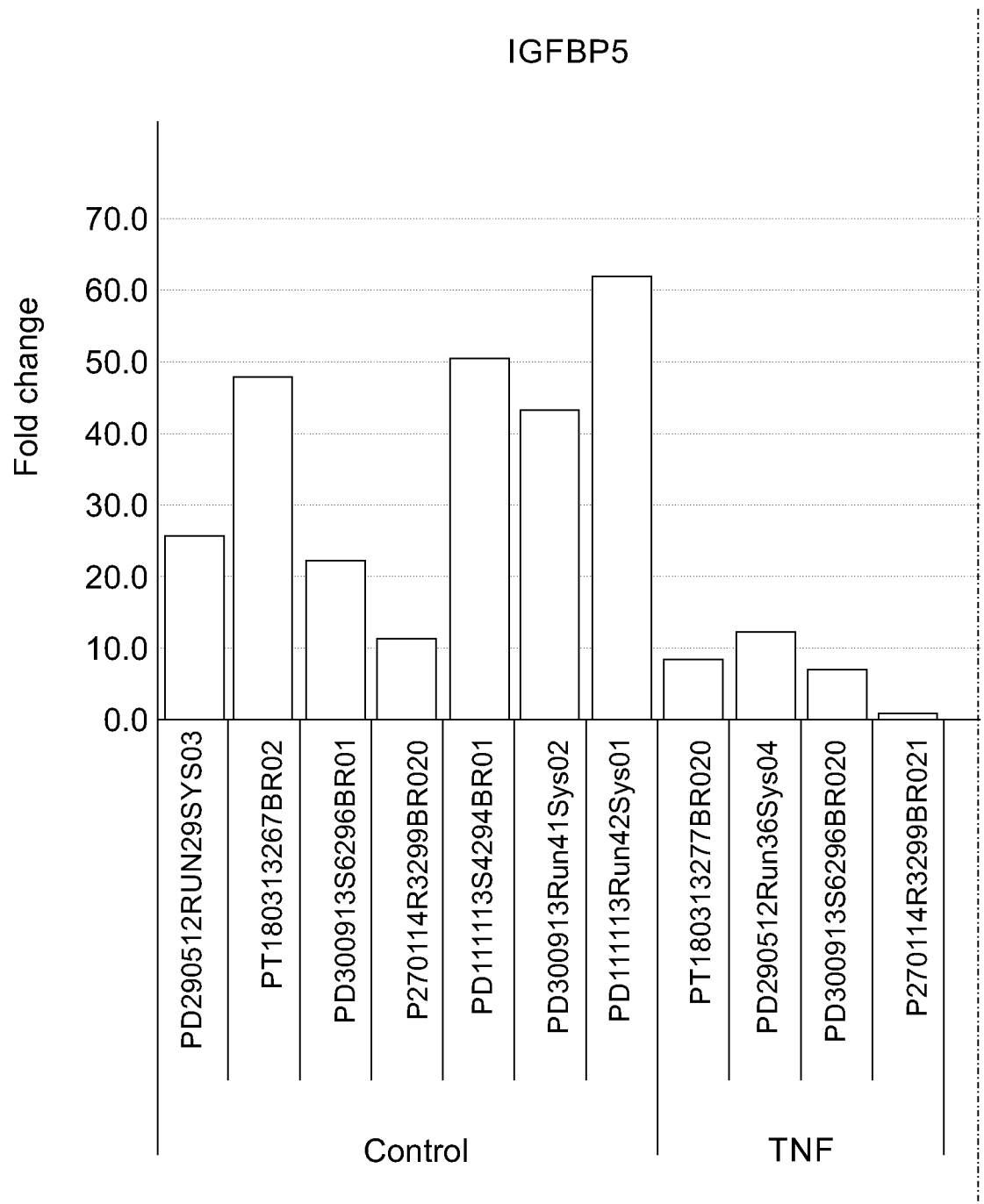
Figure 11H I

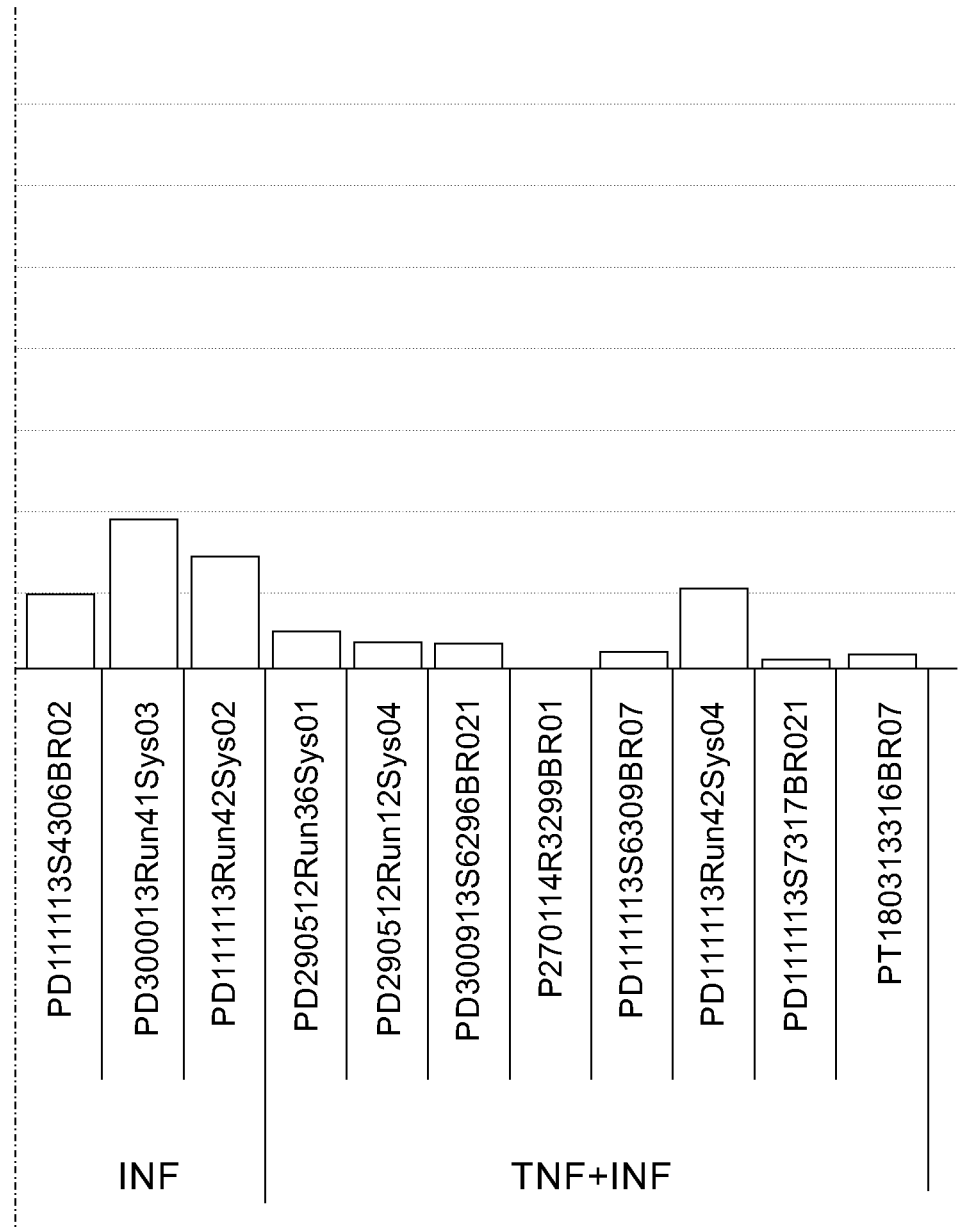
Figure 11H II

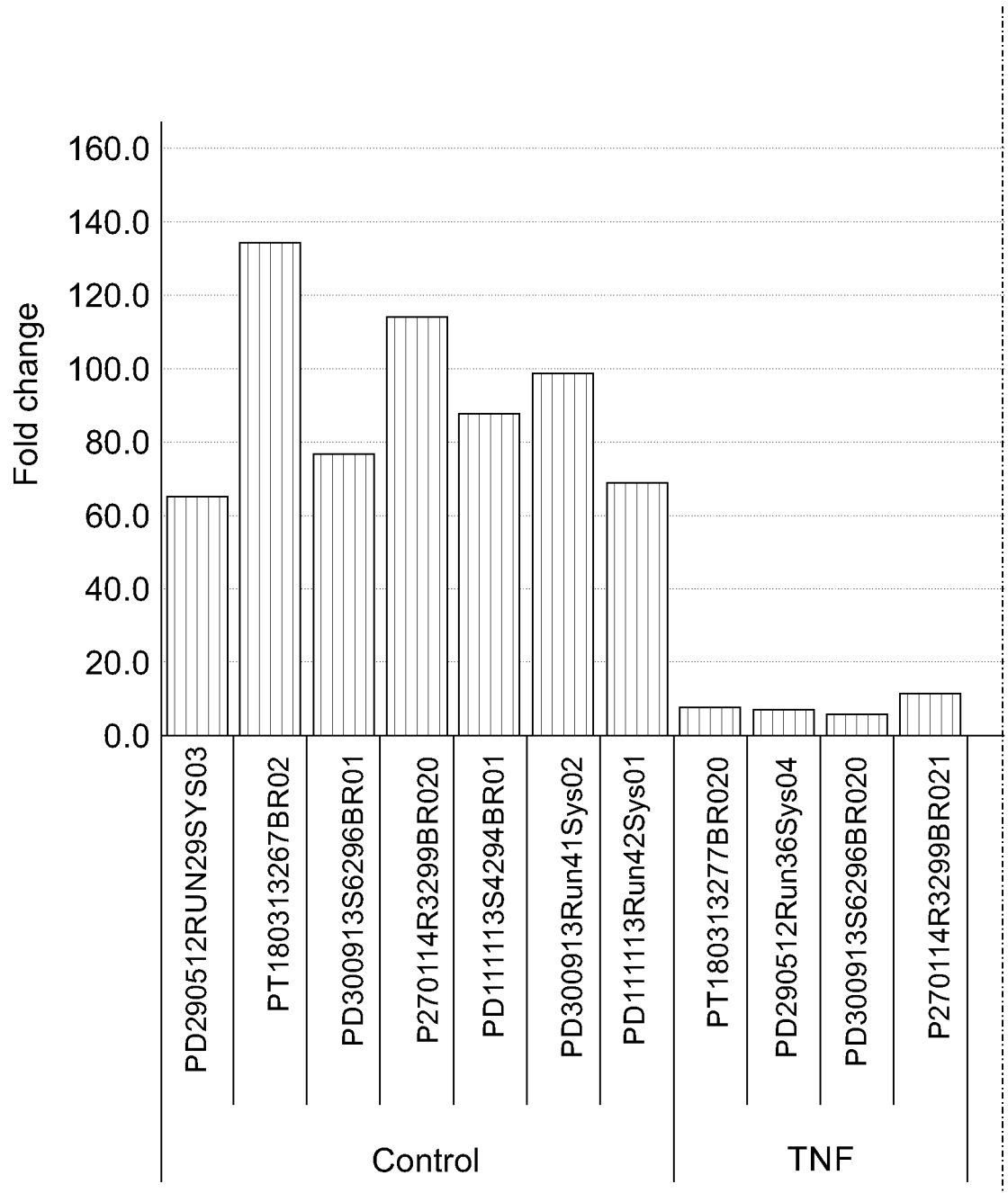
Figure 11I I

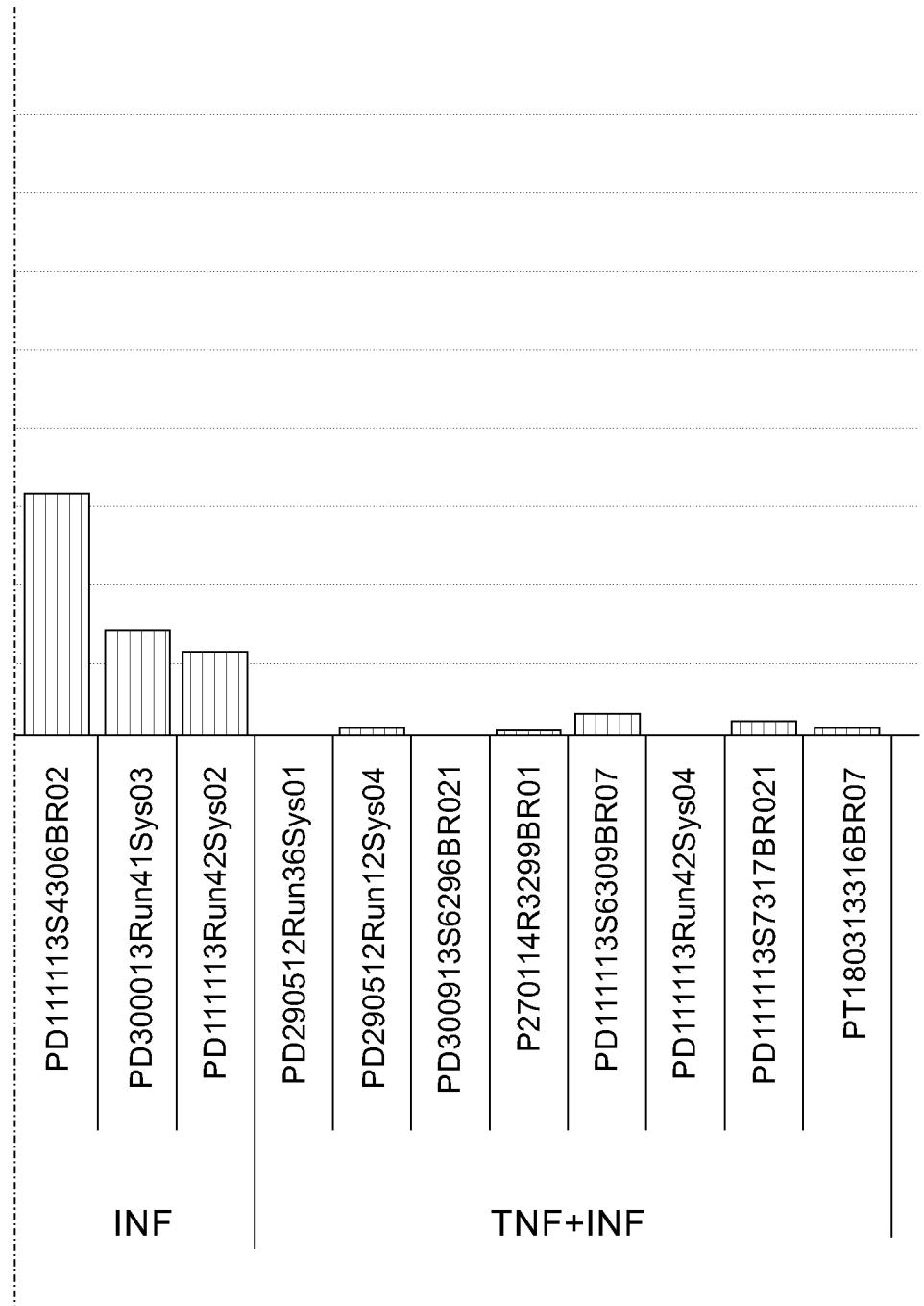
Figure 11I II

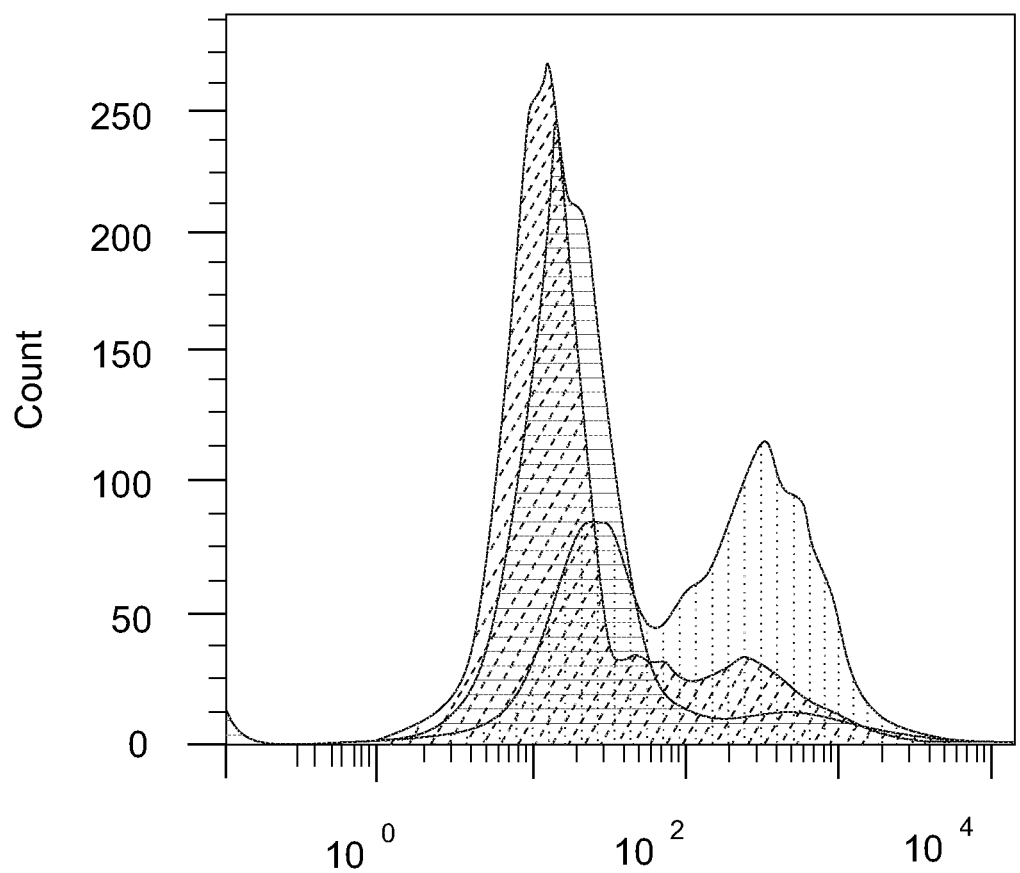
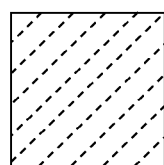 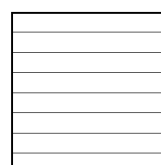 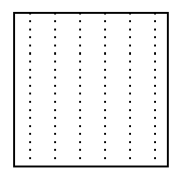
Figure 12F

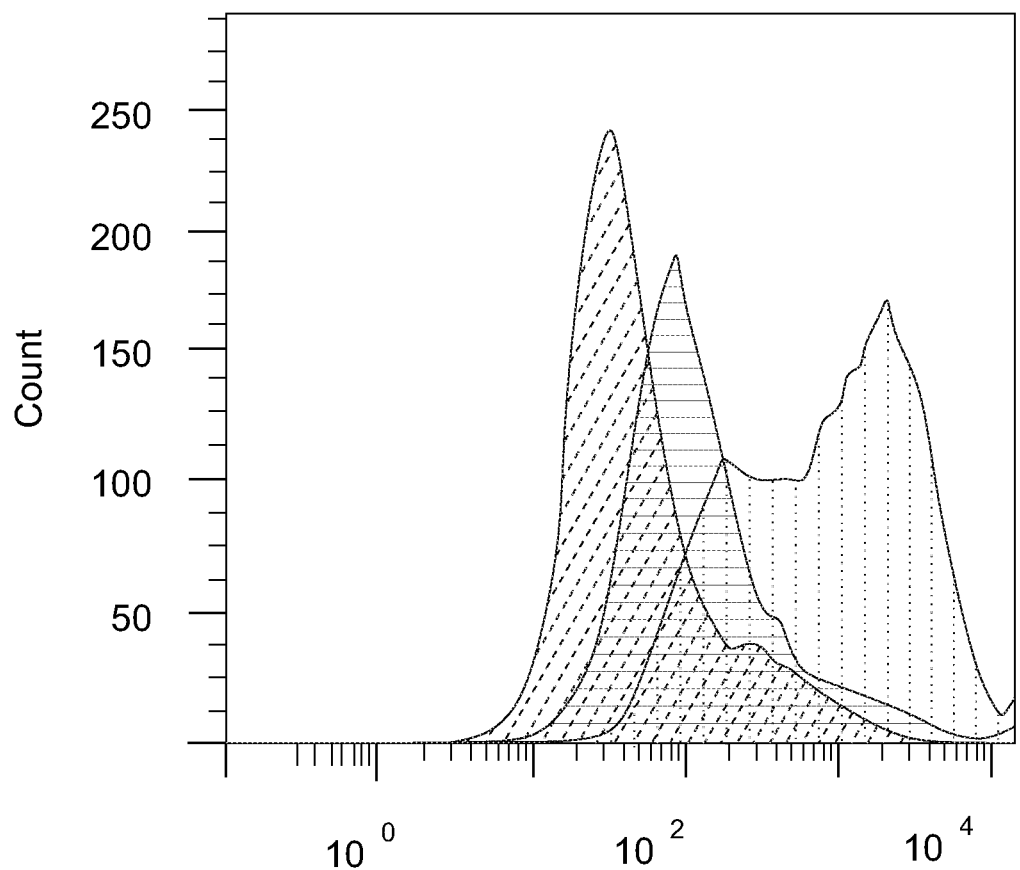
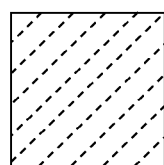 TNF
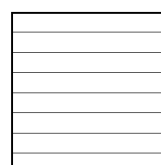 CONTROL
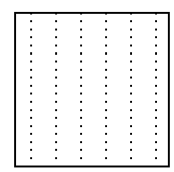 TNF-IFN
Figure 12I

ALTERED ADHERENT STROMAL CELLS AND METHODS OF PRODUCING AND USING SAME

CROSS REFERENCE TO RELATED APPLICATION

This application is a U.S. National Phase Application under 35 U.S.C. § 371 of International Application No. PCT/IB2016/053310, filed Jun. 6, 2016. The content of the aforementioned application is hereby incorporated by reference in its entirety.

FIELD

Disclosed herein are altered adherent stromal cells and methods of producing and utilizing same.

BACKGROUND

Emerging research is examining the effect of cytokine treatment on bone-marrow-derived mesenchymal stem cells (BM-MSC) (see Kavanagh D P et al). Placental-derived adherent stromal cells (placental ASC) differ from BM-MSC (Jeon Y J et al). While an isolated report has observed the effects of cytokine treatment on placental ASC (Li H et al), the effects of ex-vivo cytokine treatment on these cells are only beginning to be understood. Moreover, effective methods for cytokine stimulation of exponentially growing cells (for example, in a bioreactor) have not yet been developed.

SUMMARY

As provided herein, placental ASC have been expanded in medium containing effective amounts of inflammatory cytokines. In other embodiments, placental ASC have been expanded under a two-step process, the first step without added inflammatory cytokines, and the second step performed in the presence of inflammatory cytokines. These cells exhibit a unique set of characteristics and properties that are not believed to have any counterpart, either in nature or in previously-known artificially-produced cell compositions. They are, in some embodiments, primed as a result of the described ex-vivo treatment to produce or secrete elevated amounts of therapeutic factors. In still other embodiments, they are suitable for use in tissues far removed from their site of administration, or, in other embodiments, when administered systemically.

In certain embodiments, the ASC described herein have been cultured in 2-dimensional (2D) culture, prior to the described 3-dimensional (3D) culture. Non-limiting examples of 2D and 3D culture conditions are provided in the Detailed Description and in the Examples. The term "ASC", except where indicated otherwise, may refer, in various embodiments, to adherent stromal cells either before or after incubation with pro-inflammatory cytokines.

The terms "two-dimensional culture" and "2D culture" refer to a culture in which the cells are exposed to conditions that are compatible with cell growth and allow the cells to grow in a monolayer, which is referred to as a "two-dimensional culture apparatus". Such apparatuses will typically have flat growth surfaces, in some embodiments comprising an adherent material, which may be flat or curved. Non-limiting examples of apparatuses for 2D culture are cell culture dishes and plates. Included in this definition are multi-layer trays, such as Cell Factory™, manufactured by Nunc™, provided that each layer supports monolayer culture. It will be appreciated that even in 2D apparatuses, cells can grow over one another when allowed to become overconfluent. This does not affect the classification of the apparatus as "two-dimensional".

The terms "three-dimensional culture" and "3D culture" refer to a culture in which the cells are exposed to conditions that are compatible with cell growth and allow the cells to grow in a 3D orientation (for example, outside of the plane of a monolayer) relative to one another. The term "three-dimensional [or 3D] culture apparatus" refers to an apparatus for culturing cells under conditions that are compatible with cell growth and allow the cells to grow in a 3D orientation relative to one another. Such apparatuses will typically have a 3D growth surface, in some embodiments comprising an adherent material. Certain, non-limiting embodiments of 3D culturing conditions suitable for expansion of adherent stromal cells are described in PCT Application Publ. No. WO/2007/108003 and WO 2010/026575, the contents of which are incorporated by reference as if fully set forth herein.

Alternatively or in addition, the cells are mesenchymal-like ASC, which exhibit a marker pattern similar to mesenchymal stromal cells (MSC), but do not differentiate into osteocytes, under conditions where "classical" MSC would differentiate into osteocytes. In other embodiments, the cells exhibit a marker pattern similar to MSC, but do not differentiate into adipocytes, under conditions where MSC would differentiate into adipocytes. In still other embodiments, the cells exhibit a marker pattern similar to MSC, but do not differentiate into either osteocytes or adipocytes, under conditions where MSC would differentiate into osteocytes or adipocytes, respectively. The MSC used for comparison in these assays are, in some embodiments, MSC that have been harvested from bone marrow (BM) and cultured under 2D conditions. In other embodiments, the MSC used for comparison have been harvested from BM and cultured in 2D culture, followed by 3D culture. In more particular embodiments, the described mesenchymal-like ASC are placental cells of maternal origin. In alternative embodiments, the mesenchymal-like ASC are placental cells of fetal origin. In still other embodiments, the mesenchymal-like ASC are a mixture of maternal and fetal cells.

Except where otherwise indicated, all ranges mentioned herein are inclusive.

Except where otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the embodiments of the invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 9C-E are graphs depicting secreted protein concentration, in units of pg/ml, of various factors by unstimulated cells (control; horizontal dotted hatching) or cells stimulated with TNF-a alone (vertical hatching) or TNF-a+IFN-g (horizontal solid hatching).

FIG. 10 is a graph showing expression of RANTES (CCL5) in the following samples, ordered from left to right: placental cells not treated with cytokines (labeled control) or treated with TNF-alpha, IFN-gamma, or TNF-alpha+IFN-gamma (labeled TNF, INF, and TNF-INF, respectively). The expression level of a representative sample in the TNF-alpha+IFN-gamma group was arbitrarily assigned a value of 1.

FIGS. 11A-I are graphs showing expression as measured by qRT-PCR of IDO1 (A), IL18BP (B), MCP1/CCL2 (C), IL1beta (D), HLA-DR (E), CD106 (VCAM) (F), MMP3 (G), IGFBP5 (H), and RGS4 (I) in various batches of cells treated as follows, ordered from left to right: placental cells not treated with cytokines (control) or treated with TNF-alpha, IFN-gamma, or TNF-alpha+IFN-gamma (TNF, INF, and TNF-INF, respectively). The expression level of a representative sample from TNF-INF was arbitrarily assigned a value of 1.

FIGS. 12A-L are FACS plots depicting differential expression of various markers by unstimulated cells (control; horizontal hatching) or cells stimulated with TNF-alpha alone (diagonal hatching) or TNF-alpha+IFN-gamma (vertical hatching).

DETAILED DESCRIPTION

Figure 1:
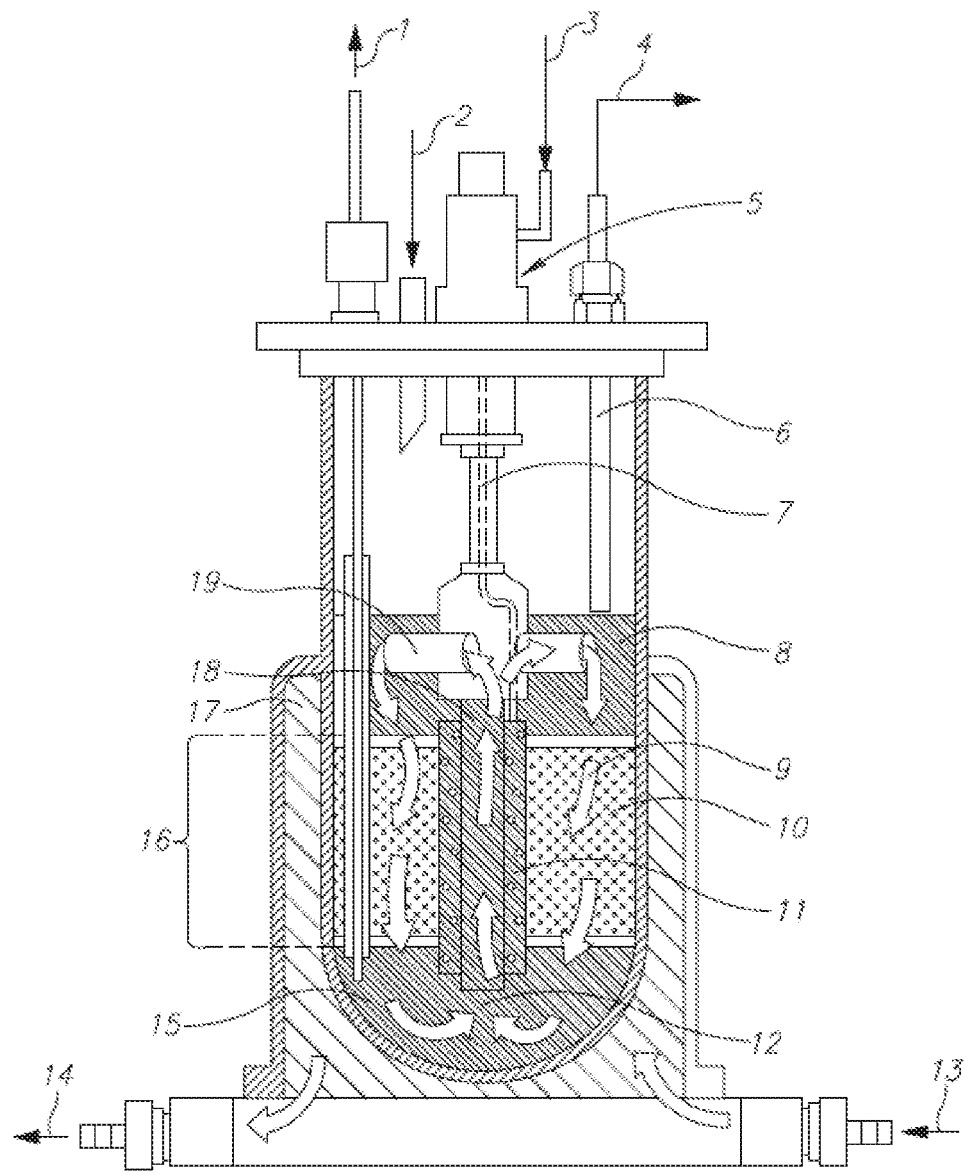
FIG. 1 is a diagram of a bioreactor that can be used to prepare the cells.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Provided herein are altered adherent stromal cells (ASC) and methods of producing, stimulating, and utilizing same. ASC may be derived, for example, from placenta; adipose tissue; bone marrow; peripheral blood; umbilical cord blood; synovial fluid; synovial membranes; spleen; thymus; mucosa (for example nasal mucosa); limbal stroma; ligaments, for example the periodontal ligament; scalp; hair follicles, testicles; embryonic yolk sac; and amniotic fluid, all of which are known to include adherent stromal cells. In certain embodiments, the source of the ASC is a non-fetal source, for example maternal cells from the placenta or somatic tissue from a pediatric or adult donor, for example adipose tissue, bone marrow, peripheral blood, umbilical cord blood, synovial fluid, synovial membranes, and ligaments such as the periodontal ligament. In some embodiments, the ASC are human ASC, while in other embodiments, they may be animal ASC. In particular embodiments, the ASC are derived from placental tissue, or are derived from adipose tissue.

In another embodiment is provided a method of producing modified ASC, the method comprising the step of incubating ASC in a three-dimensional (3D) culture apparatus in a growth medium, wherein one or more pro-inflammatory cytokines have been added to the growth medium, thereby producing modified ASC. In another embodiment is provided a method of producing modified ASC, the method comprising the steps of: (a) incubating ASC in a first growth medium, wherein no inflammatory cytokines have been added to the first growth medium; and (b) subsequently incubating the ASC in a 3D culture apparatus in a second growth medium, wherein one or more pro-inflammatory cytokines have been added to the second growth medium, thereby producing modified ASC. Each step of incubating typically is performed for at least 20 hours. In some embodiments, the incubation in the first growth medium is also done in a 3D culture apparatus. Those skilled in the art will appreciate, in light of the present disclosure, that the same 3D culture apparatus may be used for the incubations in the first and second growth medium by simply adding cytokines to the medium in the culture apparatus, or, in other embodiments, by removing the medium from the culture apparatus and replacing it with medium that contains cytokines. In other embodiments, a different 3D culture apparatus may be used for the incubation in the presence of cytokines, for example by moving (e.g. passaging) the cells to a separate container incubator, before adding the cytokine-containing medium, or in other embodiments by moving carriers with which the cells are associated to a different incubator. In various embodiments, reference to a "separate container" includes another containers within the same incubator and a separate incubator. Those skilled in the art will appreciate, in light of the present disclosure, that the ASC to be used in the described methods may be extracted from the placenta, from adipose tissue, or from other sources, as described herein.

In another embodiment is provided a method of producing modified ASC, the method comprising the steps of: (a) expanding ASC in a first growth medium, wherein no inflammatory cytokines have been added to the first growth medium; and (b) subsequently incubating the ASC during exponential growth phase in a second growth medium, wherein one or more pro-inflammatory cytokines have been added to the second growth medium, thereby producing modified ASC. Each step of incubating typically is performed for at least 20 hours. In some embodiments, the incubation in the first growth medium and the second growth medium are performed in a 3D culture apparatus. Those skilled in the art will appreciate, in light of the present disclosure, that the same 3D culture apparatus may be used for the incubations in the first and second growth medium by simply adding cytokines to the medium in the culture apparatus, or, in other embodiments, by removing the medium from the culture apparatus and replacing it with medium that contains cytokines. In other embodiments, a different 3D culture apparatus may be used for the incubation in the presence of cytokines, for example by moving (e.g. passaging) the cells to a different incubator, before adding the cytokine-containing medium, or in other embodiments by moving carriers with which the cells are associated to a different incubator. Those skilled in the art will appreciate, in light of the present disclosure, that the ASC to be used in the described methods may be extracted from the placenta, from adipose tissue, or from other sources, as described herein.

In other embodiments is provided a composition, comprising the described ASC. In certain embodiments, the composition further comprises a pharmacologically acceptable excipient. In further embodiments, the excipient is an osmoprotectant or cryoprotectant, an agent that protects cells from the damaging effect of freezing and ice formation, which may in some embodiments be a permeating compound, non-limiting examples of which are dimethyl sulfoxide (DMSO), glycerol, ethylene glycol, formamide, propanediol, poly-ethylene glycol, acetamide, propylene glycol, and adonitol; or may in other embodiments be a non-permeating compound, non-limiting examples of which are lactose, raffinose, sucrose, trehalose, and d-mannitol. In other embodiments, both a permeating cryoprotectant and a non-permeating cryoprotectant are present. In other embodiments, the excipient is a carrier protein, a non-limiting example of which is albumin. In still other embodiments, both an osmoprotectant and a carrier protein are present; in certain embodiments, the osmoprotectant and carrier protein may be the same compound. Alternatively or in addition, the composition is frozen. The cells may be any embodiment of ASC mentioned herein, each of which is considered a separate embodiment.

Those skilled in the art will appreciate that animal sera and other sources of growth factors are often included in growth media. In some cases, animal sera may contain inflammatory cytokines, which, in general, will not generally be present in large amounts. Some preparations utilize sera that are treated, for example with charcoal, so as to remove most or all of the cytokines present. In any event, reference herein to "added cytokines", "medium containing cytokines", or the like, does not encompass the presence of cytokines incidentally present in animal sera that is customarily included in the medium.

In still other embodiments is provided a culture, comprising the described ASC or in other embodiments a bioreactor, comprising the described culture. Except where indicated otherwise, the term "bioreactor" refers to an apparatus comprising a cell culture chamber and external medium reservoir (a non-limiting example of which is a feed bag) that is operably connected with the cell culture chamber so as to enable medium exchange between the two compartments (perfusion). The term excludes decellularized organs and tissues derived from a living being. In some embodiments, the bioreactor further comprises a synthetic material that is a 3D substrate. The cells may be any embodiment of ASC mentioned herein, each of which is considered a separate embodiment.

In still other embodiments is provided a suspension comprising any of the described cell populations. In certain embodiments, the suspension comprises a pharmaceutically acceptable excipient. In other embodiments, the suspension is a pharmaceutical composition. In still other embodiments, the suspension is frozen and further comprises, in some embodiments, a cryoprotectant. In other embodiments is provided a composition, comprising the suspension. In certain embodiments, the composition further comprises a pharmacologically acceptable excipient. In further embodiments, the excipient is a cryopreservant (cryoprotectant), or is a carrier protein. Alternatively or in addition, the composition is frozen. Each of the aforementioned cell populations represents a separate embodiment in this regard.

In various embodiments, the described ASC are able to exert the described therapeutic effects, each of which is considered a separate embodiment, with or without the ASC themselves engrafting in the host. For example, the cells may, in various embodiments, be able to exert a therapeutic effect, without themselves surviving for more than 3 days, more than 4 days, more than 5 days, more than 6 days, more than 7 days, more than 8 days, more than 9 days, more than 10 days, or more than 14 days.

Reference herein to one or more "pro-inflammatory" cytokines, or "inflammatory cytokines", which is used interchangeably, implies the presence of at least one cytokine that mediates an inflammatory response in a mammalian host, for example a human host. A non-limiting list of cytokines are Interferon-gamma (IFN-gamma or IFN-γ; UniProt identifier P01579), IL-22 (UniProt identifier Q9GZX6), Tumor Necrosis Factor-alpha (TNF-alpha; UniProt identifier P01375), IFN-alpha, IFN-beta (UniProt identifier P01574), IL-1alpha (UniProt identifier P01583), IL-1beta (UniProt identifier P01584), IL-17 (UniProt identifier Q5QEX9), IL-23 (UniProt identifier Q9NPF7), IL-17A (UniProt identifier Q16552), IL-17F (UniProt identifier Q96PD4), IL-21 (UniProt identifier Q9HBE4), IL-13 (UniProt identifier P35225), IL-5 (UniProt identifier P05113), IL-4 (UniProt identifier P05112), IL-33 (UniProt identifier O95760), IL-1RL1 (UniProt identifier Q01638), TNF-Beta (UniProt identifier P01374), IL-11 (UniProt identifier P20809), IL-9 (UniProt identifier P15248), IL-2 (UniProt identifier P60568), IL-21 (UniProt identifier Q9HBE4), Tumor Necrosis Factor-Like Ligand (TL1A; a.k.a. TNF ligand superfamily member 15; UniProt identifier O95150), IL-12 (UniProt identifiers P29459 and P29460 for the alpha- and beta subunits, respectively), and IL-18 (UniProt identifier Q14116). Additional cytokines include (but are not limited to): Leukemia inhibitory factor (LIF; UniProt identifier P15018), oncostatin M (OSM; UniProt identifier P13725), ciliary neurotrophic factor (CNTF (UniProt identifier P26441), and IL-8 (UniProt identifier P10145). All Swissprot and UniProt entries were accessed on Jul. 24, 2014, except where indicated otherwise.

Except where indicated otherwise, reference to a cytokine or other protein is intended to include all isoforms of the protein. For example, IFN-alpha includes all the subtypes and isoforms thereof, such as but not limited to IFN-alpha 17, IFN-alpha 4, IFN-alpha 7, IFN-alpha 8, and IFN-alpha 110. Some representative UniProt identifiers for IFN-alpha are P01571, P05014, P01567, P32881, and P01566. Those skilled in the art will appreciate that, even in the case of human cells, the aforementioned cytokines need not be human cytokines, since many non-human (e.g. animal) cytokines are active on human cells. Similarly, the use of modified cytokines that have similar activity to the native forms falls within the scope of the described methods and compositions.

In certain embodiments, the cytokine present in the described medium, or in other embodiments at least one of the cytokines present, if more than one is present, is an inflammatory cytokine that affects innate immune responses. In further embodiments, the cytokine is one of, or in other embodiments more than one, of TNF-a, IL-1 alpha, IL-10, IL-12, IFN-α IFN-β, or IFN-γ.

In other embodiments, the cytokine, or in other embodiments at least one of the cytokines, if more than one is present, is an inflammatory cytokine that affects adaptive immune responses. In further embodiments, the cytokine is one of, or in other embodiments more than one, of IL-2, IL-4, IL-5, TGF-β, IL-10 or IFN-γ.

In still other embodiments, the cytokine, or in other embodiments at least one of the cytokines, if more than one is present, is a Th1 cytokine. In further embodiments, the cytokine is one of, or in other embodiments more than one, of IFN-gamma, IL-22, TNF-alpha, IL-1 alpha, or IL-1beta.

In still other embodiments, the cytokine, or in other embodiments at least one of the cytokines, if more than one is present, is a Th17 cytokine. In further embodiments, the cytokine is one of, or in other embodiments more than one, of IL-17, IL-23, IL-17A, IL-17F, IL-21, IL-22, TNF-alpha, or granulocyte macrophage colony stimulating factor (GM-CSF; UniProt identifier P04141).

In yet other embodiments, the cytokine, or in other embodiments at least one of the cytokines, if more than one is present, is selected from a Th1 cytokine and a Th17 cytokine.

In still other embodiments, the cytokine, or in other embodiments at least one of the cytokines, if more than one is present, is a Th2 cytokine. In further embodiments, the cytokine is one of, or in other embodiments more than one, of IL-13, IL-5, IL-4, IL-33, IL-1RL1, TNF-Alpha, and TNF-Beta. In other embodiments, the cytokine is one of, or in other embodiments more than one, of IL-13, IL-5, IL-33, IL-1RL1, TNF-Alpha, or TNF-Beta.

In yet other embodiments, the cytokine(s) is one of, or in other embodiments more than one, of IL-11 (maybe IL-9, IL-2, I think IL-21) Leukemia inhibitory factor (LIF), oncostatin M (OSM), ciliary neurotrophic factor (CNTF), granulocyte macrophage colony stimulating factor (GM-CSF), and IL-8. In further embodiments, the cytokine(s) is one or more of IL-11, LIF, OSM, CNTF, GM-CSF, or IL-8.

In other embodiments, the cytokine(s) is one of, or in other embodiments more than one, of: TNF-α, IL-1beta, or TL1A.

In yet other embodiments, the cytokine(s) is one of, or in other embodiments more than one, of IL-12, IL-18, or TNF-α.

In more specific embodiments, one of the aforementioned cytokines is present in the perfusion medium in an amount of 0.1-10 ng/ml; 0.15-10 ng/ml; 0.2-10 ng/ml; 0.3-10 ng/ml; 0.4-10 ng/ml; 0.5-10 ng/ml; 0.7-10 ng/ml; 1-10 ng/ml; 1.5-10 ng/ml; 2-10 ng/ml; 3-10 ng/ml; 4-10 ng/ml; 5-10 ng/ml; 0.1-5 ng/ml; 0.2-5 ng/ml; 0.3-5 ng/ml; 0.4-5 ng/ml; 0.5-5 ng/ml; 0.7-5 ng/ml; 1-5 ng/ml; 2-5 ng/ml; 0.1-3 ng/ml; 0.2-3 ng/ml; 0.3-3 ng/ml; 0.4-3 ng/ml; 0.5-3 ng/ml; 0.6-3 ng/ml; 0.8-3 ng/ml; 1-3 ng/ml; 1.5-3 ng/ml; 0.1-2 ng/ml; 0.2-2 ng/ml; 0.3-2 ng/ml; 0.4-2 ng/ml; 0.5-2 ng/ml; 0.6-2 ng/ml; 0.8-2 ng/ml; 1-2 ng/ml; 0.5-1.5 ng/ml; 0.6-1.5 ng/ml; 0.6-1.4 ng/ml; 0.7-1.3 ng/ml; 0.8-1.2 ng/ml; 0.1-0.8 ng/ml; 0.1-0.6 ng/ml; 0.1-0.5 ng/ml; 0.1-0.4 ng/ml; 0.2-1 ng/ml; 0.2-0.8 ng/ml; 0.2-0.6 ng/ml; 0.2-0.5 ng/ml; 0.2-0.4 ng/ml; 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml;

8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; 2-4 ng/ml; 10-1000 ng/ml; 20-1000 ng/ml; 30-1000 ng/ml; 40-1000 ng/ml; 50-1000 ng/ml; 70-1000 ng/ml; 100-1000 ng/ml; 150-1000 ng/ml; 200-1000 ng/ml; 300-1000 ng/ml; 400-1000 ng/ml; 500-1000 ng/ml; 10-500 ng/ml; 20-500 ng/ml; 30-500 ng/ml; 40-500 ng/ml; 50-500 ng/ml; 70-500 ng/ml; 100-500 ng/ml; 200-500 ng/ml; 10-300 ng/ml; 20-300 ng/ml; 30-300 ng/ml; 40-300 ng/ml; 50-300 ng/ml; 60-300 ng/ml; 80-300 ng/ml; 100-300 ng/ml; 150-300 ng/ml; 10-200 ng/ml; 20-200 ng/ml; 30-200 ng/ml; 40-200 ng/ml; 50-200 ng/ml; 60-200 ng/ml; 80-200 ng/ml; 100-200 ng/ml; 50-150 ng/ml; 60-15 ng/ml; 60-14 ng/ml; 70-130 ng/ml; 80-120 ng/ml; 10-100 ng/ml; 10-80 ng/ml; 10-60 ng/ml; 10-50 ng/ml; 10-40 ng/ml; 20-100 ng/ml; 20-80 ng/ml; 20-60 ng/ml; 20-50 ng/ml; or 20-40 ng/ml. As provided herein, for example, cells were perfused overnight with medium containing 10 ng/ml of IFN-gamma and/or TNF-alpha. In still other embodiments, when more than one cytokine is present, each of them is present in an amount independently selected from the above amounts, which may be freely combined. In various other embodiments, the amounts of each of the proinflammatory cytokines present are each within one of the above ranges.

In certain embodiments, one or more of the cytokines is TNF-alpha (also referred to herein as TNF-a). In more specific embodiments, the TNF-a may be the only cytokine present, or, in other embodiments, may be present together with 1, 2, 3, 4, 5, 6, 1-2, 1-3, 1-4, 1-5, or 1-6, or more than 6 added inflammatory cytokines, which may be, in certain embodiments, one of the aforementioned cytokines. In more specific embodiments, TNF-alpha is present in the perfusion medium in an amount of 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; or 2-4 ng/ml. As provided herein, for example, cells were perfused overnight with medium containing 10 ng/ml of TNF-α.

In some embodiments, TNF-alpha is present together with IFN-gamma (also referred to herein as IFN-g). These two cytokines may be the only 2 added cytokines, or, in other embodiments, present with additional proinflammatory cytokines. In still other embodiments, IFN-gamma and TNF-alpha are each present in the perfusion medium in an amount independently selected from one of the aforementioned amounts or ranges. Each combination may be considered as a separate embodiment. In still other embodiments, the amounts of IFN-g and TNF-a in the perfusion medium are both within a range of 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; or 2-4 ng/ml. As provided herein, for example, cells were perfused overnight with medium containing 10 ng/ml of IFN-g and/or TNF-a.

In still other embodiments, the concentrations of IFN-g and TNF-a in the perfusion medium are both between 1-15 ng/ml, 1-12 ng/ml, 1-10 ng/ml, 1-8 ng/ml, 1-6 ng/ml, 1-5 ng/ml, 2-15 ng/ml, 2-12 ng/ml, 2-10 ng/ml, 3-15 ng/ml, 3-12 ng/ml, 3-10 ng/ml, 5-15 ng/ml, 5-12 ng/ml, or 5-10 ng/ml. In still other embodiments, the ratio of the concentrations of IFN-g and TNF-a in the perfusion medium is between 1:5-5:1, between 1:4-4:1, between 1:3-3:1, between 1:2-2:1, or between 1:1.5-1.5:1. In yet other embodiments, the IFN-g and TNF-a concentrations in the perfusion medium are both between 1-5 ng/ml, and the ratio of these concentrations is between 1:2-2:1; the IFN-g and TNF-a concentrations in the perfusion medium are both between 5-10 ng/ml, and the ratio of these concentrations is between 1:2-2:1; the IFN-g and TNF-a concentrations in the perfusion medium are both between 1-5 ng/ml, and the ratio of these concentrations is between 1:1.1-1.5:1; or the IFN-g and TNF-a concentrations in the perfusion medium are both between 5-10 ng/ml, and the ratio of these concentrations is between 1:1.5-1.5:1. In more specific embodiments, the ASC are perfused with one of the aforementioned combinations of concentrations of IFN-g and TNF-a for a time period between 20-40 hours, between 20-36 hours, between 20-32 hours, between 22-30 hours, between 22-28 hours, between 22-26 hours, or between 23-25 hours, in a bioreactor, or in other embodiments, in another type of tissue culture apparatus, for example a 2D culture apparatus.

Reference herein to a concentration(s) in the perfusion medium indicates the concentration in the medium before addition to the cells-which, in one embodiment, is the external medium reservoir of a bioreactor. In some embodiments, the observed concentration of cytokines in the culture apparatus at the end of an incubation (for example, in a bioreactor) may vary from the concentrations in the medium before addition to the cells.

In other embodiments, ASC are perfused with a sufficient IFN-g concentration to achieve a concentration in the incubation medium at the end of the incubation (the final actual concentrations) that is between 0.5-5 ng/ml, 0.5-4 ng/ml, 0.5-3 ng/ml, 0.5-1 ng/ml, 0.7-5 ng/ml, 0.7-4 ng/ml, 0.7-3 ng/ml, 0.7-2 ng/ml, 1-5 ng/ml, 1-4 ng/ml, 1-3 ng/ml, 1-2 ng/ml, or 2-3 ng/ml. In other embodiments, ASC are perfused with a sufficient TNF-a concentration to achieve a final actual concentration that is between 0.5-5 ng/ml, 0.5-4 ng/ml, 0.5-3 ng/ml, 0.5-1 ng/ml, 0.7-5 ng/ml, 0.7-4 ng/ml, 0.7-3 ng/ml, 0.7-2 ng/ml, 1-5 ng/ml, 1-4 ng/ml, 1-3 ng/ml, 1-2 ng/ml, or 2-3 ng/ml. In other embodiments, ASC are perfused with sufficient concentrations of IFN-g and TNF-a to achieve final actual concentrations that are both between 0.5-5 ng/ml, 0.5-4 ng/ml, 0.5-3 ng/ml, 0.5-1 ng/ml, 0.7-5 ng/ml, 0.7-4 ng/ml, 0.7-3 ng/ml, 0.7-2 ng/ml, 1-5 ng/ml, 1-4 ng/ml, 1-3 ng/ml, 1-2 ng/ml, or 2-3 ng/ml. In still other embodiments, the ratio of the final actual concentrations of IFN-g and TNF-a in the perfusion medium is between 1:5-5:1, between 1:4-4:1, between 1:3-3:1, between 1:2-2:1, or between 1:1.5-1.5:1. In yet other embodiments, the IFN-g and TNF-a concentrations in the perfusion medium are sufficient to achieve final actual concentrations that are both between 1-2 ng/ml, and the ratio of the final actual concentrations is between 1:2-2:1; the final actual IFN-g and TNF-a concentrations are both between 2-3 ng/ml, and at a ratio between 1:2-2:1; the final actual IFN-g and TNF-a concentrations are both between 1-2 ng/ml, and at a ratio between 1:1.1-1.5:1; or the final actual IFN-g and TNF-a concentrations are both between 2-3 ng/ml, and at a ratio between 1:1.5-1.5:1.

In more specific embodiments, the ASC are incubated under one of the aforementioned conditions for a time period between 20-40 hours, between 20-36 hours, between 20-32 hours, between 22-30 hours, between 22-28 hours, between 22-26 hours, or between 23-25 hours, in a bioreactor, or in other embodiments, in another type of tissue culture apparatus, for example a 2D culture apparatus.

As mentioned, in some embodiments, TNF-a is present together with one, or in other embodiments 2, 3, 4, 5, or more than 5, of the aforementioned cytokines. In still other embodiments, TNF-a and one, or in other embodiments more than one, of the additional cytokines is each present in the perfusion medium in an amount independently selected from one of the aforementioned amounts or ranges. Each combination may be considered as a separate embodiment. In still other embodiments, the amounts of TNF-a and the other cytokine(s) are both present the perfusion medium within a range of 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; or 2-4 ng/ml. As provided herein, for example, cells were perfused overnight with medium containing 10 ng/ml of IFN-g and/or TNF-a.

In certain embodiments, one or more of the cytokines is IFN-g. In more specific embodiments, the IFN-g may be the only cytokine present, or, in other embodiments, may be present together with 1, 2, 3, 4, 5, 6, 1-2, 1-3, 1-4, 1-5, or 1-6, or more than 6 added cytokines. In more specific embodiments, IFN-g is present in the perfusion medium in an amount of 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; or 2-4 ng/ml. As provided herein, for example, cells were perfused overnight with medium containing 10 ng/ml of IFN-g.

As mentioned, in some embodiments, IFN-g is present together with one of the aforementioned cytokines. These two cytokines may be the only 2 added cytokines, or, in other embodiments, present with additional proinflammatory cytokines. In still other embodiments, IFN-g and one, or in other embodiments more than one, of the additional cytokines is each present in an amount independently selected from one of the aforementioned amounts or ranges. Each combination may be considered as a separate embodiment. In still other embodiments, the amounts of IFN-g and the other cytokine(s) are both present the perfusion medium within a range of 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; or 2-4 ng/ml. As provided herein, for example, cells were perfused overnight with medium containing 10 ng/ml of IFN-g and/or TNF-a.

In certain embodiments, after the cells have been sufficiently perfused to reach the target cell concentration, perfusion is continued with cytokine-containing medium, but the rate of perfusion is adjusted to maintain homeostasis of one or more other parameters, for example glucose concentration, pH, dissolved oxygen concentration, or the like.

Cells that May be Exposed to Cytokine Treatment and Sources Thereof

In certain embodiments, the cells exposed to cytokine treatment are placenta-derived adherent cells, which may be, in more specific embodiments, adherent stromal cells. Except where indicated otherwise herein, the terms "placenta", "placental tissue", and the like refer to any portion of the placenta. Placenta-derived adherent cells may be obtained, in various embodiments, from either fetal or, in other embodiments, maternal regions of the placenta, or in other embodiments, from both regions; or the cells may be substantially entirely fetal cells, or maternal cells; enriched for fetal cells, or maternal cells; or predominantly fetal cells, or predominantly maternal cells. More specific embodiments of maternal sources are the decidua basalis and the decidua parietalis. More specific embodiments of fetal sources are the amnion, the chorion, and the villi. In certain embodiments, tissue specimens are washed in a physiological buffer [e.g., phosphate-buffered saline (PBS) or Hank's buffer]. Single-cell suspensions can be made, in other embodiments, by treating the tissue with a digestive enzyme (see below) or/and physical disruption, a non-limiting example of which is mincing and flushing the tissue parts through a nylon filter or by gentle pipetting (Falcon, Becton, Dickinson, San Jose, Calif.) with washing medium. In some embodiments, the tissue treatment includes use of a DNAse, a non-limiting example of which is Benzonase from Merck.

In other embodiments, at least 50%, at least 60%, at least 70%, at least 75%, at least 80%, at least 85%, at least 90%, at least 92%, at least 95%, at least 96%, at least 97%, at least 98%, at least 99%, at least 99.5%, at least 99.7%, or at least 99.9% of the cells that are subsequently exposed to cytokine treatment are maternally-derived cells. In yet other embodiments, at least 50%, at least 60%, at least 70%, at least 75%, at least 80%, at least 85%, at least 90%, at least 92%, at least 95%, at least 96%, at least 97%, at least 98%, at least 99%, at least 99.5%, at least 99.7%, or at least 99.9% of the described cells are fetal cells. While maternally-derived cells are generally exemplified herein, it is also contemplated to perform the same or similar procedures and methods with fetal cells, for example full-term placental-derived fetal cells.

Placental cells may be obtained, in various embodiments, from a full-term or pre-term placenta. "Full-term" placenta in this regard refers to a placenta whose gestational age is at least 36 weeks. In some embodiments, residual blood is removed from the placenta before cell harvest. This may be done by a variety of methods known to those skilled in the art, for example by perfusion. The term "perfuse" or "perfusion" as used herein refers to the act of pouring or passing a fluid over or through an organ or tissue. In certain embodiments, the placental tissue may be from any mammal, while in other embodiments, the placental tissue is human. A convenient source of placental tissue is a post-partum placenta (e.g., less than 10 hours after birth); however, a variety of sources of placental tissue or cells may be contemplated by the skilled person. In other embodiments, the placenta is used within 8 hours, within 6 hours, within 5 hours, within 4 hours, within 3 hours, within 2 hours, or within 1 hour of birth. In certain embodiments, the placenta is kept chilled prior to harvest of the cells. In other embodiments, prepartum placental tissue is used. Such tissue may be obtained, for example, from a chorionic villus sampling or by other methods known in the art. Once placental cells are obtained, they are, in certain embodiments, allowed to adhere to an adherent material (e.g., configured as a surface) to thereby isolate adherent cells. In some embodiments, the donor is 35 years old or younger, while in other embodiments, the donor may be any woman of childbearing age.

ASC can be propagated, in some embodiments, by using a combination of 2D and 3D culturing conditions. Conditions for propagating adherent stromal cells in 2D and 3D culture are further described hereinbelow and in the Examples section which follows.

As mentioned, in some embodiments the source of the ASC is a non-fetal source, for example maternal cells from the placenta or somatic tissue from a pediatric or adult donor, for example adipose tissue, bone marrow, peripheral blood, umbilical cord blood, synovial fluid, synovial membranes, and ligaments such as the periodontal ligament. Those skilled in the art will appreciate in light of the present disclosure that ASC may be extracted from various body tissues, using standard techniques such as physical and/or enzymatic tissue disruption, in some embodiments followed by marker-based cell sorting, and then may be subjected to the culturing methods described herein.

As mentioned, the ASC are, in some embodiments, derived from adipose tissue. The phrase "adipose tissue" refers to a connective tissue that comprises fat cells (adipocytes). Adipose tissue-derived adherent stromal cells may be extracted, in various embodiments, by a variety of methods known to those skilled in the art, for example those described in U.S. Pat. No. 6,153,432, which is incorporated herein by reference. The adipose tissue may be derived, in other embodiments, from omental/visceral, mammary, gonadal, or other adipose tissue sites. In some embodiments, the adipose can be isolated by liposuction.

In other embodiments, ASC may be derived from adipose tissue by treating the tissue with a digestive enzyme (non-limiting examples of which are collagenase, trypsin, dispase, hyaluronidase or DNAse); and ethylenediaminetetra-acetic acid (EDTA). The cells may be, in some embodiments, subjected to physical disruption, for example using a nylon or cheesecloth mesh filter. In other embodiments, the cells are subjected to differential centrifugation directly in media or over a Ficoll™ or Percoll™ or other particulate gradient (see U.S. Pat. No. 7,078,230, which is incorporated herein by reference).

In certain embodiments, the ASC that are subsequently exposed to cytokine treatment are mesenchymal stromal cells (MSC). These cells may, in some embodiments, be isolated from many adult tissues, such as placenta, bone marrow and adipose. In further embodiments, the cells are human MSC as defined by The Mesenchymal and Tissue Stem Cell Committee of the International Society for Cellular Therapy (Dominici et al, 2006), based on the following 3 criteria: 1. Plastic-adherence when maintained in standard culture conditions (a minimal essential medium plus 20% fetal bovine serum (FBS)). 2. Expression of the surface molecules CD105, CD73 and CD90, and lack of expression of CD45, CD34, CD14 or CD1 b, CD79a or CD19 and HLA-DR. 3. Differentiation into osteoblasts, adipocytes and chondroblasts in vitro. In some embodiments, the cells are bone marrow (BM)-derived MSC, in more specific embodiments human BM-derived MSC.

Alternatively or in addition, the ASC that are subsequently exposed to cytokine treatment are mesenchymal-like ASC, which exhibit a marker pattern similar to "classical" MSC, but do not differentiate into osteocytes, under conditions where "classical" MSC would differentiate into osteocytes. In other embodiments, the cells exhibit a marker pattern similar to MSC, but do not differentiate into adipocytes, under conditions where MSC would differentiate into adipocytes. In still other embodiments, the cells exhibit a marker pattern similar to MSC, but do not differentiate into either osteocytes or adipocytes, under conditions where MSC would differentiate into osteocytes or adipocytes, respectively. The MSC used for comparison in these assays are, in one embodiment, MSC that have been harvested from BM and cultured in 2D culture. In other embodiments, the MSC used for comparison have been harvested from BM and cultured in 2D culture, followed by 3D culture.

Alternatively or additionally, the ASC that are subsequently exposed to cytokine treatment may express a marker or a collection of markers (e.g. surface marker) characteristic of MSC or mesenchymal-like stromal cells. Examples of surface markers include but are not limited to CD105 (UniProtKB Accession No. P17813), CD29 (UniProtKB Accession No. P05556), CD44 (UniProtKB Accession No. P16070), CD73 (UniProtKB Accession No. P21589), and CD90 (UniProtKB Accession No. P04216). Examples of markers expected to be absent from stromal cells are CD3 (UniProtKB Accession Nos. P09693 [gamma chain] P04234 [delta chain], P07766 [epsilon chain], and P20963 [zeta chain]), CD4 (UniProtKB Accession No. P01730), CD34 (UniProtKB Accession No. P28906), CD45 (UniProtKB Accession No. P08575), CD80 (UniProtKB Accession No. P33681), CD19 (UniProtKB Accession No. P15391), CD5 (UniProtKB Accession No. P06127), CD20 (UniProtKB Accession No. P11836), CD11B (UniProtKB Accession No. P11215), CD14 (UniProtKB Accession No. P08571), CD79-alpha (UniProtKB Accession No. B5QTD1), and HLA-DR (UniProtKB Accession Nos. P04233 [gamma chain], P01903 [alpha chain], and P01911 [beta chain]). All UniProtKB entries mentioned in this paragraph were accessed on Jul. 7, 2014. Those skilled in the art will appreciate that the presence of complex antigens such as CD3 and HLA-DR may be detected by antibodies recognizing any of their component parts, such as, but not limited to, those described herein.

In certain embodiments, over 90% of the ASC that are subsequently exposed to cytokine treatment are positive for CD29, CD90, and CD54. In other embodiments, over 85% of the described cells are positive for CD73 and CD105; and over 65% of the described cells are positive for CD49. In yet other embodiments, less than 1% of the described cells are positive for CD14, CD19, CD31, CD34, CD39, CD45, HLA-DR, and GlyA (Glycophorin A; CD235A; Uniprot Accession No P02724); less than 3% of the cells are positive for CD200; less than 6% of the cells are positive for GlyA; and less than 20% of the cells are positive for SSEA4. In more specific embodiments, over 90% of the described cells are positive for CD29, CD90, and CD54; over 85% of the cells are positive for CD73 and CD105; and over 65% of the cells are positive for CD49. In still other embodiments, over 90% of the described cells are positive for CD29, CD90, and CD54; over 85% of the cells are positive for CD73 and CD105; over 65% of the cells are positive for CD49; less than 1% of the cells are positive for CD14, CD19, CD31, CD34, CD39, CD45, HLA-DR, GlyA; less than 3% of the cells are positive for CD200; less than 6% of the cells are positive for GlyA; and less than 20% of the cells are positive for SSEA4. "Positive" expression of a marker indicates a value higher than the range of the main peak of an isotype control histogram; this term is synonymous herein with characterizing a cell as "express"/"expressing" a marker. "Negative" expression of a marker indicates a value falling within the range of the main peak of an isotype control histogram; this term is synonymous herein with characterizing a cell as "not express"/"not expressing" a marker.

In other embodiments, each of CD73, CD29, and CD105 is expressed by more than 90% of the ASC that are subsequently exposed to cytokine treatment. In still other embodiments, each of CD44, CD73, CD29, and CD105 is expressed by more than 90% of the cells. In yet other embodiments, each of CD34, CD45, CD19, CD14 and HLA-DR is expressed by less than 3% of the cells. In other embodiments, each of CD73, CD29, and CD105 is expressed by more than 90% of the cells, and each of CD34, CD45, CD19, CD14 and HLA-DR is expressed by less than 3% of the cells. In other embodiments, each of CD44, CD73, CD29, and CD105 is expressed by more than 90% of the cells, and each of CD34, CD45, CD19, CD14 and HLA-DR is expressed by less than 3% of the cells.

In other embodiments, each of CD73, CD29, and CD105 is expressed by more than 90% of the ASC that are subsequently exposed to cytokine treatment; and the cells do not differentiate into osteocytes, after incubation for 17 days with a solution containing 0.1 mcM dexamethasone, 0.2 mM ascorbic acid, and 10 mM glycerol-2-phosphate, in plates coated with vitronectin and collagen. In yet other embodiments, each of CD34, CD45, CD19, CD14 and HLA-DR is expressed by less than 3% of the cells; and the cells do not differentiate into osteocytes, after incubation under the aforementioned conditions. In other embodiments, each of CD73, CD29, and CD105 is expressed by more than 90% of the cells, and of CD34, CD45, CD19, CD14 and HLA-DR is expressed by less than 3% of the cells; and the cells do not differentiate into osteocytes, after incubation under the aforementioned conditions. In still other embodiments, the conditions are incubation for 26 days with a solution containing 10 mcM dexamethasone, 0.2 mM ascorbic acid, 10 mM glycerol-2-phosphate, and 10 nM Vitamin D, in plates coated with vitronectin and collagen. The aforementioned solutions will typically contain cell culture medium such as DMEM+10% serum or the like, as will be appreciated by those skilled in the art.

In other embodiments, each of CD73, CD29, and CD105 is expressed by more than 90% of the ASC that are subsequently exposed to cytokine treatment; and the cells do not differentiate into adipocytes, after incubation in adipogenesis induction medium, namely a solution containing 1 mcM dexamethasone, 0.5 mM 3-Isobutyl-1-methylxanthine (IBMX), 10 mcg/ml insulin, and 100 mcM indomethacin, on days 1, 3, 5, 9, 11, 13, 17, 19, and 21; and replacement of the medium with adipogenesis maintenance medium, namely a solution containing 10 mcg/ml insulin, on days 7 and 15, for a total of 25 days. In yet other embodiments, each of CD34, CD45, CD19, CD14 and HLA-DR is expressed by less than 3% of the cells; and the cells do not differentiate into adipocytes, after incubation under the aforementioned conditions. In other embodiments, each of CD73, CD29, and CD105 is expressed by more than 90% of the cells, each of CD34, CD45, CD19, CD14 and HLA-DR is expressed by less than 3% of the cells; and the cells do not differentiate into adipocytes, after incubation under the aforementioned conditions. In still other embodiments, a modified adipogenesis induction medium, containing 1 mcM dexamethasone, 0.5 mM IBMX, 10 mcg/ml insulin, and 200 mcM indomethacin is used, and the incubation is for a total of 26 days. The aforementioned solutions will typically contain cell culture medium such as DMEM+10% serum or the like, as will be appreciated by those skilled in the art.

Alternatively or in addition, the ASC that are subsequently exposed to cytokine treatment express the marker D7-fib. Antibodies against D7-fib are commercially available from Acris Antibodies, Herford, Germany.

In more specific embodiments, greater than 50%, in other embodiments greater than 55%, in other embodiments greater than 60%, in other embodiments greater than 65%, in other embodiments greater than 70%, in other embodiments greater than 75%, in other embodiments greater than 80%, in other embodiments greater than 85%, in other embodiments greater than 90%, in other embodiments greater than 95%, in other embodiments greater than 96%, in other embodiments greater than 97%, in other embodiments greater than 98%, in other embodiments greater than 99% of the ASC that are subsequently exposed to cytokine treatment express a marker selected from CD73, CD90, CD29, and CD105, or in other embodiments 2 or more of these markers, or in other embodiments 3 or more of these markers, or in other embodiments all four of these markers.

According to some embodiments, the ASC that are subsequently exposed to cytokine treatment express CD200, or, in other embodiments, lack expression thereof. In still other embodiments, less than 30%, 25%, 20%, 15%, 10%, 8%, 6%, 5%, 4%, 3%, or 2%, 1%, or 0.5% of the adherent cells express CD200. In yet other embodiments, greater than 70%, 75%, 80%, 85%, 90%, 92%, 94%, 95%, 96%, 97%, 98%, 99%, or 99.5% of the adherent cells express CD200.

According to some embodiments, greater than 50% of the ASC that are subsequently exposed to cytokine treatment do not express a marker selected from CD3, CD4, CD45, CD80, HLA-DR, CD11b, CD14, CD19, CD34, and CD79-alpha, or in other embodiments 2 or more of these markers, or in other embodiments 3 or more of these markers, or in other embodiments 4 or more of these markers, or in other embodiments 5 or more of these markers, or in other embodiments 6 or more of these markers, or in other embodiments 7 or more of these markers, or in other embodiments 8 or more of these markers, or in other embodiments 9 or more of these markers, or in other embodiments all ten of these markers. In other embodiments greater than 60%, in other embodiments greater than 65%, in other embodiments greater than 70%, in other embodiments greater than 75%, in other embodiments greater than 80%, in other embodiments greater than 85%, in other embodiments greater than 90%, in other embodiments greater than 95%, in other embodiments greater than 96%, in other embodiments greater than 97%, in other embodiments greater than 98%, in other embodiments greater than 99% of the ASC that are subsequently exposed to cytokine treatment possess one of the aforementioned characteristics.

In certain embodiments, the ASC that are subsequently exposed to cytokine treatment express or secrete (as appropriate for each protein) c-kit ligand/stem cell factor (SCF; Uniprot Accession no. P21583, Receptor-type tyrosine-protein kinase FLT3 (Flt-3; Uniprot Accession no. P36888), and/or Aldehyde dehydrogenase X (ALDH X; Uniprot Accession no. P30837), each of which represents a separate embodiment. In more specific embodiments, greater than 50%, in other embodiments greater than 55%, in other embodiments greater than 60%, in other embodiments greater than 65%, in other embodiments greater than 70%, in other embodiments greater than 75%, in other embodiments greater than 80%, in other embodiments greater than 85%, in other embodiments greater than 90%, in other embodiments greater than 95%, in other embodiments greater than 96%, in other embodiments greater than 97%, in other embodiments greater than 98%, in other embodiments greater than 99% of the cells express or secrete at least one, in other embodiments at least 2, in other embodiments at least 3, in other embodiments all four of the aforementioned proteins. In other embodiments, the cells have been incubated in a 3D culture, and they collectively express at least 2, 3, 4, 5, 6, 7, 8, 9, 10, 11, or even 12 fold higher of at least one of these proteins than that expressed or secreted by ASC of the same cell type (e.g. placenta, adipose tissue, or bone marrow) incubated in a 2D culture only Additionally or alternatively, the ASC that are subsequently exposed to cytokine treatment secrete or express IL-6 (UniProt identifier P05231), eukaryotic translation elongation factor 2 (EEEF2), reticulocalbin 3, EF-hand calcium binding domain ($RCN_2$), and/or calponin 1 basic smooth muscle (CNN1). In more specific embodiments, greater than 50%, in other embodiments greater than 55%, in other embodiments greater than 60%, in other embodiments greater than 65%, in other embodiments greater than 70%, in other embodiments greater than 75%, in other embodiments greater than 80%, in other embodiments greater than 85%, in other embodiments greater than 90%, in other embodiments greater than 95%, in other embodiments greater than 96%, in other embodiments greater than 97%, in other embodiments greater than 98%, in other embodiments greater than 99%, of the cells express or secrete at least one, in other embodiments at least 2, in other embodiments at least 3, in other embodiments at least 4, in other embodiments all five of the aforementioned proteins. A cell is said to express or secrete a protein or factor if the presence of protein or factor is detectable by standard methods, an example of which is a detectable signal using fluorescence-activated cell sorting (FACS), relative to an isotype control.

Additionally or alternatively, the ASC that are subsequently exposed to cytokine treatment express low or undetectable amounts of heterogeneous nuclear ribonucleoprotein H1 (Hnrph1), CD44 antigen isoform 2 precursor, 3 phosphoadenosine 5 phosphosulfate synthase 2 isoform a (Papss2), and/or ribosomal protein L7a (rpL7a). In more specific embodiments, greater than 50%, in other embodiments greater than 55%, in other embodiments greater than 60%, in other embodiments greater than 65%, in other embodiments greater than 70%, in other embodiments greater than 75%, in other embodiments greater than 80%, in other embodiments greater than 85%, in other embodiments greater than 90%, in other embodiments greater than 95%, in other embodiments greater than 96%, in other embodiments greater than 97%, in other embodiments greater than 98%, of the cells do not express or secrete at least one, in other embodiments at least 2, in other embodiments at least 3, in other embodiments all four of the aforementioned proteins.

In still other embodiments, the cells that are subsequently exposed to cytokine treatment are a placental cell population that is a mixture of fetal and maternal cells. In more specific embodiments, the mixture contains 20-80% fetal cells; 30-80% fetal cells; 40-80% fetal cells; 50-80% fetal cells; 60-80% fetal cells; 20-90% fetal cells; 30-90% fetal cells; 40-90% fetal cells; 50-90% fetal cells; 60-90% fetal cells; 20-80% maternal cells; 30-80% maternal cells; 40-80% maternal cells; 50-80% maternal cells; 60-80% maternal cells; 20-90% maternal cells; 30-90% maternal cells; 40-90% maternal cells; 50-90% maternal cells; or 60-90% maternal cells.

In still other embodiments, the cells that are subsequently exposed to cytokine treatment may be allogeneic, or in other embodiments, the cells may be autologous. In other embodiments, the cells may be fresh or, in other embodiments, frozen (e.g., cryopreserved).

Additional Method Characteristics

In certain embodiments, the described method further comprises the subsequent step (following the described 3D incubation with pro-inflammatory cytokines) of harvesting the ASC by removing the ASC from the 3D culture apparatus. In more particular embodiments, cells may be removed from a 3D matrix while the matrix remains within the bioreactor.

Alternatively or in addition, the described ASC have been incubated in a 2D adherent-cell culture apparatus, in certain embodiments, prior to the 3D culturing steps. In some embodiments, cells (which have been extracted, in some embodiments, from placenta, from adipose tissue, etc.) are then subjected to prior step of incubation in a 2D adherent-cell culture apparatus, followed by the described 3D culturing steps.

In certain embodiments, at least part of the aforementioned step (a) is performed in perfusion mode. In other embodiments, the majority of step (a) (the majority of the 3D culturing time in the absence of inflammatory cytokines) is performed in perfusion mode. In still other embodiments, all of step (a) is performed in perfusion mode. In other embodiments, at least part of step (a) is performed in batch mode.

Alternatively or in addition, at least part of step (b) is performed in batch mode. In other embodiments, the majority of step (b) (the majority of the 3D culturing time in the presence of inflammatory cytokines) is performed in batch mode. In still other embodiments, all of step (b) is performed in batch mode. In other embodiments, at least part of step (b) is performed in perfusion mode. In yet other embodiments, at least the majority of step (a) is performed in perfusion mode, and at least the majority of step (b) is performed in batch mode.

In various embodiments, "an adherent material" refers to a material that is synthetic, or in other embodiments naturally occurring, or in other embodiments a combination thereof. In certain embodiments, the material is non-cytotoxic (or, in other embodiments, is biologically compatible). Alternatively or in addition, the material is fibrous, which may be, in more specific embodiments, a woven fibrous matrix, a non-woven fibrous matrix, or either. In still other embodiments, the material exhibits a chemical structure such as charged surface exposed groups, which allows cell adhesion. Non-limiting examples of adherent materials which may be used in accordance with this aspect include a polyester, a polypropylene, a polyalkylene, a polyfluorochloroethylene, a polyvinyl chloride, a polystyrene, a polysulfone, a cellulose acetate, a glass fiber, a ceramic particle, a poly-L-lactic acid, and an inert metal fiber. Other embodiments include Matrigel™, an extra-cellular matrix component (e.g., Fibronectin, Chondronectin, Laminin), and a collagen. In more particular embodiments, the material may be selected from a polyester and a polypropylene. Non-limiting examples of synthetic adherent materials include polyesters, polypropylenes, polyalkylenes, polyfluorochloroethylenes, polyvinyl chlorides, polystyrenes, polysulfones, cellulose acetates, and poly-L-lactic acids, glass fibers, ceramic particles, and an inert metal fiber, or, in more specific embodiments, polyesters, polypropylenes, polyalkylenes, polyfluorochloroethylenes, polyvinyl chlorides, polystyrenes, polysulfones, cellulose acetates, and poly-L-lactic acids.

In other embodiments, the aforementioned step (a) (incubation in the absence of inflammatory cytokines) is performed for at least 3 days, at least 4 days, at least 5 days, at least 6 days, or at least 7 days. In other embodiments, step (a) is performed for between 3-4 days, 3-5 days, 3-6 days, 3-7 days, 4-5 days, 4-6 days, 4-7 days, 5-6 days, 5-7 days, or 6-7 days. In still other embodiments, step (a) is performed for at least 1 population doubling, at least 2 doublings, at least 3 doublings, at least 4 doublings, 1-2 doublings, 1-3 doublings, 1-4 doublings, 2-3 doublings, 2-4 doublings, or 3-4 doublings. In some embodiments, step (a) is 3D incubation.

Alternatively or in addition, the aforementioned step (b) (3D incubation in the presence of inflammatory cytokines) is performed for between 6-48 hours (hr), 8-48 hr, 10-48 hr, 12-48 hr, 14-48 hr, 16-48 hr, 20-48 hr, 6-36 hr, 8-36 hr, 10-36 hr, 12-36 hr, 14-36 hr, 16-36 hr, 20-36 hr, 24-36 hr, 28-36 hr, 6-24 hr, 8-24 hr, 10-24 hr, 12-24 hr, 14-24 hr, 16-24 hr, 20-24 hr, 8-18 hr, 10-18 hr, 12-18 hr, or 14-18 hr. In certain embodiments, step (b) is performed for 16-28 hr, 16-26 hr, 18-28 hr, 18-26 hr, 20-26 hr, 22-26 hr, 23-25 hr, about 24 hr, or 24 hr. As provided herein, cytokine incubation of significantly less than 40 hr, for example for 18-28 hr, 20-28 hr, 18-26 hr, or 20-26 hr, resulted in enhanced cell viability.

Alternatively or in addition, step (b) is performed in a bioreactor, which is, in more specific embodiments, a packed-bed bioreactor. In some embodiments, the bioreactor comprises a container for holding medium, and a control apparatus, for controlling pH, temperature, and oxygen levels and optionally other parameters. In more specific embodiments, the bioreactor also contains a 3D substrate. Alternatively or in addition, the bioreactor contains ports for the inflow and outflow of fresh medium and gases.

In certain embodiments, the bioreactor is connected to an external medium reservoir (e.g. that is used to perfuse the bioreactor) containing the desired concentration of cytokines. Alternatively or in addition, the medium in the bioreactor is spiked with one or more cytokines at the beginning of the cytokine incubation, in order to rapidly bring the cytokine concentration in the bioreactor to the desired concentration. As provided herein, spiking of the bioreactor medium enabled a reduced incubation time in the presence of cytokines, resulting in enhanced cell viability. In other embodiments, step (b) comprises the sub-steps of (i) adding a bolus of the pro-inflammatory cytokine(s) to a medium in the bioreactor, thereby generating a growth medium containing inflammatory cytokines; and (ii) operably connecting the growth medium in the bioreactor with an external reservoir comprising an additional amount of growth medium containing inflammatory cytokines.

The term packed-bed bioreactor, except where indicated otherwise, refers to a bioreactor in which the cellular growth substrate is not ordinarily lifted from the bottom of the incubation vessel in the presence of growth medium. For example, the substrate may have sufficient density to prevent being lifted and/or it may be packed by mechanical pressure to present it from being lifted. The substrate may be either a single body or multiple bodies. Typically, the substrate remains substantially in place during the standard perfusion rate of the bioreactor. In certain embodiments, the definition does not exclude that the substrate may be lifted at unusually fast perfusion rates, for example greater than 200 rpm.

In still other embodiments, which may be, in some embodiments, combined with the previous embodiments of incubation length and spiking, step (b) is begun when the culture is in exponential growth phase. In more specific embodiments, step (b) is begun when the culture is in the latter half of exponential growth phase. In some embodiments, the culture is still in exponential growth phase at the conclusion of step (b). In other embodiments, the culture is in late exponential growth phase at the conclusion of step (b). In some embodiments, the cells are in a bioreactor, which is, in more specific embodiments, a packed-bed bioreactor. As provided herein, cytokine treatment of ASC in exponential phase produces cells with a protein expression profile.

Figure 16:
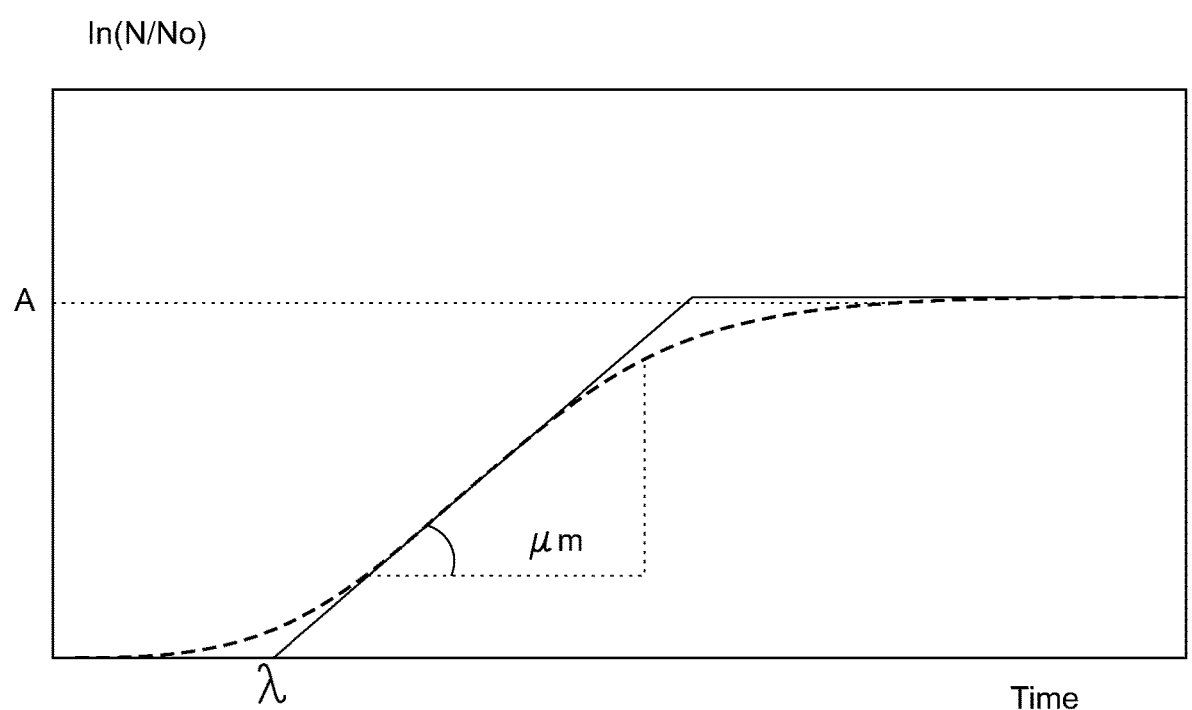
FIG. 16 is a theoretical plot, provided for illustrative purposes only, of the logarithm of the relative population size of a cell culture against time. $\mu_m$ is the maximal cell division rate, X denotes the end of stationary phase, and A is the asymptote.

The terms "exponential phase" and "exponential growth phase", except where indicated otherwise, refer to a time period in which the rate of cell division is at or near the maximal value for the particular system, where the rate of cell division is expressed as the logarithm of the relative population size ($\ln(N/N0)$, where N=the number of cells, and N0=the number of cells at the time of inoculation). In a more specific definition, the rate of cell division is at least 70% of the maximal cell division rate. The maximal cell division rate may be defined as the slope of a tangent line of a plot of the logarithm of the relative population size against time. A theoretical plot, provided for illustrative purposes only, is shown in FIG. 16.

Those skilled in the art will appreciate that, when cells are seeded into a culture system (for example, a bioreactor), there is often a lag phase, during which cell division is relatively slow. The end of lag phase may be mathematically defined as the X-axis intercept of the aforementioned tangent line. The lag phase is followed by exponential phase. When environmental factors become limiting, the cell division rate begins to appreciably slow. For example, the cell division rate may slow to less than 60% of its maximal value. This phase is sometimes referred to as "late exponential phase" or "late exponential growth phase". In a more specific definition, the rate of cell division during late exponential growth phase is at between 30%-60% of the maximal cell division rate. Finally, the culture reaches stationary phase, where there is no appreciable net increase in cell number.

In still other embodiments, step (a) is performed for 3-7 days, and step (b) is performed for 12-48 hours; step (a) is performed for 3-6 days, and step (b) is performed for 12-48 hours; step (a) is performed for 4-7 days, and step (b) is performed for 12-48 hours; step (a) is performed for 4-6 days, and step (b) is performed for 12-48 hours; step (a) is performed for 3-7 days, and step (b) is performed for 12-36 hours; step (a) is performed for 3-6 days, and step (b) is performed for 12-36 hours; step (a) is performed for 4-7 days, and step (b) is performed for 12-36 hours; step (a) is performed for 4-6 days, and step (b) is performed for 12-36 hours; step (a) is performed for 3-7 days, and step (b) is performed for 16-36 hours; step (a) is performed for 3-6 days, and step (b) is performed for 16-36 hours; step (a) is performed for 4-7 days, and step (b) is performed for 16-36 hours; step (a) is performed for 4-6 days, and step (b) is performed for 16-36 hours; step (a) is performed for 3-7 days, and step (b) is performed for 16-36 hours; step (a) is performed for 3-6 days, and step (b) is performed for 16-36 hours; step (a) is performed for 4-7 days, and step (b) is performed for 16-36 hours; or step (a) is performed for 4-6 days, and step (b) is performed for 16-36 hours. In other embodiments, step (a) is performed for 4-7 days, and step (b) is performed for 16-28 hours, 16-26 hours, 18-28 hours, 18-26 hours, 20-26 hours, 22-26 hours, 23-25 hours, about 24 hours, or 24 hours. In still other embodiments, step (a) is performed for 4-6 days, and step (b) is performed for 16-28 hours, 16-26 hours, 18-28 hours, 18-26 hours, 20-26 hours, 22-26 hours, 23-25 hours, about 24 hours, or 24 hours.

According to other embodiments, the described 3D culturing (step (a) and step (b) together) is performed for at least 4 doublings, at least 5 doublings, at least 6 doublings, at least 7 doublings, at least 8 doublings, at least 9 doublings, or at least 10 doublings. In certain embodiments, cells are typically passaged when the culture reaches about 70-90% confluence, typically after 3-5 days (e.g., 1-3 doublings).

In other embodiments, the total length of 3D culturing is at least 4 days; between 4-12 days; in other embodiments between 4-11 days; in other embodiments between 4-10 days; in other embodiments between 4-9 days; in other embodiments between 5-9 days; in other embodiments between 5-8 days; in other embodiments between 6-8 days; or in other embodiments between 5-7 days.

In certain embodiments, 3D culturing can be performed in a bioreactor. In some embodiments, the bioreactor comprises a container for holding medium and a 3D attachment (carrier) substrate disposed therein, and a control apparatus, for controlling pH, temperature, and oxygen levels and optionally other parameters. In more specific embodiments, the 3D substrate is in a packed bed configuration. Alternatively or in addition, the bioreactor contains ports for the inflow and outflow of fresh medium and gases.

Examples of bioreactors include, but are not limited to, a continuous stirred tank bioreactor, a CelliGen® bioreactor system (New Brunswick Scientific (NBS) and a BIOFLO 310 bioreactor system (New Brunswick Scientific (NBS).

As provided herein, a bioreactor is capable, in certain embodiments, of expansion of ASC on a 3D substrate under controlled conditions (e.g. pH, temperature and oxygen levels) and with growth medium perfusion, which in some embodiments is constant perfusion and in other embodiments is adjusted in order to maintain target levels of glucose or other components. Furthermore, the cell cultures can be directly monitored for concentrations of glucose, lactate, glutamine, glutamate and ammonium. The glucose consumption rate and the lactate formation rate of the adherent cells enable, in some embodiments, measurement of cell growth rate and determination of the harvest time.

In some embodiments, a continuous stirred tank bioreactor is used, where a culture medium is continuously fed into the bioreactor and a product is continuously drawn out, to maintain a time-constant steady state within the reactor. A stirred tank bioreactor with a fibrous bed basket is available for example from New Brunswick Scientific Co., Edison, N.J.). Additional bioreactors that may be used, in some embodiments, are stationary-bed bioreactors; and air-lift bioreactors, where air is typically fed into the bottom of a central draught tube flowing up while forming bubbles, and disengaging exhaust gas at the top of the column. Additional possibilities are cell-seeding perfusion bioreactors with polyactive foams [as described in Wendt, D. et al., Biotechnol Bioeng 84: 205-214, (2003)] and radial-flow perfusion bioreactors containing tubular poly-L-lactic acid (PLLA) porous scaffolds [as described in Kitagawa et al., Biotechnology and Bioengineering 93(5): 947-954 (2006). Other bioreactors which can be used are described in U.S. Pat. Nos. 6,277,151; 6,197,575; 6,139,578; 6,132,463; 5,902,741; and 5,629,186, which are incorporated herein by reference.

Another exemplary bioreactor, the CelliGen 310 Bioreactor, is depicted in FIG. 1. In the depicted embodiment, A Fibrous-Bed Basket (16) is loaded with polyester disks (10). In some embodiments, the vessel is filled with deionized water or isotonic buffer via an external port (1 [this port may also be used, in other embodiments, for cell harvesting]) and then optionally autoclaved. In other embodiments, following sterilization, the liquid is replaced with growth medium, which saturates the disk bed as depicted in (9). In still further embodiments, temperature, pH, dissolved oxygen concentration, etc., are set prior to inoculation. In yet further embodiments, a slow stirring initial rate is used to promote cell attachment, then agitation is increased. Alternatively or addition, perfusion is initiated by adding fresh medium via an external port (2). If desired, metabolic products may be harvested from the cell-free medium above the basket (8). In some embodiments, rotation of the impeller creates negative pressure in the draft-tube (18), which pulls cell-free effluent from a reservoir (15) through the draft tube, then through an impeller port (19), thus causing medium to circulate (12) uniformly in a continuous loop. In still further embodiments, adjustment of a tube (6) controls the liquid level; an external opening (4) of this tube is used in some embodiments for harvesting. In other embodiments, a ring sparger (not visible), is located inside the impeller aeration chamber (11), for oxygenating the medium flowing through the impeller, via gases added from an external port (3), which may be kept inside a housing (5), and a sparger line (7). Alternatively or in addition, sparged gas confined to the remote chamber is absorbed by the nutrient medium, which washes over the immobilized cells. In still other embodiments, a water jacket (17) is present, with ports for moving the jacket water in (13) and out (14).

In certain embodiments, a perfused bioreactor is used, wherein the perfusion chamber contains carriers. The carriers may be, in more specific embodiments, selected from macrocarriers, microcarriers, or either. Non-limiting examples of microcarriers that are available commercially include alginate-based (GEM, Global Cell Solutions), dextran-based (Cytodex®, GE Healthcare), collagen-based (Cultispher®, Percell Biolytica), and polystyrene-based (SoloHill Engineering) microcarriers. In certain embodiments, the microcarriers are packed inside the perfused bioreactor.

In some embodiments, the carriers in the perfused bioreactor are packed, for example forming a packed bed, which is submerged in a nutrient medium. Alternatively or in addition, the carriers may comprise an adherent material. In other embodiments, the surface of the carriers comprises an adherent material, or the surface of the carriers is adherent. In still other embodiments, the material exhibits a chemical structure such as charged surface exposed groups, which allows cell adhesion. Non-limiting examples of adherent materials which may be used in accordance with this aspect include a polyester, a polypropylene, a polyalkylene, a polyfluorochloroethylene, a polyvinyl chloride, a polystyrene, a polysulfone, a cellulose acetate, a glass fiber, a ceramic particle, a poly-L-lactic acid, and an inert metal fiber. In more particular embodiments, the material may be selected from a polyester and a polypropylene. In various embodiments, an "adherent material" refers to a material that is synthetic, or in other embodiments naturally occurring, or in other embodiments a combination thereof. In certain embodiments, the material is non-cytotoxic (or, in other embodiments, is biologically compatible). Non-limiting examples of synthetic adherent materials include polyesters, polypropylenes, polyalkylenes, polyfluorochloroethylenes, polyvinyl chlorides, polystyrenes, polysulfones, cellulose acetates, and poly-L-lactic acids, glass fibers, ceramic particles, and an inert metal fiber, or, in more specific embodiments, polyesters, polypropylenes, polyalkylenes, polyfluorochloroethylenes, polyvinyl chlorides, polystyrenes, polysulfones, cellulose acetates, and poly-L-lactic acids. Other embodiments include Matrigel™, an extra-cellular matrix component (e.g., Fibronectin, Chondronectin, Laminin), and a collagen.

Alternatively or in addition, the adherent material is fibrous, which may be, in more specific embodiments, a woven fibrous matrix, a non-woven fibrous matrix, or either. In still other embodiments, the material exhibits a chemical structure such as charged surface groups, which allows cell adhesion, e.g. polyesters, polypropylenes, polyalkylenes, polyfluorochloroethylenes, polyvinyl chlorides, polystyrenes, polysulfones, cellulose acetates, and poly-L-lactic acids. In more particular embodiments, the material may be selected from a polyester and a polypropylene.

Alternatively or in addition, the carriers comprise a fibrous material, optionally an adherent, fibrous material, which may be, in more specific embodiments, a woven fibrous matrix, a non-woven fibrous matrix, or either. Non-limiting examples of fibrous carriers are New Brunswick Scientific Fibracel® carriers, available commercially from of Eppendorf AG, Germany, and made of polyester and polypropylene; and BioNOC II carriers, available commercially from CESCO BioProducts (Atlanta, Ga.) and made of PET (polyethylene terephthalate). In certain embodiments, the referred-to fibrous matrix comprises a polyester, a polypropylene, a polyalkylene, a polyfluorochloroethylene, a polyvinyl chloride, a polystyrene, or a polysulfone. In more particular embodiments, the fibrous matrix is selected from a polyester and a polypropylene.

In other embodiments, cells are produced using a packed-bed spinner flask. In more specific embodiments, the packed bed may comprise a spinner flask and a magnetic stirrer. The spinner flask may be fitted, in some embodiments, with a packed bed apparatus, which may be, in more specific embodiments, a fibrous matrix; a non-woven fibrous matrix; non-woven fibrous matrix comprising polyester; or a non-woven fibrous matrix comprising at least about 50% polyester. In more specific embodiments, the matrix may be similar to the CelliGen™ Plug Flow bioreactor which is, in certain embodiments, packed with Fibra-Cel® (or, in other embodiments, other carriers). The spinner is, in certain embodiments, batch fed (or in other alternative embodiments fed by perfusion), fitted with one or more sterilizing filters, and placed in a tissue culture incubator. In further embodiments, cells are seeded onto the scaffold by suspending them in medium and introducing the medium to the apparatus. In still further embodiments, the agitation speed is gradually increased, for example by starting at 40 RPM for 4 hours, then gradually increasing the speed to 120 RPM. In certain embodiments, the glucose level of the medium may be tested periodically (i.e. daily), and the perfusion speed adjusted maintain an acceptable glucose concentration, which is, in certain embodiments, between 400-700 mg\liter, between 450-650 mg\liter, between 475-625 mg\liter, between 500-600 mg\liter, or between 525-575 mg\liter. In yet other embodiments, at the end of the culture process, the carriers are removed from the packed bed and, in some embodiments, washed with isotonic buffer, and the cells are processed or removed from the carriers by agitation and/or enzymatic digestion.

In certain embodiments, the bioreactor is seeded at a concentration of between 10,000-2,000,000 cells/ml of medium, in other embodiments 20,000-2,000,000 cells/ml, in other embodiments 30,000-1,500,000 cells/ml, in other embodiments 40,000-1,400,000 cells/ml, in other embodiments 50,000-1,300,000 cells/ml, in other embodiments 60,000-1,200,000 cells/ml, in other embodiments 70,000-1,100,000 cells/ml, in other embodiments 80,000-1,000,000 cells/ml, in other embodiments 80,000-900,000 cells/ml, in other embodiments 80,000-800,000 cells/ml, in other embodiments 80,000-700,000 cells/ml, in other embodiments 80,000-600,000 cells/ml, in other embodiments 80,000-500,000 cells/ml, in other embodiments 80,000-400,000 cells/ml, in other embodiments 90,000-300,000 cells/ml, in other embodiments 90,000-250,000 cells/ml, in other embodiments 90,000-200,000 cells/ml, in other embodiments 100,000-200,000 cells/ml, in other embodiments 110,000-1,900,000 cells/ml, in other embodiments 120,000-1,800,000 cells/ml, in other embodiments 130,000-1,700,000 cells/ml, in other embodiments 140,000-1,600,000 cells/ml.

In still other embodiments, between $1\text{-}20 \times 10^6$ cells per gram (gr) of carrier (substrate) are seeded, or in other embodiments $1.5\text{-}20 \times 10^6$ cells/gr carrier, or in other embodiments $1.5\text{-}18 \times 10^6$ cells/gr carrier, or in other embodiments $1.8\text{-}18 \times 10^6$ cells/gr carrier, or in other embodiments $2\text{-}18 \times 10^6$ cells/gr carrier, or in other embodiments $3\text{-}18 \times 10^6$ cells/gr carrier, or in other embodiments $2.5\text{-}15 \times 10^6$ cells/gr carrier, or in other embodiments $3\text{-}15 \times 10^6$ cells/gr carrier, or in other embodiments $3\text{-}14 \times 10^6$ cells/gr carrier, or in other embodiments $3\text{-}12 \times 10^6$ cells/gr carrier, or in other embodiments $3.5\text{-}12 \times 10^6$ cells/gr carrier, or in other embodiments $3\text{-}10 \times 10^6$ cells/gr carrier, or in other embodiments $3\text{-}9 \times 10^6$ cells/gr carrier, or in other embodiments $4\text{-}9 \times 10^6$ cells/gr carrier, or in other embodiments $4\text{-}8 \times 10^6$ cells/gr carrier, or in other embodiments $4\text{-}7 \times 10^6$ cells/gr carrier, or in other embodiments $4.5\text{-}6.5 \times 10^6$ cells/gr carrier.

In certain embodiments, the harvest from the bioreactor is performed when at least about 10%, in other embodiments at least 12%, in other embodiments at least 14%, in other embodiments at least 16%, in other embodiments at least 18%, in other embodiments at least 20%, in other embodiments at least 22%, in other embodiments at least 24%, in other embodiments at least 26%, in other embodiments at least 28%, or in other embodiments at least 30%, of the cells are in the S and G2/M phases (collectively), as can be assayed by various methods known in the art, for example FACS detection. Typically, in the case of FACS, the percentage of cells in S and G2/M phase is expressed as the percentage of the live cells, after gating for live cells, for example using a forward scatter/side scatter gate. Those skilled in the art will appreciate that the percentage of cells in these phases correlates with the percentage of proliferating cells.

In other embodiments, incubation of ASC may comprise microcarriers, which may, in certain embodiments, be inside a bioreactor. Microcarriers are well known to those skilled in the art, and are described, for example in U.S. Pat. Nos.

8,828,720, 7,531,334, 5,006,467, which are incorporated herein by reference. Microcarriers are also commercially available, for example as Cytodex™ (available from Pharmacia Fine Chemicals, Inc.) Superbeads (commercially available from Flow Labs, Inc.), and as DE-52 and DE-53 (commercially available from Whatman, Inc.). In certain embodiments, the ASC may be incubated in a 2D apparatus, for example tissue culture plates or dishes, prior to incubation in microcarriers. In other embodiments, the ASC are not incubated in a 2D apparatus prior to incubation in microcarriers. In certain embodiments, the microcarriers are packed inside a bioreactor.

In certain embodiments, further steps of purification or enrichment for ASC may be performed. Such methods include, but are not limited to, cell sorting using markers for ASC and/or, in various embodiments, MSC or mesenchymal-like stromal cells.

Cell sorting, in this context, refers to any procedure, whether manual, automated, etc., that selects cells on the basis of their expression of one or more markers, their lack of expression of one or more markers, or a combination thereof. Those skilled in the art will appreciate that data from one or more markers can be used individually or in combination in the sorting process. In other embodiments, the described incubation of ASC comprises microcarriers, which may, in certain embodiments, be inside a bioreactor. Microcarriers are well known to those skilled in the art, and are described, for example in U.S. Pat. Nos. 8,828,720, 7,531,334, 5,006,467, which are incorporated herein by reference. Microcarriers are also commercially available, for example as Cytodex™ (available from Pharmacia Fine Chemicals, Inc.) Superbeads (commercially available from Flow Labs, Inc.), and as DE-52 and DE-53 (commercially available from Whatman, Inc.). In certain embodiments, the ASC may be incubated in a 2D apparatus, for example tissue culture plates or dishes, prior to incubation in microcarriers. In other embodiments, the ASC are not incubated in a 2D apparatus prior to incubation in microcarriers. In certain embodiments, the microcarriers are packed inside a bioreactor.

Figure 17A:
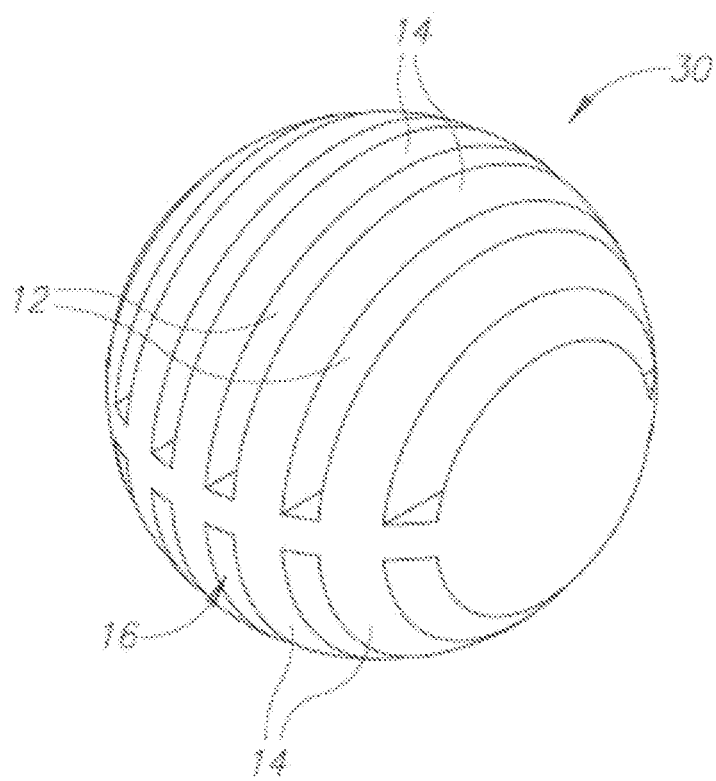
FIG. 17A is a perspective view of a carrier (or "3D body"), according to an exemplary embodiment. B is a perspective view of a carrier, according to another exemplary embodiment. C is a cross-sectional view of a carrier, according to an exemplary embodiment.
Figure 17B:
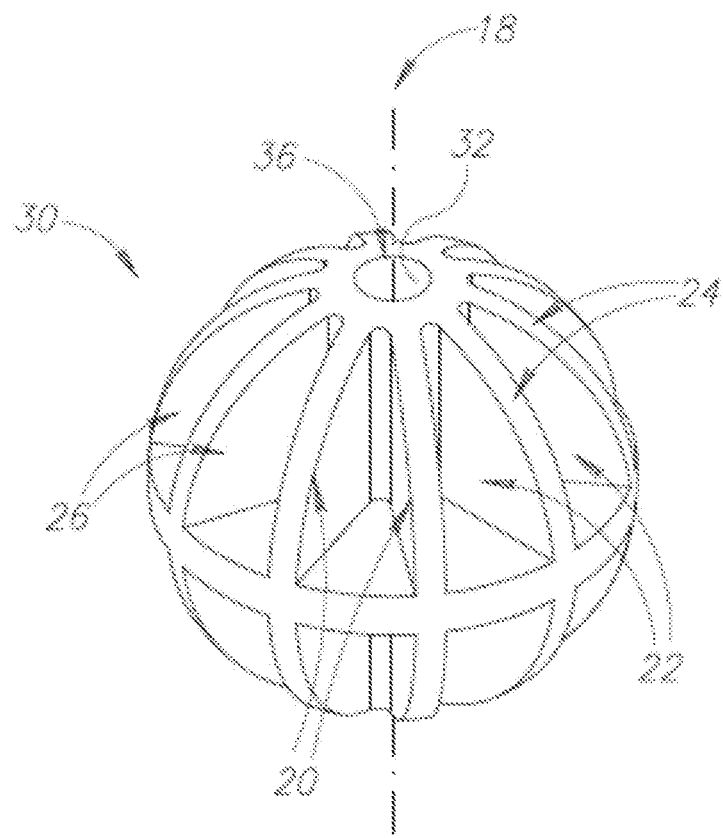

In some embodiments, with reference to FIGS. 17A-B, and as described in WO/2014/037862, published on Mar. 13, 2014, which is incorporated herein by reference in its entirety, grooved carriers 30 are used for proliferation and/or incubation of ASC. In various embodiments, the carriers may be used following a 2D incubation (e.g. on culture plates or dishes), or without a prior 2D incubation. In other embodiments, incubation on the carriers may be followed by incubation on a 3D substrate in a bioreactor, which may be, for example, a packed-bed substrate or microcarriers; or incubation on the carriers may not be followed by incubation on a 3D substrate.

Figure 17C:
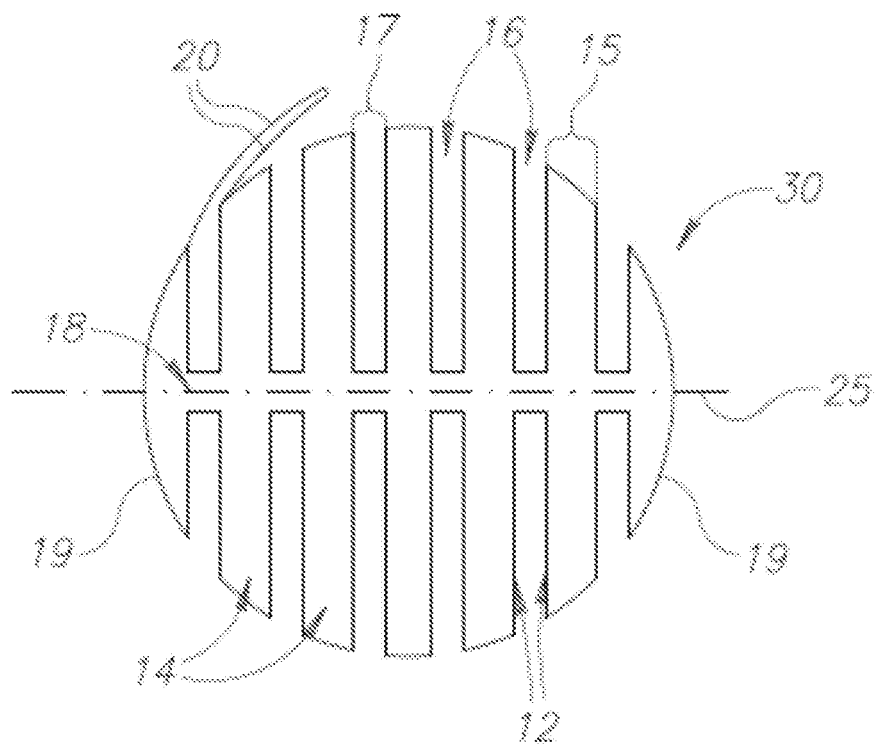

With reference to FIG. 17A, carriers 30 can include multiple two-dimensional (2D) surfaces 12 extending from an exterior of carrier 30 towards an interior of carrier 30. As shown, the surfaces are formed by a group of ribs 14 that are spaced apart to form openings 16, which may be sized to allow flow of cells and culture medium (not shown) during use. With reference to FIG. 17C, carrier 30 can also include multiple 2D surfaces 12 extending from a central carrier axis 18 of carrier 30 and extending generally perpendicular to ribs 14 that are spaced apart to form openings 16, creating multiple 2D surfaces 12. In other embodiments, openings 16 have a cross-sectional shape that is substantially a semicircle arc (see FIG. 17A). In still other embodiments, the central carrier axis 18 is a plane 25 that bisects the sphere, and openings 16 extend from the surface of the carrier to the proximal surface of the plane. In yet other embodiments, openings 16 extend from the surface 20 of the carrier 30 to the proximal surface of the plane and have a cross-sectional shape that is substantially a semicircle arc. In still other embodiments, carrier 30 is substantially spherical and has a largest diameter of 4-10 millimeter (mm), or between 4-9 mm, 4.5-8.5 mm, 5-8 mm, 5.5-7.5 mm, 6-7 mm, 6.1-6.9 mm, 6.2-6.8 mm, 6.3-6.7 mm, 6.4-6.6 mm, or substantially 6.5 mm. In certain embodiments of the aforementioned carrier, ribs 14 are substantially flat and extend parallel to one another. In more specific embodiments, there are 3-7, 4-6, or 5 parallel ribs (not counting the extreme outer ribs 19), forming 6 openings 16 on each side of plane 25. Alternatively or in addition, the width 15 of ribs 14 and the width 17 of openings 16 are such that the ratio of rib width 15 divided by (rib width 15+opening width 17) is between 0.4-0.8, 0.45-0.75, 0.5-0.7, 0.5-0.8, 0.5-0.75, 0.55-0.65, 0.58-0.62, or substantially 0.6.

In other embodiments, carriers 30 are "3D bodies" as described in WO/2014/037862; the contents of which relating to 3D bodies are incorporated herein by reference.

As mentioned, carrier 30 may have a variety of shapes, including but not limited to spherical, cylindrical, cubical, hyperrectangular, ellipsoid, and polyhedral and/or irregular polyhedral shapes. In some embodiments, the diameter of the minimal bounding sphere (e.g. the diameter of the carrier, in the case of a spherical shape) of carrier 30 can range from 1-50 mm. In other embodiments, the outer largest dimension can range from 2-20 mm, from 3-15 mm, or from 4-10 mm. In other embodiments, the generic chord length of carriers 30 ranges from 0.5-25 mm, from 1-10 mm, from 1.5-7.5 mm, from 2-5 mm, or from 2.5-4 mm. As known to those skilled in the art, generic chord length is described inter alia in Li et al, Determination of non-spherical particle size distribution from chord length measurements. Part 1: Theoretical analysis. Chemical Engineering Science 60(12): 3251-3265, 2005)

Depending upon the overall size of carrier 30, ribs 14 and openings 16 can be variously sized. For example, ribs 14 can range in thickness from 0.1-2 mm or from 0.2 mm-1 mm. In particular, ribs 14 can be 0.4-0.6 mm, 0.5-0.7 mm, or 0.6-0.8 mm in thickness. Openings 16 can range in width from 0.01-1 mm or from 0.1-0.5 mm. In particular, openings 16 can be 0.25-0.35 mm, 0.35-0.45 mm, or 0.45-0.55 mm in width.

In preferred embodiments, the carriers provide 2D surfaces for attachment and monolayer growth over at least a majority of or all of the surface area of the multiple 2D surfaces 12, 22. Alternatively or in addition, the carriers have a surface area to volume ratio that is between 3-1000 cm2/cm3, between 3-500 cm2/cm3, between 3-300 cm2/cm3, between 3-200 cm2/cm3, between 3-100 cm2/cm3, between 3-50 cm2/cm3, between 3-30 cm2/cm3, between 5-20 cm2/cm3, or between 10-15 cm2/cm3.

As shown in FIGS. 17A-B, in various embodiments, carriers 30 may be substantially spherical and have a diameter that forms the carriers' largest dimension. In some embodiments, a diameter of carrier 30 can range from 1-50 mm. In other embodiments, the diameter can range from 2-20 mm, 3-15, mm, or 4-10 mm. With reference to FIG. 17B, depending upon the overall size of carrier 30, ribs 24 and openings 26 can be variously sized. For example, ribs 24 can range in thickness from 0.1-2 mm or from 0.2-1 mm. In particular, ribs 24 can be 0.45-0.55 mm, 0.55-0.65 mm, or 0.65-0.75 mm in thickness. In some embodiments, a minimum width of openings 26 can range from 0.01-1 mm, from 0.05-0.8 mm, or from 0.1-0.5 mm. Specifically, the minimum width of openings 26 can be 0.25-0.35 mm, 0.3.5-0.45 mm, or 0.45-0.55 mm. In other embodiments, the largest cross-sectional dimension of opening 26 can range from 0.1-5 mm, from 0.2-3 mm, or from 0.5-2 mm. More particularly, opening 26 can have a largest cross-sectional dimension of 0.7.5-0.85 mm, 0.95-1.05 mm, or 1.15-0.25 mm. Further, carrier 30 includes an opening 36 extending through the carrier's center and forming additional surfaces 32, which can support monolayer growth of eukaryotic cells.

In the embodiment shown in FIG. 17A, ribs 14 are substantially flat and extend parallel to one another. In other embodiments, the ribs are in other configurations. For example, FIG. 17B illustrates carrier 30 having multiple two-dimensional surfaces 22 formed by ribs 24 in a different configuration. In particular, ribs 24 are shaped to form openings 26 that are spaced around the circumference of carrier 30, whereby openings 26 can be generally wedge shaped. Ribs 24 can extend generally radially from a central carrier axis 18 of carrier 30 to a peripheral surface of carrier 30. Carrier 30 can also include one or more lateral planes extending from the central carrier axis 18 of carrier 30 and extending generally perpendicular to ribs 24, as depicted in FIG. 17C, which is a cross-sectional view of certain embodiments of the carrier 30 of FIG. 17A.

In still other embodiments, the material forming the multiple 2D surfaces comprises at least one polymer. In more specific embodiments, the polymer is selected from a polyamide, a polycarbonate, a polysulfone, a polyester, a polyacetal, and polyvinyl chloride.

The material used to produce the described carriers can include, in various embodiments, metals (e.g. titanium), metal oxides (e.g., titanium oxide films), glass, borosilicate, carbon fibers, ceramics, biodegradable materials (e.g. collagen, gelatin, PEG, hydrogels), and or polymers. Suitable polymers may include polyamides, such as GRILAMID® TR 55 (EMS-Grivory, Sumter, S.C.); polycarbonates such as LEXAN® (Sabic, Pittsfield, Mass.) and Macrolon® (Bayer); polysulfones such as RADEL® PPSU (Solvay) and UDEL® PSU (Solvay); polyesters such as TRITAN® (Polyone), Celanex® (polybutylene terephthalate), Crastin® (polybutylene terephthalate), and PBT® HX312C; polyacetals such as CELON® (Ticana), and polyvinyl chloride. In certain embodiments, the described carriers are composed of a non-porous material, or, if pores are present, they are no larger than 20 microns, in other embodiments 10 microns, in other embodiments 5 microns, in other embodiments 3 microns, in other embodiments 2 microns, or in other embodiments 1 micron.

In more specific embodiments, cell-culture carriers are formed of injection-molded surface treatment of LEXAN® or GRILAMID®, with a smooth surface texture, using growth medium proteins and/or polylysine on LEXAN® or GRILAMID® carriers; cell-culture carriers formed of injection-molded GRILAMID® with a rough surface that was preincubated with growth medium proteins. In other embodiments, untreated LEXAN® or GRILAMID® surfaces are utilized.

In other embodiments, at least part of the carriers may be formed using a polystyrene polymer. The polystyrene may be further modified using corona discharge, gas-plasma (roller bottles and culture tubes), or other similar processes. These processes can generate highly energetic oxygen ions which graft onto the surface polystyrene chains so that the surface becomes hydrophilic and negatively charged when medium is added. Furthermore, any of the carriers may be produced at least in part from combinations of materials. Materials of the carriers can be further coated or treated to support cell attachment. Such coating and/or pretreatment may include use of collagen I, collagen IV, gelatin, poly-d-lysine, fibronectin, laminin, amine, and carboxyl.

In various embodiments, the described carriers are coated with one or more coatings. Suitable coatings may, in some embodiments, be selected to control cell attachment or parameters of cell biology. Suitable coatings may include, for example, peptides, proteins, carbohydrates, nucleic acid, lipids, polysaccharides, glycosaminoglycans, proteoglycans, hormones, extracellular matrix molecules, cell adhesion molecules, natural polymers, enzymes, antibodies, antigens, polynucleotides, growth factors, synthetic polymers, polylysine, drugs and/or other molecules or combinations or fragments of these.

Furthermore, in various embodiments, the surfaces of the carriers described herein may be treated or otherwise altered to control cell attachment and or other biologic properties. Options for treating the surfaces include chemical treatment, plasma treatment, and/or corona treatment. Further, in various embodiments, the materials may be treated to introduce functional groups into or onto the material, including groups containing hydrocarbons, oxygen, and/or nitrogen. In addition, in various embodiments, the material may be produced or altered to have a texture to facilitate settling of cells or control other cell properties. For example, in some embodiments, the materials used to produce the cell-culture carriers have a roughness on a nanometer or micrometer scale that facilitates settling of cells and/or controls other cell properties.

Harvesting

In still other embodiments, the described modified ASC have been harvested from the bioreactor by a process comprising vibration or agitation, for example as described in PCT International Application Publ. No. WO 2012/140519, which is incorporated herein by reference. In certain embodiments, during harvesting, the cells are agitated at 0.7-6 Hertz, or in other embodiments 1-3 Hertz, during, or in other embodiments during and after, treatment with a protease, optionally also comprising a calcium chelator. In certain embodiments, the carriers containing the cells are agitated at 0.7-6 Hertz, or in other embodiments 1-3 Hertz, while submerged in a solution or medium comprising a protease, optionally also comprising a calcium chelator. Non-limiting examples of a protease plus a calcium chelator are trypsin, or another enzyme with similar activity, optionally in combination with another enzyme, non-limiting examples of which are Collagenase Types I, II, III, and IV, with EDTA. Enzymes with similar activity to trypsin are well known in the art; non-limiting examples are TrypLE™, a fungal trypsin-like protease, and Collagenase, Types I, II, III, and IV, which are available commercially from Life Technologies. Enzymes with similar activity to collagenase are well known in the art; non-limiting examples are Dispase I and Dispase II, which are available commercially from Sigma-Aldrich. In still other embodiments, the cells are harvested by a process comprising an optional wash step, followed by incubation with collagenase, followed by incubation with trypsin. In various embodiments, at least one, at least two, or all three of the aforementioned steps comprise agitation. In more specific embodiments, the total duration of agitation during and/or after treatment with protease plus a calcium chelator is between 2-10 minutes, in other embodiments between 3-9 minutes, in other embodiments between 3-8 minutes, and in still other embodiments between 3-7 minutes. In still other embodiments, the cells are subjected to agitation at 0.7-6 Hertz, or in other embodiments 1-3 Hertz, during the wash step before the protease and calcium chelator are added.

Those skilled in the art will appreciate that a variety of isotonic buffers may be used for washing cells and similar uses. Hank's Balanced Salt Solution (HBSS; Life Technologies) is only one of many buffers that may be used.

Non-limiting examples of base media useful in 2D and 3D culturing include Minimum Essential Medium Eagle, ADC-1, LPM (Bovine Serum Albumin-free), F10(HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. In certain embodiments, DMEM is used. These and other useful media are available from GIBCO, Grand Island, N.Y., USA and Biological Industries, Bet HaEmek, Israel, among others.

In some embodiments, the base medium may be supplemented with additional substances. Non-limiting examples of such substances are serum, which is, in some embodiments, fetal serum of cows or other species, which is, in some embodiments, 5-15% of the medium volume. In certain embodiments, the medium contains 1-5%, 2-5%, 3-5%, 1-10%, 2-10%, 3-10%, 4-15%, 5-14%, 6-14%, 6-13%, 7-13%, 8-12%, 8-13%, 9-12%, 9-11%, or 9.5%-10.5% serum, which may be FBS, or in other embodiments another animal serum. In still other embodiments, the medium is serum-free.

Alternatively or in addition, the base medium may be supplemented by growth factors, vitamins (e.g. ascorbic acid), salts (e.g. B-glycerophosphate), steroids (e.g. dexamethasone) and hormones e.g., growth hormone, erythropoietin, thrombopoietin, macrophage colony stimulating factor, c-kit ligand/stem cell factor, osteoprotegerin ligand, insulin, insulin-like growth factor, epidermal growth factor, fibroblast growth factor, nerve growth factor, ciliary neurotrophic factor, platelet-derived growth factor, and bone morphogenetic protein.

It will be appreciated that additional components may be added to the culture medium. Such components may be antibiotics, antimycotics, albumin, amino acids, and other components known to the art for the culture of cells.

The various media described herein, i.e. the 2D growth medium, if applicable, the first 3D growth medium, and the second 3D growth medium, may be independently selected from each of the described embodiments relating to medium composition. In certain embodiments, the only difference between the first and second 3D growth media is the presence of the added cytokines. In other embodiments, the first and second 3D growth media differ in other respects. In various embodiments, any medium suitable for growth of cells in a bioreactor may be used.

It will also be appreciated that in certain embodiments, when the described ASC are intended for administration to a human subject, the cells and the culture medium (e.g., with the above described medium additives) are substantially xeno-free, i.e., devoid of any animal contaminants e.g., mycoplasma. For example, the culture medium can be supplemented with a serum-replacement, human serum and/or synthetic or recombinantly produced factors.

Characteristics of Cytokine-Treated Cells

In some embodiments, the cells that have been treated with cytokines (hereinafter: "cytokine-treated cells") cells do not differentiate into osteocytes, under conditions where "classical" mesenchymal stem cells would differentiate into osteocytes. In some embodiments, the conditions are incubation with a solution containing 0.1 micromolar (mcM) dexamethasone, 0.2 mM ascorbic acid, and 10 mM glycerol-2-phosphate, in plates coated with vitronectin and collagen, for 17 days. In still other embodiments, the conditions are incubation with a solution containing 10 mcM dexamethasone, 0.2 mM ascorbic acid, 10 mM glycerol-2-phosphate, and 10 nM Vitamin D, in plates coated with vitronectin and collagen, for 26 days. The aforementioned solutions will typically contain cell culture medium such as DMEM+10% serum or the like, as will be appreciated by those skilled in the art.

As mentioned, in other embodiments, the described cytokine-treated cells do not differentiate into adipocytes, under conditions where mesenchymal stem cells would differentiate into adipocytes. In some embodiments, as provided herein, the conditions are incubation of adipogenesis induction medium, namely a solution containing 1 mcM dexamethasone, 0.5 mM 3-Isobutyl-1-methylxanthine (IBMX), 10 mcg/ml insulin, and 100 mcM indomethacin, added on days 1, 3, 5, 9, 11, 13, 17, 19, and 21, while the medium is replaced with adipogenesis maintenance medium, namely a solution containing 10 mcg/ml insulin, on days 7 and 15, for a total of 25 days. In still other embodiments, as provided herein, a modified adipogenesis induction medium, containing 1 mcM dexamethasone, 0.5 mM IBMX, 10 mcg/ml insulin, and 200 mcM indomethacin is used, and the incubation is for a total of 26 days. The aforementioned solutions will typically contain cell culture medium such as DMEM+10% serum or the like, as will be appreciated by those skilled in the art.

In certain embodiments, in vitro, the described cytokine-treated ASC stimulate endothelial cell proliferation (ECP), or in another embodiment inhibit T cell proliferation, or in another embodiment perform both activities. In other embodiments, in vivo, the cells stimulate angiogenesis, or in another embodiment exhibit immunosuppressive activity (in some embodiments, particularly for T cell responses), and or in another embodiment support hematopoietic stem cell (HSC) engraftment, or in other embodiments any 2 of the above in vivo characteristics, or in other embodiments all 3 of the above in vivo characteristics. Each combination is considered to be a separate embodiment. In certain embodiments, as provided herein, when 750 human umbilical cord endothelial cells (HUVEC) are incubated for 4 days under normoxic conditions at 37° C. on a layer of the ASC, proliferation of the HUVEC cells is enhanced, for example at least 120%, at least 125%, at least 130%, at least 140%, at least 150%, and least 160%, or at least 180% of the level observed in the absence of ASC.

According to some embodiments, the described cytokine-treated ASC are capable of suppressing an immune reaction in the subject. Methods of determining the immunosuppressive capability of a cell population are well known to those skilled in the art. For example, a mixed lymphocyte reaction (MLR) may be performed. In an exemplary, non-limiting MLR assay, cord blood (CB) mononuclear cells, for example human cells or cells from another species, are incubated with irradiated cord blood cells (iCB), peripheral blood-derived monocytes (PBMC; for example human PBMC or PBMC from another species), in the presence or absence of a cell population to be tested. CB cell replication, which correlates with the intensity of the immune response, can be measured by a variety of methods known in the art, for example by $^3$H-thymidine uptake. Reduction of the CB cell replication when co-incubated with test cells indicates an immunosuppressive capability. Alternatively, a similar assay can be performed with peripheral blood (PB)-derived MNC, in place of CB cells. Alternatively or in addition, secretion of pro-inflammatory and anti-inflammatory cytokines by blood cell populations (such as CB cells or PBMC) can be measured when stimulated (for example by incubation with non-matched cells, or with a non-specific stimulant such as PHA), in the presence or absence of the ASC. In certain embodiments, for example in the case of human ASC, as provided herein, when 150,000 of the ASC are co-incubated for 48 hours with 50,000 allogeneic PBMC, followed by a 5-hour stimulation with 1.5 mcg of LPS, the amount of IL-10 secretion by the PBMC is enhanced, for example at least 120%, at least 130%, at least 150%, at least 170%, at least 200%, or at least 300% of the amount observed with LPS stimulation in the absence of ASC.

In other embodiments, each of CD73, CD29, and CD105 is expressed by more than 90% of the described cytokine-treated cells; and the cells do not differentiate into osteocytes, after incubation for 17 days with a solution containing 0.1 mcM dexamethasone, 0.2 mM ascorbic acid, and 10 mM glycerol-2-phosphate, in plates coated with vitronectin and collagen. In yet other embodiments, each of CD34, CD19, and CD14 is expressed by less than 3% of the cells; and the cells do not differentiate into osteocytes, after incubation under the aforementioned conditions. In other embodiments, each of CD73, CD29, and CD105 is expressed by more than 90% of the cells, and of CD34, CD19, and CD14 is expressed by less than 3% of the cells; and the cells do not differentiate into osteocytes, after incubation under the aforementioned conditions. In still other embodiments, the conditions are incubation for 26 days with a solution containing 10 mcM dexamethasone, 0.2 mM ascorbic acid, 10 mM glycerol-2-phosphate, and 10 nM Vitamin D, in plates coated with vitronectin and collagen. The aforementioned solutions will typically contain cell culture medium such as DMEM+10% serum or the like, as will be appreciated by those skilled in the art.

In other embodiments, each of CD73, CD29, and CD105 is expressed by more than 90% of the described cytokine-treated cells; and the cells do not differentiate into adipocytes, after incubation in adipogenesis induction medium, namely a solution containing 1 mcM dexamethasone, 0.5 mM IBMX, 10 mcg/ml insulin, and 100 mcM indomethacin, on days 1, 3, 5, 9, 11, 13, 17, 19, and 21; and replacement of the medium with adipogenesis maintenance medium, namely a solution containing 10 mcg/ml insulin, on days 7 and 15, for a total of 25 days. In yet other embodiments, each of CD34, CD19, and CD14 is expressed by less than 3% of the cells; and the cells do not differentiate into adipocytes, after incubation under the aforementioned conditions. In other embodiments, each of CD73, CD29, and CD105 is expressed by more than 90% of the cells, each of CD34, CD19, and CD14 is expressed by less than 3% of the cells; and the cells do not differentiate into adipocytes, after incubation under the aforementioned conditions. In still other embodiments, a modified adipogenesis induction medium, containing 1 mcM dexamethasone, 0.5 mM IBMX, 10 mcg/ml insulin, and 200 mcM indomethacin is used, and the incubation is for a total of 26 days. The aforementioned solutions will typically contain cell culture medium such as DMEM+10% serum or the like, as will be appreciated by those skilled in the art.

In other embodiments, each of CD73, CD29, and CD105 is expressed by more than 90% of the described cytokine-treated cells; and the cells stimulate ECP. In yet other embodiments, each of CD34, CD19, and CD14 is expressed by less than 3% of the cells; and the cells stimulate ECP. In other embodiments, each of CD73, CD29, and CD105 is expressed by more than 90% of the cells, each of CD34, CD19, and CD14 is expressed by less than 3% of the cells; and the cells stimulate ECP.

In other embodiments, each of CD73, CD29, and CD105 is expressed by more than 90% of the described cytokine-treated cells; and the cells inhibit T cell proliferation. In yet other embodiments, each of CD34, CD19, and CD14 is expressed by less than 3% of the cells; and the cells inhibit T cell proliferation. In other embodiments, each of CD73, CD29, and CD105 is expressed by more than 90% of the cells, each of CD34, CD19, and CD14 is expressed by less than 3% of the cells; and the cells inhibit T cell proliferation.

In other embodiments, the described cytokine-treated cells exhibit a spindle shape when cultured in 2D culture.

In still other embodiments, there is provided a culture, comprising cytokine-treated ASC with one of the aforementioned sets of characteristics, or, in other embodiments, a bioreactor comprising the culture. In some embodiments, the bioreactor further comprises a synthetic 3D substrate. In other embodiments is provided a composition, comprising the ASC. In certain embodiments, the composition further comprises a pharmacologically acceptable excipient. In further embodiments, the excipient is a cryoprotectant, or is a carrier protein. Alternatively or in addition, the composition is frozen. In still other embodiments is provided a suspension comprising any of the aforementioned cell populations. In certain embodiments, the suspension comprises a pharmaceutically acceptable excipient. In other embodiments, the suspension is a pharmaceutical composition. In still other embodiments, the suspension is frozen and further comprises, in some embodiments, a cryoprotectant. Each of the aforementioned ASC populations represents a separate embodiment in this regard.

In certain embodiments, the cytokine-treated cells have been transfected with one or more therapeutic factors, which may be, in certain embodiments, pro-angiogenic or anti-inflammatory factors. In other embodiments, the cells have not been transfected with any exogenous genetic material.

In still other embodiments, the cytokine-treated cells are a placental cell population that is a mixture of fetal and maternal cells. In more specific embodiments, the mixture contains 20-80% fetal cells; 30-80% fetal cells; 40-80% fetal cells; 50-80% fetal cells; 60-80% fetal cells; 20-90% fetal cells; 30-90% fetal cells; 40-90% fetal cells; 50-90% fetal cells; 60-90% fetal cells; at least 50% fetal cells; at least 60% fetal cells; at least 70% fetal cells; at least 80% fetal cells; at least 90% fetal cells; at least 95% fetal cells; 20-80% maternal cells; 30-80% maternal cells; 40-80% maternal cells; 50-80% maternal cells; 60-80% maternal cells; 20-90% maternal cells; 30-90% maternal cells; 40-90% maternal cells; 50-90% maternal cells; 60-90% maternal cells; at least 50% maternal cells; at least 60% maternal cells; at least 70% maternal cells; at least 80% maternal cells; at least 90% maternal cells; at least 95% maternal cells. In other embodiments, the cells are substantially entirely fetal cells, or are substantially entirely maternal cells. "Substantially entirely", in this context, refers to a lack of detectable presence of other cell types (maternal or fetal, respectively) by standard fluorescence-activated cell sorting assays.

In other embodiments, the described cells produce or secrete elevated amounts of therapeutic factors, relative to untreated cells. In certain embodiments, the therapeutic factors are anti-inflammatory factors, or, in other embodiments, pro-inflammatory factors, or, in other embodiments, angiogenic factors.

In yet other embodiments is provided a population of ASC, in some embodiments placenta-derived ASC, that secrete elevated levels of Vascular Endothelial Growth Factor (VEGF). In some embodiments, the VEGF secretion is measured after removing the cells from the bioreactor. In certain embodiments, the VEGF secretion is at least 1.5-fold, at least 2-fold, at least 2.5-fold, at least 3-fold, at least 4-fold, or at least 5-fold as high as cells prepared in the absence of added cytokines. In certain embodiments, as provided herein, VEGF secretion is measured by incubating $1 \times 10^6$ ASC for 24 hours under standard conditions, then replacing the medium with EBM-2 medium and incubating for 24 hours under hypoxic conditions (1% 02). In more specific embodiments, at least 180 picrograms (pg), at least 190 pg, at least 200 pg, at least 250 pg, at least 300 pg, at least 400 pg, at least 500 pg, at least 600 pg, at least 800 pg, at least 1000 pg, at least 1200 pg, at least 1500 pg, at least 2000 pg, at least 3000 pg, at least 4000 pg, at least 5000 pg, 50-2000 pg, 75-2000 pg, 100-1500 pg, 150-1400 pg, 200-1400 pg, 250-1300 pg, 300-1200 pg, or 400-1000 pg of VEGF per 24 hours are secreted by the cells under these conditions. In still other embodiments is provided a culture, comprising the VEGF-secreting ASC, or in other embodiments, a bioreactor comprising the culture. In some embodiments, the bioreactor further comprises a synthetic 3D substrate. In other embodiments is provided a composition, comprising the VEGF-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of Interleukin-6 (IL-6; UniProt No. P05231). In some embodiments, the IL-6 secretion is measured after removing the cells from the bioreactor. In certain embodiments, the IL-6 secretion is at least 2-fold, at least 3-fold, at least 4-fold, at least 5-fold, at least 6-fold, or at least 8-fold, or at least 10-fold as high as cells prepared in the absence of added cytokines. In certain embodiments, as provided herein, IL-6 secretion is measured by incubating $1 \times 10^6$ ASC for 24 hours under standard conditions, then replacing the medium with EBM-2 medium and incubating for 24 hours under hypoxic conditions (1% 02) or normoxic conditions (5% 02). In more specific embodiments, at least 20 picrograms (pg), at least 30 pg, at least 50 pg, at least 70 pg, at least 100 pg, at least 150 pg, at least 200 pg, at least 300 pg, at least 400 pg, at least 500 pg, at least 700 pg, at least 1000 pg, at least 2000 pg, 50-2000 pg, 75-2000 pg, 100-1500 pg, 150-1400 pg, 200-1400 pg, 250-1300 pg, 300-1200 pg, 400-1000 pg, 1000-20,000 pg, 1500-18,000 pg, 1700-17,000 pg, 1800-16,000 pg, 1900-15,000 pg, 2000-14,000 pg, 2100-13,000 pg, 2200-14,000 pg, 2300-13,000 pg, 2400-12,000 pg, 2500-10,000 pg, 2500-8,000 pg, 2500-6,000 pg, or 2500-4,000 pg of IL-6 per 24 hours are secreted by the cells under these conditions. In still other embodiments is provided a culture, comprising the IL-6-secreting ASC, or in other embodiments, a bioreactor comprising the culture. In some embodiments, the bioreactor further comprises a synthetic 3D substrate. In other embodiments is provided a composition, comprising the IL-6-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of MCP-1 (Monocyte chemoattractant protein 1; UniProt No. P13500). In some embodiments, as provided herein, MCP-1 secretion is measured during the last day of incubation in the bioreactor. In certain embodiments, the MCP-1 secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In certain embodiments, as provided herein, MCP-1 secretion is measured by incubating $1 \times 10^6$ ASC for 24 hours under standard conditions, then replacing the medium with EBM-2 medium and incubating for 24 hours under normoxic conditions (5% $O_2$). In more specific embodiments, at least 20 pg, at least 30 pg, at least 50 pg, at least 70 pg, at least 100 pg, at least 150 pg, at least 200 pg, at least 300 pg, at least 400 pg, at least 500 pg, at least 700 pg, at least 1000 pg, at least 2000 pg, 50-2000 pg, 75-2000 pg, 100-1500 pg, 150-1400 pg, 200-1400 pg, 250-1300 pg, 300-1200 pg, 400-1000 pg, 1000-20,000 pg, 1500-18,000 pg, 1700-17,000 pg, 1800-16,000 pg, 1900-15,000 pg, 2000-14,000 pg, 2100-13,000 pg, 2200-14,000 pg, 2300-13,000 pg, 2400-12,000 pg, 2500-10,000 pg, 2500-8,000 pg, 2500-6,000 pg, or 2500-4,000 pg of MCP-1 per 24 hours are secreted by the cells under these conditions. In still other embodiments is provided a culture, comprising the MCP-1-secreting ASC, or in other embodiments, a bioreactor comprising the culture. In some embodiments, the bioreactor further comprises a synthetic 3D substrate. In other embodiments is provided a composition, comprising the MCP-1-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of GM-CSF. In some embodiments, as provided herein, GM-CSF secretion is measured during the last day of incubation in the bioreactor. In certain embodiments, the GM-CSF secretion is at least 2-fold, at least 3-fold, at least 4-fold, at least 5-fold, at least 6-fold, or at least 8-fold, at least 10-fold, at least 15-fold, at least 20-fold, or at least 30-fold as high as cells prepared in the absence of added cytokines. In still other embodiments is provided a culture, comprising the GM-CSF-secreting ASC, or in other embodiments, a bioreactor comprising the culture. In some embodiments, the bioreactor further comprises a synthetic 3D substrate. In other embodiments is provided a composition, comprising the GM-CSF-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of RANTES (C-C motif chemokine 5; UniProt No. P13501). In some embodiments, the RANTES secretion is measured after removing the cells from the bioreactor. In certain embodiments, the RANTES secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In certain embodiments, as provided herein, RANTES secretion is measured by incubating $5 \times 10^5$ ASC for 24 hours under standard conditions, then replacing the medium with serum medium and incubating for an additional 24 hours under normoxic conditions. In more specific embodiments, at least 20 pg, at least 30 pg, at least 50 pg, at least 70 pg, at least 100 pg, at least 150 pg, at least 200 pg, at least 300 pg, at least 400 pg, at least 500 pg, at least 700 pg, at least 1000 pg, at least 1500 pg, at least 2000 pg, at least 3000 pg, at least 4000 pg, at least 5000 pg, at least 6000 pg, at least 8000 pg, at least 10,000 pg, at least 15,000 pg, at least 20,000 pg, 1000-20,000 pg, 1500-18,000 pg, 1700-17,000 pg, 1800-16,000 pg, 1900-15,000 pg, 2000-14,000 pg, 2100-13,000 pg, 2200-14,000 pg, 2300-13,000 pg, 2400-12,000 pg, 2500-10,000 pg, 2500-8,000 pg, 2500-6,000 pg, 2500-4,000 pg, 2000-15,000 pg, 2500-14,000 pg, 3000-14,000 pg, 3500-12,000 pg, 4000-10,000 pg, 4500-8,000 pg, 5,000-7,000 pg, 10,000-200,000 pg, 15,000-180,000 pg, 17,000-170,000 pg, 18,000-160,000 pg, 19,000-150,000 pg, 20,000-140,000 pg, 22,000-140,000 pg, 24,000-120,000 pg, 26,000-100,000 pg, 28,000-90,000 pg, 30,000-80,000 pg, 32,000-75,000 pg, 34,000-70,000 pg, 36,000-65,000 pg, 37,000-62,000 pg, 38,000-60,000 pg, 39,000-58,000 pg, 40,000-56,000 pg, 41,000-54,000 pg, 42,000-52,000 pg, 40,000-50,000 pg, 38,000-48,000 pg, or 40,000-46,000 pg, of RANTES per 24 hours are secreted by the cells under these conditions. In still other embodiments is provided a culture, comprising the RANTES-secreting ASC, or in other embodiments, a bioreactor comprising the culture. In some embodiments, the bioreactor further comprises a synthetic 3D substrate. In other embodiments is provided a composition, comprising the RANTES-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of G-CSF (Granulocyte colony-stimulating factor; UniProt No. P09919). In some embodiments, the G-CSF secretion is measured after removing the cells from the bioreactor. In certain embodiments, the G-CSF secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In certain embodiments, as provided herein, G-CSF secretion is measured by incubating $5 \times 10^5$ ASC for 24 hours under standard conditions, then replacing the medium with serum medium and incubating for an additional 24 hours. In more specific embodiments, at least 20 pg, at least 30 pg, at least 50 pg, at least 70 pg, at least 100 pg, at least 150 pg, at least 200 pg, at least 300 pg, at least 400 pg, at least 500 pg, at least 700 pg, at least 1000 pg, at least 1500 pg, at least 2000 pg, 50-2000 pg, 75-2000 pg, 100-1500 pg, 150-1400 pg, 200-1400 pg, 250-1300 pg, 300-1200 pg, or 400-1000 pg of G-CSF per 24 hours are secreted by the cells under these conditions. In still other embodiments is provided a culture, comprising the G-CSF-secreting ASC, or in other embodiments, a bioreactor comprising the culture. In some embodiments, the bioreactor further comprises a synthetic 3D substrate. In other embodiments is provided a composition, comprising the G-CSF-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of IL-8. In some embodiments, the IL-8 secretion is measured after removing the cells from the bioreactor. In certain embodiments, the IL-8 secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In certain embodiments, as provided herein, IL-8 secretion is measured by incubating $5 \times 10^5$ ASC for 24 hours under standard conditions, then replacing the medium with serum medium and incubating for an additional 24 hours. In more specific embodiments, at least 20 pg, at least 30 pg, at least 50 pg, at least 70 pg, at least 100 pg, at least 150 pg, at least 200 pg, at least 300 pg, at least 400 pg, at least 500 pg, at least 700 pg, at least 1000 pg, at least 1500 pg, at least 2000 pg, at least 3000 pg, 50-3000 pg, 75-2500 pg, 100-2200 pg, 150-2000 pg, 200-1800 pg, 250-1600 pg, 300-1500 pg, or 400-1400 pg of IL-8 per 24 hours are secreted by the cells under these conditions. In still other embodiments is provided a culture, comprising the IL-8-secreting ASC, or in other embodiments, a bioreactor comprising the culture. In some embodiments, the bioreactor further comprises a synthetic 3D substrate. In other embodiments is provided a composition, comprising the IL-8-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of IL-15 (Interleukin-15; UniProt No. P40933). In some embodiments, the IL-15 secretion is measured after removing the cells from the bioreactor. In certain embodiments, the IL-15 secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In certain embodiments, as provided herein, IL-15 secretion is measured by incubating $5 \times 10^5$ ASC for 24 hours under standard conditions, then replacing the medium with serum medium and incubating for an additional 24 hours. In more specific embodiments, at least 20 pg, at least 30 pg, at least 50 pg, at least 70 pg, at least 100 pg, at least 150 pg, at least 200 pg, at least 300 pg, at least 400 pg, at least 500 pg, at least 700 pg, at least 1000 pg, at least 1500 pg, at least 2000 pg, 50-2000 pg, 75-2000 pg, 100-1500 pg, 150-1400 pg, 200-1400 pg, 250-1300 pg, 300-1200 pg, or 400-1000 pg of IL-15 per 24 hours are secreted by the cells under these conditions. In still other embodiments is provided a culture, comprising the IL-15-secreting ASC, or in other embodiments, a bioreactor comprising the culture. In some embodiments, the bioreactor further comprises a synthetic 3D substrate. In other embodiments is provided a composition, comprising the IL-15-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of IL-16 (interleukin-16; UniProt No. Q05BE6). In some embodiments, the IL-16 secretion is measured after removing the cells from the bioreactor. In certain embodiments, the IL-16 secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In certain embodiments, as provided herein, IL-16 secretion is measured by incubating $5\times10^5$ ASC for 24 hours under standard conditions, then replacing the medium with serum medium and incubating for an additional 24 hours. In more specific embodiments, at least 20 pg, at least 30 pg, at least 50 pg, at least 70 pg, at least 100 pg, at least 150 pg, at least 200 pg, at least 300 pg, at least 400 pg, at least 500 pg, at least 700 pg, at least 1000 pg, at least 1500 pg, at least 2000 pg, 50-2000 pg, 75-2000 pg, 100-1500 pg, 150-1400 pg, 200-1400 pg, 250-1300 pg, 300-1200 pg, or 400-1000 pg of IL-16 per 24 hours are secreted by the cells under these conditions. In still other embodiments is provided a culture, comprising the IL-16-secreting ASC, or in other embodiments, a bioreactor comprising the culture. In some embodiments, the bioreactor further comprises a synthetic 3D substrate. In other embodiments is provided a composition, comprising the IL-16-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of MIP-1-alpha (C-C motif chemokine 3; UniProt No. P10147). In some embodiments, the MIP-1-alpha secretion is measured after removing the cells from the bioreactor. In certain embodiments, the MIP-1-alpha secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In certain embodiments, as provided herein, MIP-1-alpha secretion is measured by incubating $5\times10^5$ ASC for 24 hours under standard conditions, then replacing the medium with serum medium and incubating for an additional 24 hours under normoxic conditions. In more specific embodiments, at least 20 pg, at least 30 pg, at least 50 pg, at least 70 pg, at least 100 pg, at least 150 pg, at least 200 pg, at least 300 pg, at least 400 pg, at least 500 pg, at least 700 pg, at least 1000 pg, 30-1500 pg, 40-1400 pg, 50-1200 pg, 60-1000 pg, 70-800 pg, 90-700 pg, 100-600 pg, 150-500 pg, or 200-400 pg of MIP-1-alpha per 24 hours are secreted by the cells under these conditions. In still other embodiments is provided a culture, comprising the MIP-1-alpha-secreting ASC, or in other embodiments, a bioreactor comprising the culture. In some embodiments, the bioreactor further comprises a synthetic 3D substrate. In other embodiments is provided a composition, comprising the MIP-1-alpha-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of MIG (C-X-C motif chemokine 9; UniProt No. Q07325). In some embodiments, the MIG secretion is measured after removing the cells from the bioreactor. In certain embodiments, the MIG secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In certain embodiments, as provided herein, MIG secretion is measured by incubating $5\times10^5$ ASC for 24 hours under standard conditions, then replacing the medium with serum medium and incubating for an additional 24 hours under normoxic conditions. In more specific embodiments, at least 20 pg, at least 30 pg, at least 50 pg, at least 70 pg, at least 100 pg, at least 150 pg, at least 200 pg, at least 300 pg, at least 400 pg, at least 500 pg, at least 700 pg, at least 1000 pg, at least 1500 pg, at least 2000 pg, at least 3000 pg, at least 4000 pg, at least 5000 pg, at least 6000 pg, at least 8000 pg, at least 10,000 pg, at least 15,000 pg, at least 20,000 pg, 2000-15,000 pg, 2500-14,000 pg, 3000-14,000 pg, 3500-12,000 pg, 4000-10,000 pg, 4500-8,000 pg, or 5,000-7,000 pg of MIG per 24 hours are secreted by the cells under these conditions. In still other embodiments is provided a culture, comprising the MIG-secreting ASC, or in other embodiments, a bioreactor comprising the culture. In some embodiments, the bioreactor further comprises a synthetic 3D substrate. In other embodiments is provided a composition, comprising the MIG-secreting ASC. In certain embodiments, the composition further comprises a pharmacologically acceptable excipient. In further embodiments, the excipient is a cryoprotectant, or is a carrier protein. Alternatively or in addition, the composition is frozen.

In yet other embodiments is provided a population of ASC, in some embodiments placenta-derived ASC, that secrete elevated levels of ICAM1 (Intercellular Adhesion Molecule 1/CD54; UniProt No. P05362). In some embodiments, the ICAM1 secretion is measured after removing the cells from the bioreactor. In certain embodiments, the ICAM1 secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In certain embodiments, as provided herein, ICAM1 secretion is measured by incubating $5\times10^5$ ASC for 24 hours under standard conditions, then replacing the medium with serum medium and incubating for an additional 24 hours under normoxic conditions. In more specific embodiments, at least 5000 pg, at least 7000 pg, at least 10,000 pg, at least 15,000 pg, at least 20,000 pg, at least 30,000 pg, at least 40,000 pg, at least 50,000 pg, at least 70,000 pg, at least 100,000 pg, at least 150,000 pg, at least 200,000 pg, at least 300,000 pg, at least 400,000 pg, at least 500,000 pg, 20,000-1,500,000 pg, 30,000-1,250,000 pg, 40,000-1,000,000 pg, 50,000-800,000 pg, 70,000-700,000 pg, 100,000-600,000 pg, 150,000-500,000 pg, 200,000-500,000 pg, or 250,000-450,000 pg of ICAM1 per 24 hours are secreted by the cells under these conditions. In still other embodiments is provided a culture, comprising the ICAM1-secreting ASC, or in other embodiments, a bioreactor comprising the culture. In some embodiments, the bioreactor further comprises a synthetic 3D substrate. In other embodiments is provided a composition, comprising the ICAM1-secreting ASC. In certain embodiments, the composition further comprises a pharmacologically acceptable excipient. In further embodiments, the excipient is a cryoprotectant, or is a carrier protein. Alternatively or in addition, the composition is frozen.

As provided herein, the described cells may be incubated under standard conditions to measure their secretion of cytokines or other factors. An example of standard conditions is as follows: $0.5\times10^6$ cells are seeded in a 6-well plate (having a surface area of about 9.5 cm^2) and incubated in 4 milliliter (ml)/well DMEM+10% FBS for 24 hours. The medium is removed and optionally washed with isotonic solution, 1 ml DMEM (without FBS) is added to each well, and the cells are incubated for another 24 hours under normoxic conditions. At the conclusion of this incubation, the medium is removed, and cytokine levels are measured.

In certain embodiments, the cells express or secrete one of the aforementioned cytokines or other proteins and do not differentiate into osteocytes, under conditions where "classical" MSC would differentiate into osteocytes, as described herein. In other embodiments, the cells express or secrete one of the aforementioned cytokines or other proteins and do not differentiate into adipocytes, under conditions where MSC would differentiate into adipocytes, as described herein. In still other embodiments, the cells express or secrete one of the aforementioned cytokines or other proteins and do not differentiate into either osteocytes or adipocytes, under conditions where MSC would differentiate into osteocytes or adipocytes, respectively.

Also provided herein are cell populations produced by the described methods. In certain embodiments, the cell population remains inside the described bioreactor. In other embodiments, the population has been removed ("harvested") from the bioreactor.

In another embodiment is provided a population of cells, wherein most of the population of cells is positive (on a population level) for expression of CD10 (neprilysin; UniProtKB Accession No. P08473), CD29, CD38 (ADP-ribosyl cyclase; UniProtKB Accession No. P28907), and CD40 (UniProtKB Accession No. P25942). Optionally, the majority of the cells also express CD90. Alternatively or in combination, the majority of the cells also express one or more, in other embodiments 2 or more, in other embodiments 3 or more, in other embodiments all 4 of: CD74 (HLA class II histocompatibility antigen gamma chain; UniProtKB Accession No. P04233), CD106 (Vascular cell adhesion protein 1 [VCAM]; UniProtKB Accession No. P19320), CD274 (Programmed cell death 1 ligand 1; UniProtKB Accession No. Q9NZQ7), and HLA-DR. Positivity for marker expression "on a population level" as used herein means that expression of each of the indicated markers is above the indicated threshold level for that particular marker. Alternatively or in combination, the population is at least 40% positive on a population level for one or more, in other embodiments 2 or more, in other embodiments 3 or more, in other embodiments 4 or more, in other embodiments all 5 of: CD42a (Platelet glycoprotein IX; UniProtKB Accession No. P14770), CD45Ra (an isotype of CD45 [Protein tyrosine phosphatase, receptor type, C]; UniProtKB Accession No. P08575), CD77 (Lactosylceramide 4-alpha-galactosyltransferase; UniProtKB Accession No. Q9NPC4), CD243 (Multidrug resistance protein 1; UniProtKB Accession No. P08183), and CD275 (ICOS ligand; UniProtKB Accession No. O75144). In further embodiments, at least 40% of the population is negative for expression of CD9 (UniProtKB Accession No. P21926). In certain embodiments, the population of cells is derived from placental tissue. All UniProtKB entries mentioned in this paragraph were accessed on Jan. 22, 2015. In certain embodiments, the cells express (and/or lack) one of the aforementioned combinations of markers and do not differentiate into osteocytes, under conditions where "classical" MSC would differentiate into osteocytes, as described herein. In other embodiments, the cells express (and/or lack) one of the aforementioned combinations of markers and do not differentiate into adipocytes, under conditions where MSC would differentiate into adipocytes, as described herein. In still other embodiments, the cells express (and/or lack) one of the aforementioned combinations of markers and do not differentiate into either osteocytes or adipocytes, under conditions where MSC would differentiate into osteocytes or adipocytes, respectively.

In another embodiment is provided a population of cells, wherein most of the population of cells is positive, on a population level, for expression of CD10, CD29, CD38, and HLA-DR. Optionally, the majority of the cells also express CD90. Alternatively or in combination, the majority of the cells also express one or more, in other embodiments 2 or more, in other embodiments 3 or more, in other embodiments all 4 of: CD74, CD106, CD274, and CD40. Alternatively or in combination, the population is at least 40% positive on a population level for one or more, in other embodiments 2 or more, in other embodiments 3 or more, in other embodiments 4 or more, in other embodiments all 5 of: CD42a, CD45Ra, CD77, CD243, and CD275. In further embodiments, at least 40% of the population is negative for expression of CD9. In certain embodiments, the population of cells is derived from placental tissue. In certain embodiments, the cells express (and/or lack) one of the aforementioned combinations of markers and do not differentiate into osteocytes, under conditions where "classical" MSC would differentiate into osteocytes, as described herein. In other embodiments, the cells express (and/or lack) one of the aforementioned combinations of markers and do not differentiate into adipocytes, under conditions where MSC would differentiate into adipocytes, as described herein. In still other embodiments, the cells express (and/or lack) one of the aforementioned combinations of markers and do not differentiate into either osteocytes or adipocytes, under conditions where MSC would differentiate into osteocytes or adipocytes, respectively.

In another embodiment is provided a population of cells, wherein most of the population of cells is positive, on a population level, for expression of CD10, CD29, CD38, and CD74. Optionally, the majority of the cells also express CD90. Alternatively or in combination, the majority of the cells also express one or more, in other embodiments 2 or more, in other embodiments 3 or more, in other embodiments all 4 of: HLA-DR, CD106, CD274, and CD40. Alternatively or in combination, the population is at least 40% positive on a population level for one or more, in other embodiments 2 or more, in other embodiments 3 or more, in other embodiments 4 or more, in other embodiments all 5 of: CD42a, CD45Ra, CD77, CD243, and CD275. In further embodiments, at least 40% of the population is negative for expression of CD9. In certain embodiments, the population of cells is derived from placental tissue. In certain embodiments, the cells express (and/or lack) one of the aforementioned combinations of markers and do not differentiate into osteocytes, under conditions where "classical" MSC would differentiate into osteocytes, as described herein. In other embodiments, the cells express (and/or lack) one of the aforementioned combinations of markers and do not differentiate into adipocytes, under conditions where MSC would differentiate into adipocytes, as described herein. In still other embodiments, the cells express (and/or lack) one of the aforementioned combinations of markers and do not differentiate into either osteocytes or adipocytes, under conditions where MSC would differentiate into osteocytes or adipocytes, respectively.

In another embodiment is provided a population of cells, wherein most of the population of cells is positive, on a population level, for expression of CD10, CD29, HLA-DR, and CD74. Optionally, the majority of the cells also express CD90. Alternatively or in combination, the majority of the cells also express one or more, in other embodiments 2 or more, in other embodiments 3 or more, in other embodiments all 4 of: CD38, CD106, CD274, and CD40. Alternatively or in combination, the population is at least 40% positive on a population level for one or more, in other embodiments 2 or more, in other embodiments 3 or more, in other embodiments 4 or more, in other embodiments all 5 of: CD42a, CD45Ra, CD77, CD243, and CD275. In further embodiments, at least 40% of the population is negative for expression of CD9. In certain embodiments, the population of cells is derived from placental tissue. In certain embodiments, the cells express (and/or lack) one of the aforementioned combinations of markers and do not differentiate into osteocytes, under conditions where "classical" MSC would differentiate into osteocytes, as described herein. In other embodiments, the cells express (and/or lack) one of the aforementioned combinations of markers and do not differentiate into adipocytes, under conditions where MSC would differentiate into adipocytes, as described herein. In still other embodiments, the cells express (and/or lack) one of the aforementioned combinations of markers and do not differentiate into either osteocytes or adipocytes, under conditions where MSC would differentiate into osteocytes or adipocytes, respectively.

In another embodiment is provided a population of cells, wherein most of the population of cells is positive, on a population level, for expression of CD10, CD29, HLA-DR, CD38, and CD74. Optionally, the majority of the cells also express CD90. Alternatively or in combination, the majority of the cells also express one or more, in other embodiments 2 or more, in other embodiments all 3 of: CD106, CD274, and CD40. Alternatively or in combination, the population is at least 40% positive on a population level for one or more, in other embodiments 2 or more, in other embodiments 3 or more, in other embodiments 4 or more, in other embodiments all 5 of: CD42a, CD45Ra, CD77, CD243, and CD275. In further embodiments, at least 40% of the population is negative for expression of CD9. In certain embodiments, the population of cells is derived from placental tissue. In certain embodiments, the cells express (and/or lack) one of the aforementioned combinations of markers and do not differentiate into osteocytes, under conditions where "classical" MSC would differentiate into osteocytes, as described herein. In other embodiments, the cells express (and/or lack) one of the aforementioned combinations of markers and do not differentiate into adipocytes, under conditions where MSC would differentiate into adipocytes, as described herein. In still other embodiments, the cells express (and/or lack) one of the aforementioned combinations of markers and do not differentiate into either osteocytes or adipocytes, under conditions where MSC would differentiate into osteocytes or adipocytes, respectively.

In other embodiments, there is provided a population of cells, wherein at least 30%, in other embodiments at least 40%, in other embodiments at least 50%, in other embodiments at least 60%, in other embodiments at least 70%, in other embodiments at least 80%, in other embodiments at least 90% of the cells are positive on an individual level for expression of CD10, CD29, CD38, and CD40. In other embodiments is provided a cell that is positive for expression of CD10, CD29, CD38, and CD40. Optionally, the cell(s) that expresses CD10, CD29, CD38, and CD40 also expresses CD90. Alternatively or in combination, the cell(s) that expresses CD10, CD29, CD38, and CD40 also expresses one or more, in other embodiments 2 or more, in other embodiments 3 or more, in other embodiments all 4 of: CD74, CD106, CD274, and HLA-DR. Alternatively or in combination, the cell(s) that expresses CD10, CD29, CD38, and CD40 also expresses for one or more, in other embodiments 2 or more, in other embodiments 3 or more, in other embodiments 4 or more, in other embodiments all 5 of: CD42a, CD45Ra, CD77, CD243, and CD275. In further embodiments, the cell(s) that expresses CD10, CD29, CD38, and CD40 also does not express expression of CD9. In certain embodiments, the cell(s) is derived from placental tissue. In certain embodiments, the cells express (and/or lack) one of the aforementioned combinations of markers and do not differentiate into osteocytes, under conditions where "classical" MSC would differentiate into osteocytes, as described herein. In other embodiments, the cells express (and/or lack) one of the aforementioned combinations of markers and do not differentiate into adipocytes, under conditions where MSC would differentiate into adipocytes, as described herein. In still other embodiments, the cells express (and/or lack) one of the aforementioned combinations of markers and do not differentiate into either osteocytes or adipocytes, under conditions where MSC would differentiate into osteocytes or adipocytes, respectively.

In other embodiments, there is provided a population of cells, wherein at least 30%, in other embodiments at least 40%, in other embodiments at least 50%, in other embodiments at least 60%, in other embodiments at least 70%, in other embodiments at least 80%, in other embodiments at least 90% of the cells are positive on an individual level for expression of CD10, CD29, CD38, and HLA-DR. In other embodiments is provided a cell that is positive for expression of CD10, CD29, CD38, and HLA-DR. Optionally, the cell(s) that expresses CD10, CD29, CD38, and HLA-DR also expresses CD90. Alternatively or in combination, the cell(s) that expresses CD10, CD29, CD38, and HLA-DR also expresses one or more, in other embodiments 2 or more, in other embodiments 3 or more, in other embodiments all 4 of: CD74, CD106, CD274, and CD40. Alternatively or in combination, the cell(s) that expresses CD10, CD29, CD38, and HLA-DR also expresses one or more, in other embodiments 2 or more, in other embodiments 3 or more, in other embodiments 4 or more, in other embodiments all 5 of: CD42a, CD45Ra, CD77, CD243, and CD275. In further embodiments, the cell(s) that expresses CD10, CD29, CD38, and HLA-DR also does not express CD9. In certain embodiments, the population of cells is derived from placental tissue. In certain embodiments, the cells express (and/or lack) one of the aforementioned combinations of markers and do not differentiate into osteocytes, under conditions where "classical" MSC would differentiate into osteocytes, as described herein. In other embodiments, the cells express (and/or lack) one of the aforementioned combinations of markers and do not differentiate into adipocytes, under conditions where MSC would differentiate into adipocytes, as described herein. In still other embodiments, the cells express (and/or lack) one of the aforementioned combinations of markers and do not differentiate into either osteocytes or adipocytes, under conditions where MSC would differentiate into osteocytes or adipocytes, respectively.

In other embodiments, there is provided a population of cells, wherein at least 30%, in other embodiments at least 40%, in other embodiments at least 50%, in other embodiments at least 60%, in other embodiments at least 70%, in other embodiments at least 80%, in other embodiments at least 90% of the cells are positive on an individual level for expression of CD10, CD29, CD38, and CD74. In other embodiments is provided a cell that is positive for expression of CD10, CD29, CD38, and CD74. Optionally, the cell(s) that expresses CD10, CD29, CD38, and CD74 also expresses CD90. Alternatively or in combination, the cell(s) that expresses CD10, CD29, CD38, and CD74 also expresses one or more, in other embodiments 2 or more, in other embodiments 3 or more, in other embodiments all 4 of: HLA-DR, CD106, CD274, and CD40. Alternatively or in combination, the cell(s) that expresses CD10, CD29, CD38, and CD74 also expresses one or more, in other embodiments 2 or more, in other embodiments 3 or more, in other embodiments 4 or more, in other embodiments all 5 of: CD42a, CD45Ra, CD77, CD243, and CD275. In further embodiments, the cell(s) that expresses CD10, CD29, CD38, and CD74 also does not express CD9. In certain embodiments, the population of cells is derived from placental tissue. In certain embodiments, the cells express (and/or lack) one of the aforementioned combinations of markers and do not differentiate into osteocytes, under conditions where "classical" MSC would differentiate into osteocytes, as described herein. In other embodiments, the cells express (and/or lack) one of the aforementioned combinations of markers and do not differentiate into adipocytes, under conditions where MSC would differentiate into adipocytes, as described herein. In still other embodiments, the cells express (and/or lack) one of the aforementioned combinations of markers and do not differentiate into either osteocytes or adipocytes, under conditions where MSC would differentiate into osteocytes or adipocytes, respectively.

In other embodiments, there is provided a population of cells, wherein at least 30%, in other embodiments at least 40%, in other embodiments at least 50%, in other embodiments at least 60%, in other embodiments at least 70%, in other embodiments at least 80%, in other embodiments at least 90% of the cells are positive on an individual level for expression of CD10, CD29, HLA-DR, and CD74. In other embodiments is provided a cell that is positive for expression of CD10, CD29, HLA-DR, and CD74. Optionally, the cell(s) that expresses CD10, CD29, HLA-DR, and CD74 also expresses CD90. Alternatively or in combination, the cell(s) that expresses CD10, CD29, HLA-DR, and CD74 also expresses one or more, in other embodiments 2 or more, in other embodiments 3 or more, in other embodiments all 4 of: CD38, CD106, CD274, and CD40. Alternatively or in combination, the cell(s) that expresses CD10, CD29, HLA-DR, and CD74 also expresses one or more, in other embodiments 2 or more, in other embodiments 3 or more, in other embodiments 4 or more, in other embodiments all 5 of: CD42a, CD45Ra, CD77, CD243, and CD275. In further embodiments, the cell(s) that expresses CD10, CD29, HLA-DR, and CD74 also does not express CD9. In certain embodiments, the population of cells is derived from placental tissue. In certain embodiments, the cells express (and/or lack) one of the aforementioned combinations of markers and do not differentiate into osteocytes, under conditions where "classical" MSC would differentiate into osteocytes, as described herein. In other embodiments, the cells express (and/or lack) one of the aforementioned combinations of markers and do not differentiate into adipocytes, under conditions where MSC would differentiate into adipocytes, as described herein. In still other embodiments, the cells express (and/or lack) one of the aforementioned combinations of markers and do not differentiate into either osteocytes or adipocytes, under conditions where MSC would differentiate into osteocytes or adipocytes, respectively.

In other embodiment, there is provided a population of cells, wherein at least 30%, in other embodiments at least 40%, in other embodiments at least 50%, in other embodiments at least 60%, in other embodiments at least 70%, in other embodiments at least 80%, in other embodiments at least 90% of the cells are positive on an individual level for expression of CD10, CD29, HLA-DR, CD38, and CD74. In other embodiments is provided a cell that is positive for expression of CD10, CD29, HLA-DR, CD38, and CD74. Optionally, the cell(s) that expresses CD10, CD29, HLA-DR, CD38, and CD74 also expresses CD90. Alternatively or in combination, the cell(s) that expresses CD10, CD29, HLA-DR, CD38, and CD74 also expresses one or more, in other embodiments 2 or more, in other embodiments all 3 of: CD106, CD274, and CD40. Alternatively or in combination, the cell(s) that expresses CD10, CD29, HLA-DR, CD38, and CD74 also expresses one or more, in other embodiments 2 or more, in other embodiments 3 or more, in other embodiments 4 or more, in other embodiments all 5 of: CD42a, CD45Ra, CD77, CD243, and CD275. In further embodiments, the cell(s) that expresses CD10, CD29, HLA-DR, CD38, and CD74 also does not express CD9. In certain embodiments, the population of cells is derived from placental tissue. In certain embodiments, the cells express (and/or lack) one of the aforementioned combinations of markers and do not differentiate into osteocytes, under conditions where "classical" MSC would differentiate into osteocytes, as described herein. In other embodiments, the cells express (and/or lack) one of the aforementioned combinations of markers and do not differentiate into adipocytes, under conditions where MSC would differentiate into adipocytes, as described herein. In still other embodiments, the cells express (and/or lack) one of the aforementioned combinations of markers and do not differentiate into either osteocytes or adipocytes, under conditions where MSC would differentiate into osteocytes or adipocytes, respectively.

In various embodiments, there is provided a culture comprising any of the aforementioned cell populations, or, in other embodiments, a bioreactor, comprising the culture. In some embodiments, the bioreactor further comprises a synthetic three-dimensional substrate. In still other embodiments is provided a suspension comprising any of the aforementioned cell populations. In certain embodiments, the suspension comprises a pharmaceutically acceptable excipient. In other embodiments, the suspension is a pharmaceutical composition. In still other embodiments, the suspension is frozen and further comprises, in some embodiments, a cryoprotectant. In other embodiments is provided a composition, comprising any of the aforementioned cell populations. In certain embodiments, the composition further comprises a pharmacologically acceptable excipient. In further embodiments, the excipient is a cryoprotectant, or is a carrier protein. Alternatively or in addition, the composition is frozen. Each of the aforementioned cell populations represents a separate embodiment in this regard.

Also provided herein are extracellular vesicles, e.g. exosomes, secreted by the described modified ASC. Methods of isolating extracellular vesicles are well known in the art, and include, for example, immuno-magnetic isolation, for example as described in Clayton A et al, 2001; Mathias R A et al, 2009; and Crescitelli R et al, 2013.

In some embodiments, the vesicles are harvested from a bioreactor in which the ASC have been incubated. Alternatively or in addition, the cells are cryopreserved, and then are thawed, after which the vesicles are isolated. In some embodiments, after thawing, the cells are cultured in 2D culture, from which the vesicles are harvested. In certain embodiments, the 2D culture is performed in the presence of inflammatory cytokines, which may be, in various embodiments, any of the cytokines mentioned herein.

Pharmaceutical Compositions

Provided in addition are pharmaceutical compositions, comprising the described modified ASC or cell populations.

In other embodiments are provided pharmaceutical compositions, comprising the described exosomes.

Also provided are conditioned media (CM) derived from the described methods, and, in other embodiments, pharmaceutical compositions comprising the described CM. Those skilled in the art will appreciate that, in certain embodiments, various bioreactors may be used to prepare CM, including but not limited to plug-flow bioreactors, and stationary-bed bioreactors (Kompier R et al. Use of a stationary bed reactor and serum-free medium for the production of recombinant proteins in insect cells. Enzyme Microb Technol. 1991. 13(10):822-7.) For example, CM is produced as a by-product of the described methods for cell expansion. The CM in the bioreactor can be removed from the bioreactor or otherwise isolated. In other embodiments, the described modified ASC are removed from the bioreactor and incubated in another apparatus (a non-limiting example of which is a tissue culture apparatus), and CM from the cells is collected.

The described cells, CM, or exosomes can be, in some embodiments, administered as a part of a pharmaceutical composition that further comprises one or more pharmaceutically acceptable carriers. Hereinafter, the term "pharmaceutically acceptable carrier" refers to a carrier or a diluent. In some embodiments, the carrier or diluent does not cause significant irritation to a subject and does not abrogate the biological activity and properties of the administered cells. Examples, without limitations, of carriers are propylene glycol, saline, emulsions and mixtures of organic solvents with water. In some embodiments, the pharmaceutical carrier is an aqueous solution of saline. In other embodiments, the composition further comprises a pharmacologically acceptable excipient. In further embodiments, the excipient is a cryoprotectant, or is a carrier protein. Alternatively or in addition, the composition is frozen.

In other embodiments, compositions are provided herein that comprises ASC or CM in combination with an excipient, e.g., a pharmacologically acceptable excipient. In further embodiments, the excipient is an osmoprotectant or cryoprotectant, an agent that protects cells from the damaging effect of freezing and ice formation, which may in some embodiments be a permeating compound, non-limiting examples of which are dimethyl sulfoxide (DMSO), glycerol, ethylene glycol, formamide, propanediol, poly-ethylene glycol, acetamide, propylene glycol, and adonitol; or may in other embodiments be a non-permeating compound, non-limiting examples of which are lactose, raffinose, sucrose, trehalose, and d-mannitol. In other embodiments, both a permeating cryoprotectant and a non-permeating cryoprotectant are present. In other embodiments, the excipient is a carrier protein, a non-limiting example of which is albumin. In still other embodiments, both an osmoprotectant and a carrier protein are present; in certain embodiments, the osmoprotectant and carrier protein may be the same compound. Alternatively or in addition, the composition is frozen. The cells may be any embodiment of ASC mentioned herein, each of which is considered a separate embodiment.

Since non-autologous cells may in some cases induce an immune reaction when administered to a subject, several approaches may be utilized according to the methods provided herein to reduce the likelihood of rejection of non-autologous cells. In some embodiments, these approaches include either suppressing the recipient immune system or encapsulating the non-autologous cells in immune-isolating, semipermeable membranes before transplantation. In some embodiments, this may be done whether or not the ASC themselves engraft in the host. For example, the majority of the cells may, in various embodiments, not survive after engraftment for more than 3 days, more than 4 days, more than 5 days, more than 6 days, more than 7 days, more than 8 days, more than 9 days, more than 10 days, or more than 14 days.

Examples of immunosuppressive agents that may be used in the method and compositions provided herein include, but are not limited to, methotrexate, cyclophosphamide, cyclosporine, cyclosporine A, chloroquine, hydroxychloroquine, sulfasalazine (sulphasalazopyrine), gold salts, D-penicillamine, leflunomide, azathioprine, anakinra, infliximab (REMICADE), etanercept, TNF-alpha blockers, biological agents that antagonize one or more inflammatory cytokines, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, and tramadol.

One may, in various embodiments, administer the pharmaceutical composition in a systemic manner (as detailed hereinabove). Alternatively, one may administer the pharmaceutical composition locally, for example, via injection of the pharmaceutical composition directly into an affected tissue region of a patient. In other embodiments, the cells are administered intravenously (IV), intravascularly, subcutaneously (SC), or intraperitoneally (IP), each of which is considered a separate embodiment. In still other embodiments, the pharmaceutical composition is administered intralymphatically, for example as described in U.S. Pat. No. 8,679,834 in the name of Eleuterio Lombardo and Dirk Buscher, which is hereby incorporated by reference.

In other embodiments, for injection, the described cells may be formulated in aqueous solutions, e.g. in physiologically compatible buffers such as Hank's solution, Ringer's solution, or physiological salt buffer, optionally in combination with medium containing cryopreservation agents.

For any preparation used in the described methods, the therapeutically effective amount or dose can be estimated initially from in vitro and cell culture assays. Often, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. The dosage may vary depending upon the dosage form employed and the route of administration utilized. The exact formulation, route of administration and dosage can be, in some embodiments, chosen by the individual physician in view of the patient's condition.

Depending on the severity and responsiveness of the condition to be treated, dosing can be of a single or, in other embodiments, a plurality of administrations, with a course of treatment lasting from several days to several weeks or, in other embodiments, until alleviation of the disease state is achieved.

In certain embodiments, following administration, the majority of the cells, in other embodiments more than 60%, more than 70%, more than 80%, more than 90%, more than 95%, more than 96%, more than 97%, more than 98%, or more than 99% of the cells are no longer detectable within the subject 1 month after administration.

Compositions including the described preparations formulated in a compatible pharmaceutical carrier may also be prepared, placed in an appropriate container, and labeled for treatment of an indicated condition.

The described compositions may, if desired, be packaged in a container that is accompanied by instructions for administration. The container may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The described ASC are, in some embodiments, suitably formulated as pharmaceutical compositions which can be suitably packaged as an article of manufacture. Such an article of manufacture comprises a packaging material which comprises a label describing a use in treating an immune-mediated or circulatory disorder, as described herein. In other embodiments, a pharmaceutical agent is contained within the packaging material, wherein the pharmaceutical agent is effective for the treatment of an immune-mediated or circulatory disorder. In some embodiments, the pharmaceutical composition is frozen.

A typical dosage of the described ASC used alone might range, in some embodiments, from about 10 million to about 500 million cells per administration. For example, the dosage can be, in some embodiments, 10, 20, 30, 40, 50, 60, 70, 80, 90, 100, 125, 150, 175, 200, 225, 250, 275, 300, 325, 350, 375, 400, 425, 450, 475, or 500 million cells or any amount in between these numbers. It is further understood that a range of adherent stromal cells can be used including from about 10 to about 500 million cells, from about 100 to about 400 million cells, from about 150 to about 300 million cells. Accordingly, disclosed herein are therapeutic methods, the method comprising administering to a subject a therapeutically or prophylactically effective amount of ASC, wherein the dosage administered to the subject is 10, 20, 30, 40, 50, 60, 70, 80, 90, 100, 125, 150, 175, 200, 225, 250, 275, 300, 325, 350, 375, 400, 425, 450, 475, or 500 million cells or, in other embodiments, between 150 million to 300 million cells. ASC, compositions comprising ASC, and/or medicaments manufactured using ASC can be administered, in various embodiments, in a series of 1, 2, 3, 4, 5, 6, 7, 8, 9, 10, 11, 12, 13, 14, 15, 1-10, 1-15, 1-20, 2-10, 2-15, 2-20, 3-20, 4-20, 5-20, 5-25, 5-30, 5-40, or 5-50 injections, or more.

In various embodiments is provided a method of treating, ameliorating, inhibiting, or preventing an immune-mediated disease in a subject in need thereof, comprising the step of administering to the subject a pharmaceutical composition comprising the described modified ASC. Also provided is a composition for treating, ameliorating, inhibiting, or preventing an immune-mediated disease, comprising the described modified ASC. Provided in addition is use of the described modified ASC in the preparation of a medicament for treating, ameliorating, inhibiting, or preventing an immune-mediated disease. In certain embodiments, the immune-mediated disease is an autoimmune disease, while in other embodiments the immune-mediated disease is not an autoimmune disease. In still other embodiments, the immune-mediated disease is characterized by chronic inflammation.

In some embodiments, the immune-mediated disease is selected from the group consisting of rheumatoid arthritis, rheumatoid vasculitis, multiple sclerosis (MS), graft vs host disease (GvHD), autoimmune encephalomyelitis (EAE), systemic lupus erythematosus (SLE), Sjogren's syndrome, Myasthenia Gravis (MG), Guillain-Barre Syndrome (GBS), Hashimoto's Thyroiditis (HT), Graves's Disease, Type 1 Diabetes Mellitus (T1DM), inflammatory bowel disease (including, for example, ulcerative colitis and Crohn's disease), asthma, chronic inflammation (including, for example, pancreatitis and non-infectious hepatitis), psoriasis, allergy, Systemic Lupus Erythematosus (SLE), Idiopathic Pulmonary Fibrosis (IPF), alopecia areata (including, for example, alopecia areata, alopecia areata totalis, and alopecia areata universalis), primary sclerosing cholangitis (PSC), and sarcoidosis. In various embodiments, the disease may be a predominantly B-cell mediated disease (e.g. SLE), a predominantly T-cell mediated disease, or a disease involving significant contribution from both B-cells and T-cells.

In certain embodiments, the immune-mediated disease is neuromyelitis optica (NMO). NMO may be described as chronic, inflammatory demyelinating disease of the CNS that is typically associated with serum anti-aquaporin 4 (AQP4) antibodies. Symptoms may include acute attacks of blindness and paraparesis or quadriparesis, often accompanied by sensory and sphincter impairments. Animal models for NMO are well known in the art, for example as mentioned in Example 20.

Alternatively or in addition, optic neuritis (ON) is treated. ON may be described as inflammation of the optic nerve, typically resulting in permanent vision loss, if untreated. Animal models for ON are well known in the art, for example as mentioned in Example 20.

In certain embodiments, the immune-mediated disease is scleroderma, which may be, in various embodiments, localized scleroderma or systemic sclerosis (SSc). In more specific embodiments, the SSc may be limited cutaneous SSc, diffuse cutaneous SSc, or limited SSc. Scleroderma may be characterized by widespread deposition of collagen and other extracellular matrix proteins. Those skilled in the art will appreciate that serological markers of scleroderma include elevated erythrocyte sedimentation rate (ESR); rheumatoid factor (RF), which is positive in 30-40% of cases; anti-nuclear antibodies (ANA), present in 35-96% of cases, anti-SCL-70 (30-70% of cases, particularly in diffuse disease), anti-centromere antibodies (20-40% of cases, particularly in limited disease), and anti-topoisomerase I antibodies. Animal models for scleroderma are well known in the art, for example as mentioned in Example 21.

Animal models for other inflammatory and autoimmune diseases are also well known in the art, for example bleomycin exposure for IPF (Wang Z et al and the references cited therein) and C3H/HeJ inbred mice for alopecia areata (Silva K A et al and the references cited therein) in the inflammatory realm; and collagen-induced arthritis for rheumatoid arthritis (Talaat R M et al and the references cited therein) and superoxide dismutase A peptide induction for sarcoidosis (Swaisgood C M et al. and the references cited therein) in the autoimmune realm.

In other embodiments, there is provided a method of treating, ameliorating, inhibiting, or preventing an immune-mediated disease in a subject in need thereof, comprising the step of administering to the subject a pharmaceutical composition comprising the described CM. Also provided is a composition for treating, ameliorating, inhibiting, or preventing an immune-mediated disease, comprising the described CM. Provided in addition is use of the described CM in the preparation of a medicament for treating, ameliorating, inhibiting, or preventing an immune-mediated disease. In certain embodiments, the immune-mediated disease is an autoimmune disease, while in other embodiments, the immune-mediated disease is not an autoimmune disease. In still other embodiments, the immune-mediated disease is characterized by chronic inflammation.

In other embodiments, there is provided a method of treating, ameliorating, inhibiting, or preventing an immune-mediated disease in a subject in need thereof, comprising the step of administering to the subject a pharmaceutical composition comprising the described exosomes. Also provided is a composition for treating, ameliorating, inhibiting, or preventing an immune-mediated disease, comprising the described exosomes. Provided in addition is use of the described exosomes in the preparation of a medicament for treating, ameliorating, inhibiting, or preventing an immune-mediated disease. In certain embodiments, the immune-mediated disease is an autoimmune disease, while in other embodiments, the immune-mediated disease is not an autoimmune disease. In still other embodiments, the immune-mediated disease is characterized by chronic inflammation.

Also provided herein is a method of treating, or in other embodiments inhibiting, transplant rejection in a subject in need thereof, comprising the step of administering to the subject a pharmaceutical composition comprising the described modified ASC. Also provided is a composition for treating, or in other embodiments inhibiting, transplant rejection in a subject in need thereof, comprising the described modified ASC. Provided in addition is use of the described modified ASC in the preparation of a medicament for treating or inhibiting transplant rejection.

In other embodiments is provided a method of treating, or in other embodiments inhibiting, transplant rejection in a subject in need thereof, comprising the step of administering to the subject a pharmaceutical composition comprising the described exosomes. Also provided is a composition for treating or inhibiting transplant rejection, comprising the described exosomes. Provided in addition is use of the described exosomes in the preparation of a medicament for treating or inhibiting transplant rejection.

In other embodiments is provided a method of treating, or in other embodiments inhibiting, transplant rejection in a subject in need thereof, comprising the step of administering to the subject a pharmaceutical composition comprising the described CM. Also provided is a composition for treating or inhibiting transplant rejection, comprising the described CM. Provided in addition is use of the described CM in the preparation of a medicament for treating or inhibiting transplant rejection.

Also provided herein is a method of treating ischemia in a subject in need thereof, comprising the step of administering to the subject a pharmaceutical composition that comprises the described modified ASC. Also provided is a composition for treating ischemia in a subject in need thereof, comprising the described modified ASC. Provided in addition is use of the described modified ASC in the preparation of a medicament for treating ischemia.

Those skilled in the art will appreciate in light of the present disclosure that the described modified ASC are useful for treatment of ischemia, which may be in more specific embodiments be peripheral ischemia, critical limb ischemia (CLI), lower extremity ischemia, ischemic vascular disease, vascular disease of the kidney, ischemic heart disease, myocardial ischemia, coronary artery disease (CAD), atherosclerotic cardiovascular disease, left main coronary artery disease, arterial occlusive disease, peripheral ischemia, peripheral vascular disease, arteriosclerosis, ischemic brain disease, stroke, cerebral ischemia, vascular disease, Buerger's disease, ischemic renal disease, and/or ischemic placenta.

In other embodiments is provided a method of treating ischemia in a subject in need thereof, comprising the step of administering to the subject a pharmaceutical composition comprising the described exosomes. Also provided is a composition for treating ischemia, comprising the described exosomes. Provided in addition is use of the described exosomes in the preparation of a medicament for treating ischemia.

In other embodiments is provided a method of treating ischemia in a subject in need thereof, comprising the step of administering to the subject a pharmaceutical composition comprising the described CM. Also provided is a composition for treating ischemia, comprising the described CM. Provided in addition is use of the described CM in the preparation of a medicament for treating ischemia.

Also provided herein is a method of treating myocardial infarction (MI) in a subject in need thereof, comprising the step of administering to the subject a pharmaceutical composition comprising the described modified ASC. Also provided is a composition for treating MI in a subject in need thereof, comprising the described modified ASC. Provided in addition is use of the described modified ASC in the preparation of a medicament for treating MI. In certain embodiments, the MI is acute MI.

Also provided herein is a method of inducing, or in other embodiment enhancing, angiogenesis in a subject in need thereof, comprising the step of administering to the subject a pharmaceutical composition comprising the described modified ASC. Also provided is a composition for inducing or enhancing angiogenesis in a subject in need thereof, comprising the described modified ASC. Provided in addition is use of the described modified ASC in the preparation of a medicament for inducing or enhancing angiogenesis.

In other embodiments is provided a method of stimulating angiogenesis in a subject in need thereof, comprising the step of administering to the subject a pharmaceutical composition comprising the described exosomes. Also provided is a composition for stimulating angiogenesis, comprising the described exosomes. Provided in addition is use of the described exosomes in the preparation of a medicament for stimulating angiogenesis.

Also provided herein is a method of enhancing repopulation of hematopoietic stem cells (HSC) in a subject in need thereof, comprising the step of administering to the subject a pharmaceutical composition comprising the described modified ASC. Also provided is a composition for enhancing HSC engraftment in a subject in need thereof, comprising the described modified ASC. Provided in addition is use of the described modified ASC in the preparation of a medicament for enhancing HSC engraftment. Those skilled in the art will appreciate in light of the present disclosure that the described modified ASC are useful for enhancing HSC engraftment, which may, in more specific embodiments, be following radiation-induced bone marrow ablation, chemotherapy, or accidental radiation exposure.

Also provided herein is a method of enhancing engraftment of exogenous HSC in a subject in need thereof, comprising the step of administering to the subject a pharmaceutical composition comprising the described modified ASC. Also provided is a composition for enhancing exogenous HSC engraftment in a subject in need thereof, comprising the described modified ASC. Provided in addition is use of the described modified ASC in the preparation of a medicament for enhancing exogenous HSC engraftment. Those skilled in the art will appreciate in light of the present disclosure that the described modified ASC are useful for enhancing exogenous HSC engraftment, for example decreasing the time of engraftment and/or the number of cells needed for successful engraftment. Those skilled in the art will appreciate that relatively small numbers of cells obtained, for example with cord blood transplantation, may limit the effectiveness of the procedure. The treatment may, in more specific embodiments, follow radiation-induced bone marrow ablation, chemotherapy, or accidental radiation exposure.

In certain embodiments, the ASC are able to support repopulation of the recipient's endogenous hematopoietic system without further co-transplantation of HSC, or in other embodiments are able to enhance exogenous HSC engraftment. This can be achieved, in various embodiments, with or without the ASC themselves engrafting in the host. For example, the cells may, in various embodiments, be able to support repopulation of red blood cells, white blood cells, and/or platelets, without themselves surviving for more than 3 days, more than 4 days, more than 5 days, more than 6 days, more than 7 days, more than 8 days, more than 9 days, more than 10 days, or more than 14 days.

In other embodiments is provided a method of enhancing engraftment of exogenous HSC, or in other embodiments supporting repopulation of an endogenous hematopoietic system, in a subject in need thereof, comprising the step of administering to the subject a pharmaceutical composition comprising the described exosomes. Also provided is a composition for enhancing engraftment of exogenous HSC, or in other embodiments supporting repopulation of an endogenous hematopoietic system, comprising the described exosomes. Provided in addition is use of the described exosomes in the preparation of a medicament for enhancing engraftment of exogenous HSC, or in other embodiments supporting repopulation of an endogenous hematopoietic system.

Also provided herein is a method of inhibiting fibrosis in a subject in need thereof, comprising the step of administering to the subject a pharmaceutical composition comprising the described modified ASC. Also provided is a composition for inhibiting fibrosis in a subject in need thereof, comprising the described modified ASC. Provided in addition is use of the described modified ASC in the preparation of a medicament for inhibiting fibrosis. In certain embodiments, the fibrosis is overgrowth, hardening, or scarring of a body tissue. Alternatively or in addition, the fibrosis may result from excess deposition of extracellular matrix components e.g. collagen. In some embodiments, the fibrosis is pulmonary fibrosis, a non-limiting example of which is idiopathic pulmonary fibrosis. In other embodiments, the fibrosis is secondary to interstitial pneumonia, cystic fibrosis, chronic obstructive pulmonary disease (COPD), acute respiratory distress syndrome (ARDS), inflammatory lung disease, pulmonary infection, radiation pneumonitis, collagen disease-associated interstitial pneumonia, and drug-induced interstitial pneumonia (IIP), specific examples of which include non-specific interstitial pneumonia (NSIP), cryptogenic organizing pneumonia (COP/BOOP), acute interstitial pneumonia (AIP), desquamative interstitial pneumonia (DIP), respiratory bronchiolitis-associated interstitial pneumonia (RB-ILD), and lymphocytic interstitial pneumonia (LIP).

It is clarified that each embodiment of the described ASC may be freely combined with each embodiment relating to a therapeutic method or pharmaceutical composition.

Furthermore, each embodiment of the described exosomes may be freely combined with each embodiment relating to a therapeutic method or pharmaceutical composition.

In still other embodiments, the described CM is used in any of the described therapeutic methods. Each embodiment of CM may be freely combined with each embodiment relating to a therapeutic method or pharmaceutical composition.

Subjects and Routes of Administration

In certain embodiments, the subject treated by the described methods and compositions is a human. In other embodiments, the subject may be an animal. In certain embodiments, the subject may be administered with additional therapeutic agents or cells.

In certain embodiments, the described ASC or composition is administered intramuscularly, subcutaneously, or systemically. In this regard, "intramuscular" administration refers to administration into the muscle tissue of a subject; "subcutaneous" administration refers to administration just below the skin; and "intravenous" administration refers to administration into a vein of a subject.

Also disclosed herein are kits and articles of manufacture that are drawn to reagents that can be used in practicing the methods disclosed herein. The kits and articles of manufacture can include any reagent or combination of reagent discussed herein or that would be understood to be required or beneficial in the practice of the disclosed methods, including adherent stromal cells. In another aspect, the kits and articles of manufacture may comprise a label, instructions, and packaging material, for example for treating an immune-mediated or circulatory disorder or for other therapeutic indications mentioned herein.

Additional objects, advantages, and novel features of the invention will become apparent to one ordinarily skilled in the art upon examination of the following examples, which are not intended to be limiting. Additionally, each of the various embodiments and aspects of the invention as delineated hereinabove and as claimed in the claims section below finds experimental support in the following examples.

EXAMPLES

Reference is now made to the following examples, which together with the above descriptions illustrate certain embodiments in a non-limiting fashion.

Example 1: Production and Culturing of Adherent Stromal Cells

Overview: The manufacturing process for the final cell product consisted of 2 stages: Stage 1, the intermediate cell stock (ICS) production, contains the following steps:
1. Extraction of ASCs from the placenta.
2. 2-dimensional cell growth for up to 12 population doublings.
3. Cell concentration, formulation, filling and cryopreservation.
Stage 2, the thawing of the ICS and further culture, contains the following steps:
1. 2-dimensional cell growth of the thawed ICS for up to 8 additional doublings.
2. 3-dimensional cell growth in bioreactor/s and harvest from bioreactor/s up to 10 additional doublings.
3. Downstream processing: cell concentration, washing, formulation, filling and cryopreservation.

The procedure included periodic testing of the growth medium for sterility and contamination.

Production of ICS

Step 1-1—Extraction of Adherent Stromal Cells (ASC's)

Placentas were obtained from donors up to 35 years old, who were pre-screened and determined to be negative for hepatitis B, hepatitis C, HIV-1 and HIV-2, HTLV-1 and HTLV-2, and syphilis. The donor placenta was maintained sterile and cooled until the initiation of the extraction process.

Within 4 hours of the delivery, the placenta was placed with the maternal side facing upwards and was cut into pieces (sized ~1 cm$^3$), which were washed thoroughly with isotonic buffer) containing gentamicin.

The washed pieces were incubated for 1-3 hours with collagenase and DNAse in isotonic buffer.

Culture medium (DMEM], 10% filtered FBS and L-Glutamine) supplemented with gentamicin, was added, and the digested tissue was coarsely filtered through a sterile stainless steel sieve and centrifuged.

The cells were suspended in culture medium, seeded in flasks, and incubated at 37° C. in a tissue culture incubator under humidified conditions supplemented with 5% C02.

After 2-3 days, cells were washed twice with Phosphate-Buffered Saline (PBS), and the culture medium was replaced.

Cells were incubated for an additional 4-5 days prior to the first passage.

Step 1-2—Initial 2-Dimensional Culturing
Passage 1: Cells were detached using trypsin, centrifuged, and seeded at a culture density of 3.5±0.5×10$^3$ cells/cm$^2$ in tissue culture flasks, in culture medium lacking gentamicin.
Subsequent Passages: When the culture reached 60-90% confluence, cells were passaged as described above.
Step 1-3—Cell Concentration, Washing, Formulation, Filling and Cryopreservation Following the final passage, the resulting cell suspension was centrifuged and resuspended in culture medium at a final concentration of 20-40×10$^6$ cells/milliliter (mL). The cell suspension was diluted 1:1 with 2D Freezing Solution (20% DMSO, 80% FBS), and the cells were cryopreserved in 10% DMSO, 45% FBS, and 45% DMEM. The temperature was reduced in a controlled rate freezer (1° C./min down to −80° C. followed by 5° C./min down to −120° C.), and the cells were stored in a liquid nitrogen freezer to produce the ICS.

Production of Cell Product

Step 2-1: Additional Two-Dimensional (2D) Cell Culturing.

The ICS was thawed, diluted with culture medium, and cultured for up to 10 additional doublings, passaging when reaching 60-90% confluence, then were harvested for seeding in the bioreactor.

Step 2-2: Three Dimensional (3D) Cell Growth in Bioreactor/s

From the cell suspension, 1 or 2 bioreactors were seeded. Each bioreactor contained Fibra-Cel® carriers (New Brunswick Scientific) made of polyester and polypropylene, and culture medium. 170×10$^6$ cells were seeded into each 2.8-liter bioreactor.

The culture medium in the bioreactor/s was kept at the following conditions: temp: 37±1° C., Dissolved Oxygen (DO): 70±10% and pH 7.4±0.2. Filtered gases (Air, $CO_2$, $N_2$ and 02) were supplied as determined by the control system in order to maintain the target DO and pH values.

After seeding, the medium was agitated with stepwise increases in the speed, up to 150-200 RPM by 24 hours. Perfusion was initiated several hours after seeding and was adjusted on a daily basis in order to keep the glucose concentration constant at approximately 550 mg\liter.

Cell harvest was performed at the end of the growth phase (approximately day 6). Bioreactors were washed for 1 minute with pre-warmed sterile PBS, and cells were detached. The cells were found to be over 90% maternally-derived cells.

Step 2-3: Downstream Processing: Cell Concentration, Washing, Formulation, Filling and Cryopreservation In some experiments, the cell suspension underwent concentration and washing, using suspension solution (5% w/v human serum albumin [HSA] in isotonic solution) as the wash buffer, and diluted 1:1 with 2×3D-Freezing solution (20% DMSO v/v and 5% HSA w/v in isotonic solution) to a concentration of 10-20×10$^6$ cells/ml. The temperature of the vials was gradually reduced, and the vials were stored in a gas-phase liquid nitrogen freezer.

Example 2: Osteocyte and Adipose Differentiation Assays Methods

Bone Marrow (BM) Adherent Cells—
BM adherent cells were obtained from aspirated sterna marrow of hematologically healthy donors undergoing open-heart surgery or BM biopsy. Marrow aspirates were diluted 3-fold in HBSS) and subjected to Ficoll-Hypaque (Robbins Scientific Corp. Sunnyvale, Calif.) density gradient centrifugation. Thereafter, marrow mononuclear cells (<1.077 gm/cm$^3$) were collected, washed 3 times in HBSS, and resuspended in growth media [DMEM (Biological Industries, Beit HaEmek, Israel) supplemented with 10% FCS (GIBCO BRL), 10$^{-4}$ M mercaptoethanol (Merck, White House Station, N.J.), Pen-Strep-Nystatin mixture (100 U/ml:100 [μg/ml:1.25 un/ml; Beit HaEmek), 2 mM L-glutamine (Beit HaEmek)]. Cells from individual donors were incubated separately in tissue culture flasks (Corning, Acton, Mass.) at 37° C. (5% C02) with weekly change of culture media. Cells were passaged every 3-4 days using 0.25% trypsin-EDTA (Beit HaEmek). Following 2-40 passages, when reaching 60-80% confluence, cells were collected for analysis.

TABLE 1

Osteogenesis medium components

| Component | Stock conc. | Amount | Final conc. |
|---|---|---|---|
| DMEM low glucose (Invitrogen, Gibco) | | 8.7 ml | 87% |
| Serum (heat inactivated) | | 1 ml | 10% |
| dexamethasone | 1 mM | 1 μl | 0.1 μM |
| Ascorbic Acid-2-Phosphate solution | 0.1M | 20 μl | 0.2 mM |
| Glycerol-2-Phosphate Solution | 1M | 100 μL | 10 mM |
| L-glutamine | X 100 | 100 μl | X 1 |
| Pen & Strep | X 100 | 100 μl | X 1 |

Induction of Osteogenesis

Placenta-derived cells or BM-derived cells were plated (200,000 cells per well) in 1 ml growth medium comprising DMEM (Invitrogen, Gibco), 10% FCS (Invitrogen, Gibco), 2 Mm L-glutamine (Sigma-Aldrich), 45 μg/ml Gentamicin-IKA (Teva Medical) and 0.25 μg/ml Fungizone (Invitrogen, Gibco) in wells coated with a coating mixture containing 12 μg/ml vitronectin and 12 μg/ml collagen, which was provided with the Millipore Mesenchymal Stem Cell Osteogenesis Kit. Cells were grown until 100% confluent (typically overnight) before adding osteogenic differentiation medium.

On differentiation day 1, growth medium was aspirated and replaced with 1 ml osteogenesis induction medium, which was replaced with fresh medium every 2-3 days for 14-17 days. Osteocytes were fixed and stained with Alizarin Red Solution.

In other experiments, a modified osteogenesis induction medium was used, having the components listed in Table 2, including Vitamin D, for 26 days.

TABLE 2

Modified osteogenesis medium components

| Component | Stock conc. | Amount | Final conc. |
|---|---|---|---|
| DMEM high glucose (Biological Industries, Bet HaEmek, Israel) | | 8.7 ml | 87% |
| L-glutamine | X 100 | 100 μl | X 1 |
| Serum (heat inactivated) | | 1 μl | 10% |
| Dexamethasone (Chemicon) | 10 mM | 10 μl | 10 μM |
| Ascorbic Acid-2-Phosphate solution (Chemicon) | 0.1M | 20 μl | 0.2 mM |
| Glycerol-2-Phosphate Solution (Chemicon) | 1M | 100 μL | 10 mM |
| Vitamin D (Sigma) | 10 μM | 10 μL | 10 nM |
| Gentamycin (Biological Industries, Bet HaEmek, Israel) | X 100 | 100 μl | X 1 |

Induction of Adipogenesis

Adipogenesis was carried out according to the instructions provided with the Chemicon Adipogenesis Kit (cat no. scr020, Millipore, Mass., USA)

Adipogenesis Induction Medium

Adipogenesis induction and maintenance medium were freshly prepared prior to every medium exchange, using the components depicted in Tables 3 and 4, below.

TABLE 3

Adipogenesis induction medium components

| Component | Stock conc. | Amount | Final conc. |
|---|---|---|---|
| DMEM low glucose (Biological Industries, Bet HaEmek, Israel) | | 4.4 ml | 90% |
| Serum (heat inactivated) | | 0.5 ml | 10% |
| Dexamethasone (Sigma) | 10 mM | 0.5 μl | 1 μM |
| IBMX (Sigma) | 0.5M | 5 μl | 0.5 mM |
| Insulin (Sigma) | 10 mg/ml | 5 μL | 10 μg/ml |
| Indomethacin (Sigma) | 10 mM | 50 μl | 100 μM |
| Pen & Strep | X 100 | 50 μl | X 1 |

TABLE 4

Adipogenesis maintenance medium components

| Component | Stock conc. | Amount | Final conc. |
|---|---|---|---|
| DMEM low glucose | | 4.4 ml | 90% |
| Serum (heat inactivated) | | 0.5 ml | 10% |
| Insulin | 10 mg/ml | 5 μL | 10 μg/ml |
| Pen & Strep | X 100 | 50 μl | X 1 |

Cell Growth

Placenta-derived or BM-derived cells were plated (200,000 cells per well) in 1 ml growth medium comprising DMEM (Invitrogen, Gibco), 10% FCS (Invitrogen, Gibco), 2 Mm L-glutamine (Sigma-Aldrich), 45 μg/ml Gentamicin-IKA (Teva Medical) and 0.25 μg/ml Fungizone (Invitrogen, Gibco) and were grown until 100% confluent (typically overnight) before initiating adipogenesis differentiation.

On differentiation day 1, growth medium was aspirated and replaced with 1 ml adipogenesis induction medium, which was replaced with fresh induction or maintenance medium every 2-3 days for a total of 25 days, according to the schedule in Table 5.

TABLE 5

Adipogenesis differentiation schedule

| Day | Medium |
|---|---|
| 1 | Adipogenesis Induction medium |
| 3 | Adipogenesis Induction medium |
| 5 | Adipogenesis Induction medium |
| 7 | Adipogenesis Maintenance medium |
| 9 | Adipogenesis Induction medium |
| 11 | Adipogenesis Induction medium |
| 13 | Adipogenesis Induction medium |
| 15 | Adipogenesis Maintenance medium |
| 17 | Adipogenesis Induction medium |

TABLE 5-continued

Adipogenesis differentiation schedule

| Day | Medium |
| --- | --- |
| 19 | Adipogenesis Induction medium |
| 21 | Adipogenesis Induction medium |

On day 25, adipocytes were fixed and stained with oil red solution.

Modified Adipogenesis Induction Medium

The modified adipogenesis induction medium contained the components depicted in Table 6, and was used for a total of 26 days.

TABLE 6

Modified adipogenesis induction medium components

| Component | Stock con | Amount | Final conc. |
| --- | --- | --- | --- |
| DMEM low glucose | | 4.4 ml | 90% |
| Serum (heat inactivated) | | 0.5 ml | 10% |
| Dexamethasone (Sigma) | 1 mM | 5 µl | 1 µM |
| IBMX (Sigma) | 0.5M | 5 µl | 0.5 mM |
| Insulin (Sigma) | 10 mg/ml | 5 µL | 10 µg/ml |
| Indomethacin (Sigma) | 10 mM | 200 µl | 200 µM |
| Gentamycine (Biological Industries) | | 10 µl | |

Results

Osteocyte Induction.

Incubation of BM-derived adherent cells in osteogenic induction medium resulted in differentiation of over 50% of the BM cells, as demonstrated by positive alizarin red staining. On the contrary, none of the placental-derived cells exhibited signs of osteogenic differentiation.

Next, a modified osteogenic medium comprising Vitamin D and higher concentrations of dexamethasone was used. Over 50% of the BM cells underwent differentiation into osteocytes, while none of the placental-derived cells exhibited signs of osteogenic differentiation.

Adipocyte Induction.

Adipocyte differentiation of placenta- or BM-derived adherent cells in adipocyte induction medium resulted in differentiation of over 50% of the BM-derived cells, as demonstrated by positive oil red staining and by typical morphological changes (e.g. accumulation of oil droplets in the cytoplasm). In contrast, none of the placental-derived cells differentiated into adipocytes.

Next, a modified medium containing a higher indomethacin concentration was used. Over 50% of the BM-derived cells underwent differentiation into adipocytes. In contrast, none of the placental-derived cells exhibited morphological changes typical of adipocytes.

Example 3: Marker Expression on Adherent Stromal Cells

Methods (Examples 3-5)

FACS analysis of membrane markers was performed by staining cells with monoclonal antibodies (MAbs). 400,000-600,000 cells were suspended in 1 ml flow cytometer buffer in a 5 ml test tube and incubated for 15 minutes at room temperature (RT), in the dark, with each of the following MAbs: PE-conjugated anti-human CD29 MAb (Becton Dickinson [BD]), PE-conjugated anti human CD73 MAb (BD), PE-conjugated anti human CD105 MAb (BD), PE-conjugated anti human CD90 MAb (BD), PE-conjugated anti-human CD45 MAb (BD), PE-conjugated anti-human CD19 MAb (BD), PE-conjugated anti human CD14 MAb (BD), PE-conjugated anti human HLA-DR MAb (BD), PE-conjugated anti human CD34 MAb (BD), PE-conjugated anti human CD31 MAb (BD), PE-conjugated anti-human CD200 MAb (BD), PE-conjugated Isotype IgG2beta (BD), PE-conjugated Isotype IgG1alpha (BD); and anti-CD106, anti-CD54, anti-CD56, anti-CD49d, anti-glyA, and anti-CD39, all PE-conjugated and from BD; Alexa Fluor®-conjugated anti-SSEA4 (eBioscience), and IgG3 kappa isotype control (Biolegend).

Cells were washed twice with flow cytometer buffer, resuspended in 400 microliters (mcl) flow cytometer buffer, and analyzed by flow cytometry.

Human/Human Mixed Lymphocyte Reaction (IR)

$2 \times 10^5$ peripheral blood (PB) derived MNC (from donor A) were stimulated with equal amount of irradiated (3000 Rad) PB derived MNCs (from donor B). Increasing amounts of stromal cells were added to the cultures. Three replicates of each group were seeded in 96-well plates. Cells were cultured in RPMI 1640 medium containing 20% FBS. Plates were pulsed with 1 microCurie (mcCi)$^3$H-thymidine during the last 18 hrs. of the 5-day culturing. Cells were harvested over a fiberglass filter and thymidine uptake was quantified with scintillation counter.

Human/Rat PBMC Proliferation Assay

ASC were seeded in a 96-well plate and incubated for 24 hours. Peripheral blood mononuclear cells (PBMCs) were labeled with carboxyfluorescein succinimidyl ester (CFSE), a fluorescent cell staining dye, which diffuses into cells and tags proliferating cells, activated with PHA, and co-cultured with ASC for 5 days. Maximum proliferation (100%) was arbitrarily set as the proliferation of PBMC cells after PHA stimulation in the absence of ASC. Flow cytometry methods were used to determine the percentage of PBMCs. Results may be presented both as % Inhibition of T Cell Proliferation (% ITCP) or as Relative Percent of % ITCP, with the latter calculated by dividing the % ITCP of the tested sample by that of the reference batch.

For CFSE staining, PB-MNC cells were stained for CFSE (Molecular Probes) for proliferation measurement before culturing. Cells were collected after 5 days, and the intensity of CFSE staining was detected by Flow Cytometry.

ELISA

MNCs (isolated from peripheral blood) were stimulated with 5 microgram (mcg)/ml ConA (Sigma), 0.5 mcg/ml LPS (SIGMA), or 10 mcg/ml PHA (SIGMA) in the presence of stromal cells under a humidified 5% $CO_2$ atmosphere at 37° C. Supernatants were collected and subjected to cytokine analysis using ELISA kits for IFN-gamma (DIACLONE), TNF-alpha (DIACLONE), and IL-10 (DIACLONE).

Results

Expression of Cellular Markers on Isolated Cells— the surface antigens expressed by the isolated cells were examined using monoclonal antibodies. The cells expressed CD73, CD29, and CD105, and did not express the markers CD34, CD45, CD19, CD14, and HLA-DR. More specifically, all the positive markers were expressed by more than 90% of the cells, and all the negative markers were expressed by less than 3% of the cells.

Furthermore, the cells did not express endothelial markers as shown by negative staining for the two endothelial markers CD31 and KDR. However, expression of a fibroblast-typical marker, D7-fib, was evident.

Example 4: Immunogenicity and Immunomodulatory Properties of ASC

Figure 2:
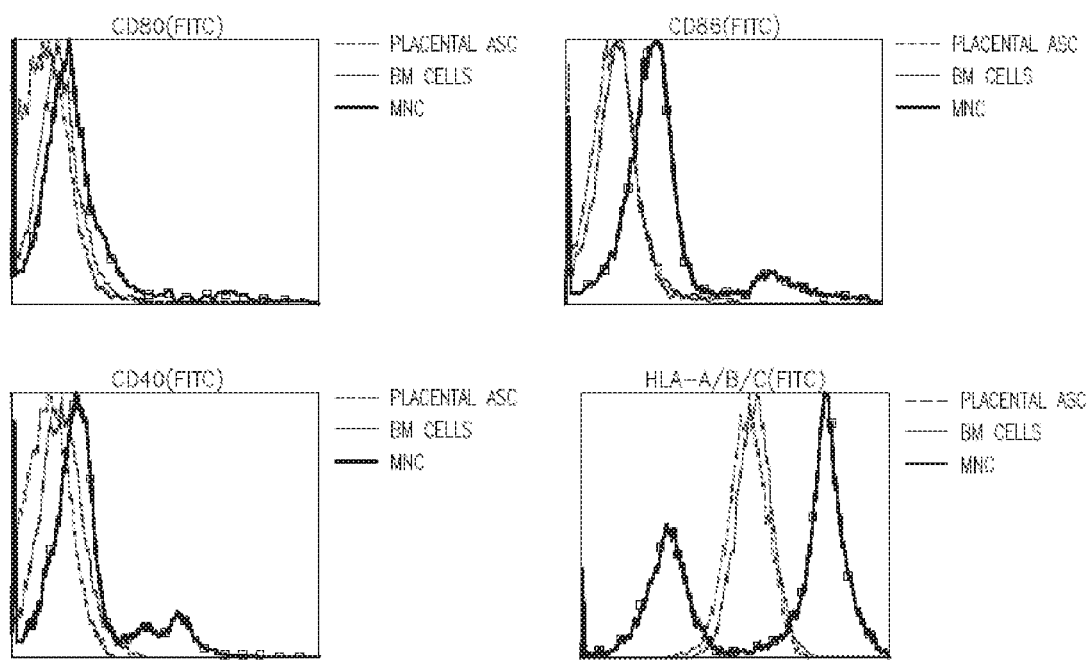
FIG. 2 contains plots of expression of stimulatory and co-stimulatory molecules on ASC. Upper left: Expression of CD80. Upper right: Expression of CD86. Lower left. Expression of CD40. Lower right: Expression of HLA-A/B/C. Negative controls were prepared with relevant isotype fluorescence molecules. Dotted, light, and heavy lines indicate marker-expression by placental ASC, bone marrow (BM) cells, and mononuclear cells (MNC), respectively.

The expression of co-stimulatory molecules on ASC was measured. FACS analysis demonstrated the absence of CD80, CD86 and CD40 on the cell membranes (FIGS. 2A-C). Moreover, the cells expressed low levels of HLA class I molecules, as detected by staining for HLA A/B/C (FIG. 2D).

Figure 3:
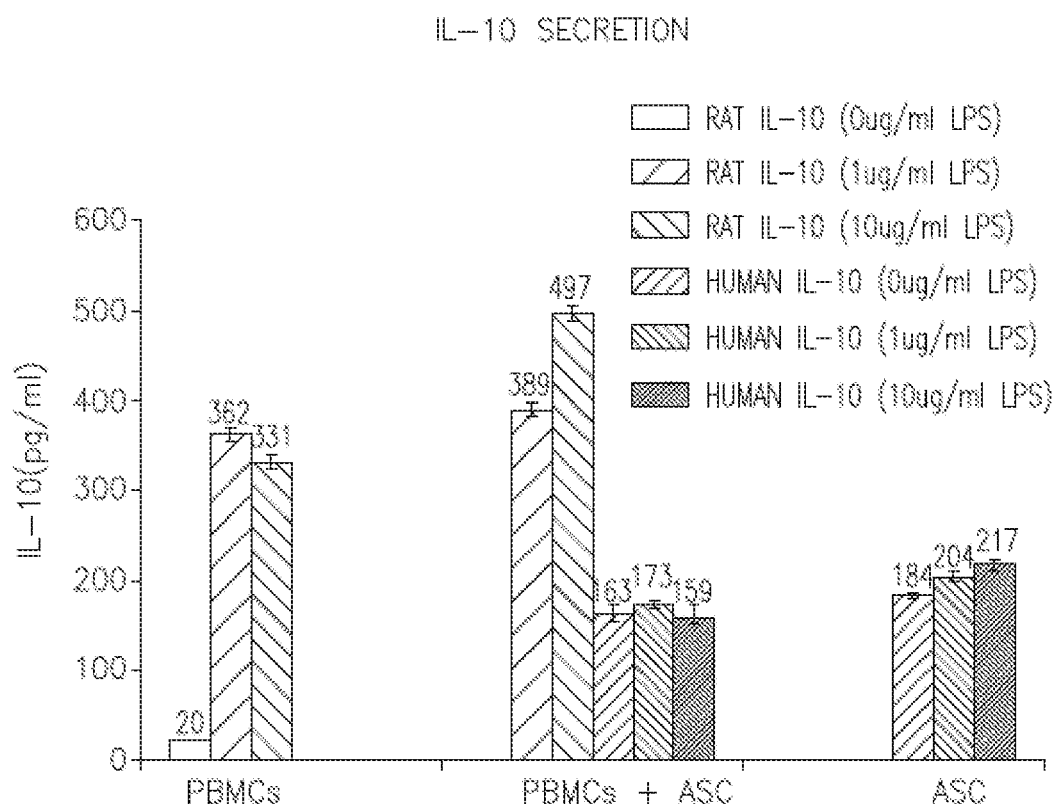
FIG. 3 is a graph of secretion of IL-10 by PBMC in the absence or presence of ASC. Bars in each group, from left to right are: 1-3: Rat IL-10 after stimulation with 0, 1, or 10 mcg/ml LPS; and 4-6: human IL-10 after stimulation with 0, 1, or 10 mcg/ml LPS.

To further investigate the immunogenicity and the immunomodulatory properties of the cells, human/rat Mixed Lymphocyte Reaction (MLR) tests were performed. Rat PBMC were stimulated with LPS (lipopolysaccharide) in the absence or presence of (human) ASC, and secretion of IL-10 by the PBMC was measured. ASC increased the IL-10 secretion (FIG. 3).

Figure 4A:
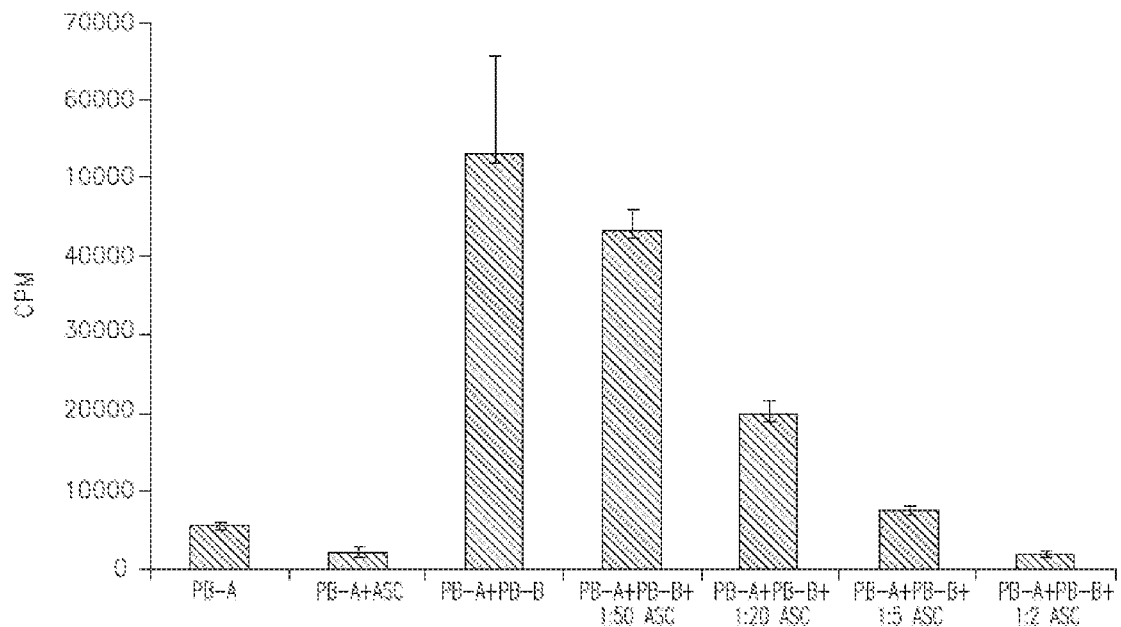
FIGS. 4A-B are charts depicting lymphocyte proliferation, measured by [$^3$H]thymidine incorporation. A. $2 \times 10^5$ peripheral blood (PB)-derived MNC (donor A) were stimulated with an equal number of irradiated (3000 Rad) PB-derived MNCs (donor B) in a MLR test, in the presence of different amounts of ASC. B. PB-derived MNCs stimulated with ConA (1.5 mg/ml). For (A) and (B), three replicates of each sample were performed.
Figure 4B:
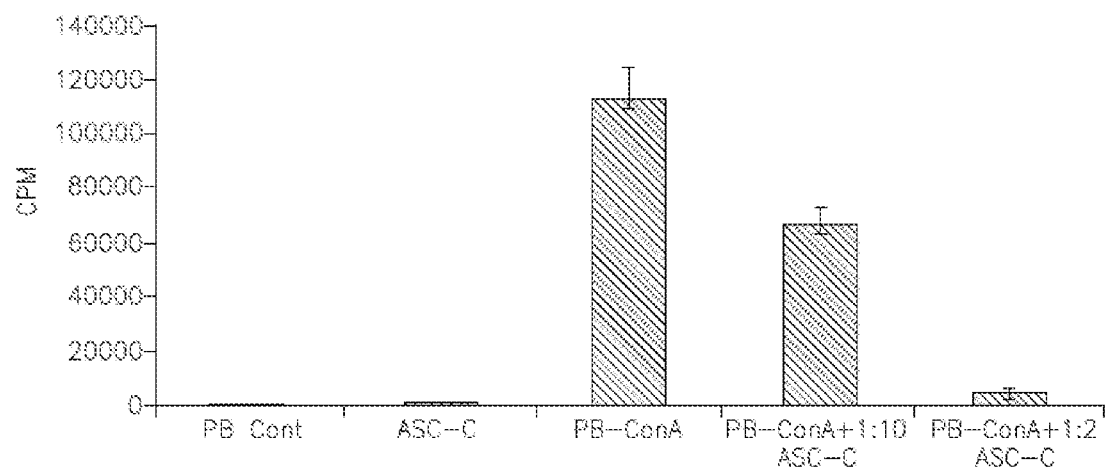

MLR performed with 2 different donors also showed that the ASC escaped allorecognition and reduced lymphocyte proliferation, as measured by thymidine incorporation, following mitogenic stimuli, such as allogeneic cells (FIG. 4A) and Concanavalin A (Con A) (FIG. 4B) and Phytohemagglutinin (PHA; typically at least 25% inhibition relative to PHA alone), and non-specific stimulation by anti-CD3 and anti-CD28. The reduction in lymphocyte proliferation was dose dependent with the number of ASC.

Next, PBMC were stimulated by PHA using the Transwell® method (which prevents cell-to-cell contact but enables the diffusion of cytokines between the two compartments). The inhibition of proliferation was maintained even in this assay, showing that cell-to-cell contact was not necessary for the inhibition.

Example 5: ASC Alter Cytokine Secretion by PBMC

Figure 5A:
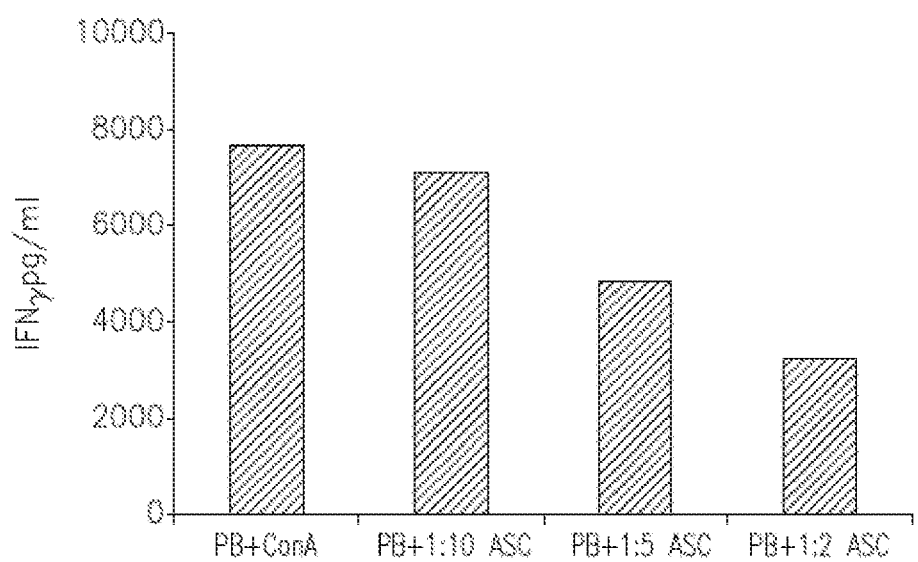
FIGS. 5A-C are charts depicting ASC regulation of pro- and anti-inflammatory cytokine secretion by human MNCs (isolated from peripheral blood). A-B depict secretion of IFN-gamma (A) and TNF-alpha (B) stimulation with ConA. C depicts secretion of IFN-gamma, TNF-alpha and IL-10 in pg/ml (left, middle, and right bars in each series, respectively) following stimulation with LPS. Supernatants were analyzed by ELISA
Figure 5B:
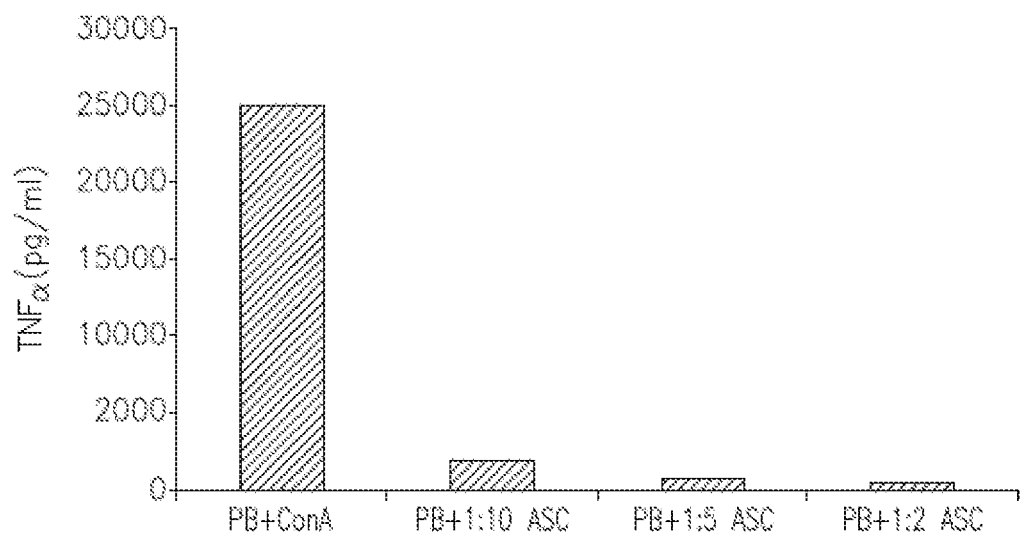
Figure 5C:
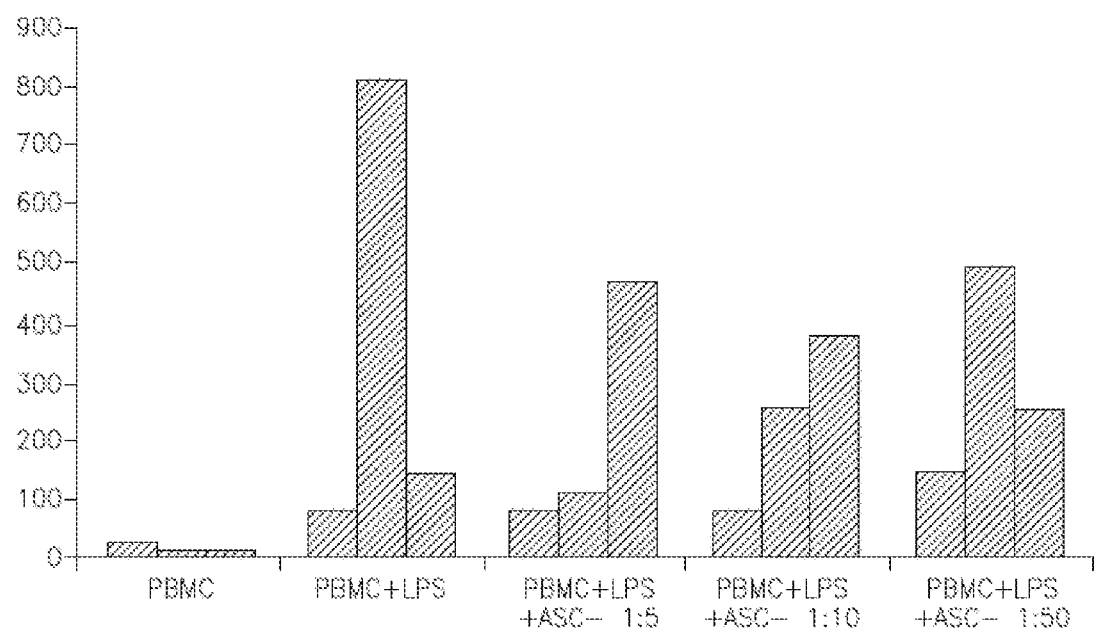

Additional co-culture studies were performed to test the effect of ASC on secretion of cytokines by lymphocytes. Culturing of PB-derived mononuclear cells (PBMC) with ASC slightly reduced IFN-gamma secretion and dramatically reduced TNF-alpha secretion by the PBMC, even when only low amounts of ASC were present (FIGS. 5A-B). Under conditions of LPS stimulation, the ASC increased secretion of IL-10 by PBMC, while decreasing their secretion of TNF-alpha, in a dose-dependent manner (FIG. 5C).

Example 6: Adherent Stromal Cells Stimulate ECP

Protocol-Endothelial Cell Proliferation (ECP) Assay:

ASC were prepared as described in Example 1, harvested by vibration, as described in PCT International Application Publ. No. WO 2012/140519, and were cryopreserved. $1 \times 10^6$ thawed ASC were seeded in 2 ml DMEM medium in tissue culture plates. After 24 hours (hr), the medium was replaced with EBM-2 medium (Lonza Group Ltd, Basel, Switzerland), and cells were incubated under hypoxic conditions (1% $O_2$) for an additional 24 hr, after which the conditioned medium (CM) was collected. In parallel, 750 human umbilical cord endothelial cells (HUVEC) were seeded, incubated for 24 hr, and then incubated with the CM, for 4 days under normoxic conditions at 37° C. After removal of the CM, the proliferation of the HUVEC cells was assayed using the AlamarBlue® fluorescent assay.

Results

Figure 6:
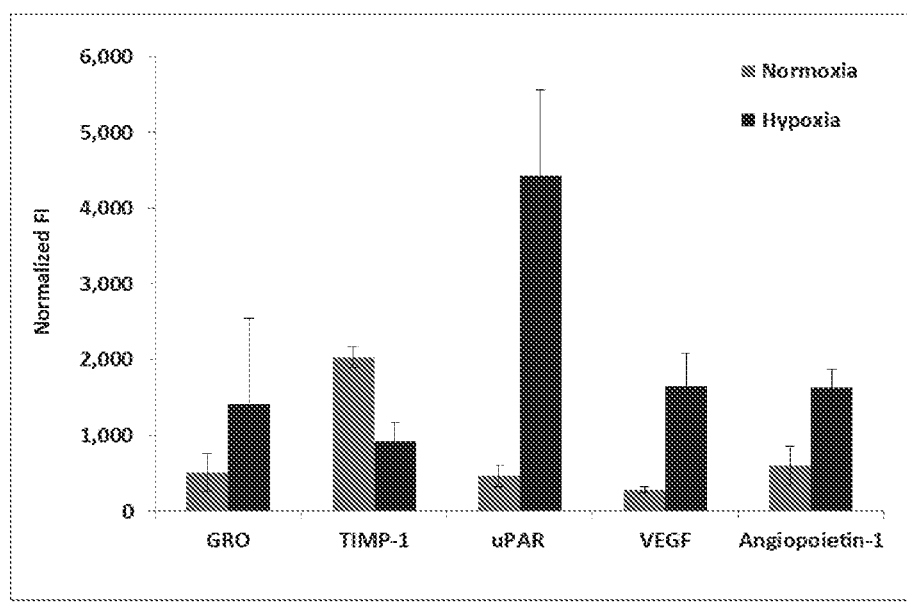
FIG. 6 is a graph of secretion profile of ASC under normoxic or hypoxic conditions.

ASC cultured under normoxic (5% O2) or hypoxic conditions were tested for protein secretion, using Cytokine (Human) Antibody Array C Series 4000 (RayBio). Secretion of several pro-angiogenic factors was up-regulated under hypoxic conditions, as shown in FIG. 6.

In additional experiments, various batches of ASC were co-incubated with HUVEC cells to test their effect on ECP. Stimulation of ECP was observed, typically at least 135% of the ECP observed in the absence of ASC.

Example 7: Treatment of ASC with Pro-Inflammatory Cytokines During 3D Culturing Methods General Experimental Protocol ASC were obtained from the placenta and cultured under 2D conditions, then under 3D conditions, and were then harvested, all as described in Example 1, with the following deviation: 36-40 hours before the end of the 3D culture (typically on day 5 or 6), the feed bag medium was replaced with DMEM, with or without the addition of 10 nanograms/milliliter (ng/ml) Tumor Necrosis Factor alpha (TNF-alpha), 10 ng/ml Interferon-Gamma (IFN-g), and/or 10% FBS (see Table 7), and the bioreactor was incubated in batch mode (or, in selected experiments, in perfusion mode) for an additional day. Levels of secreted cytokines were measured in the bioreactor medium, using the RayBio® Human Cytokine Array kit.

TABLE 7

Incubation conditions that were tested.

| Designation | Cytokines | FBS |
|---|---|---|
| 1 | None | NO |
| 2 | None | YES |
| 3 | TNF | NO |
| 4 | TNF | YES |
| 5 | TNF + IFN | NO |
| 6 | TNF + IFN | YES |

Measuring cytokines in conditioned medium: After bioreactor incubation, cells were cryopreserved. Thawed cells were incubated for 24 hr under hypoxic incubation in 1 ml in tissue culture plates, as described in the context of the ECP assay in the previous Example, levels of secreted cytokines were measured in the CM.

Quantitative detection of secreted proteins: IL-6 was quantitatively measured using the human IL-6 immunoassay Quantikine® ELISA kit (R&D Systems). VEGF was quantitatively measured using the Human VEGF immunoassay Quantikine® kit (R&D Systems).

Results

In a series of experiments testing various conditions side-by-side, ASC were incubated in a bioreactor as described in the previous Examples. On the last day of the bioreactor incubation, the medium was replaced by medium containing or lacking added TNF-alpha and/or IFN-gamma, in the presence or absence of FBS. VEGF and IL-6 secretion were measured by ELISA in both the bioreactor medium and (in thawed cells) in CM following incubation in tissue culture plates. Inclusion of TNF-alpha significantly increased secretion of VEGF, whether or not IFN-gamma was present (Table 8).

TABLE 8

Secretion of VEGF (picograms/ml [pg/ml]) by ASC under various conditions.

| Expt. # | Cytokines | FBS | VEGF in CM/ RPD* | VEGF in bioreactor medium/RPD* |
|---|---|---|---|---|
| 1 | TNF + IFN | NO | 619/3 | 195/3 |
|   | None | NO | 274/7 | 65/0 |
| 2 | TNF + IFN | NO | 7540/1 | 151/3 |
|   | None | NO | 3266/4 | 140/3 |
| 3 | TNF + IFN | YES | 371/3 | 1749/2 |
|   | TNF | YES | 370/10 | 1128/5 |
| 4 | TNF + IFN | YES | NT (not tested) | 373/2 |
|   | TNF | YES | NT | 348/8 |
| 5 | TNF + IFN | NO | 732 ± 20** | (not performed) |
|   | None | NO | 650 ± 46** | (not performed) |

*In this table and throughout the document, RPD refers to the percentage difference between duplicate samples in the ELISA.
**Indicated number is the standard deviation.

In the same experiment, inclusion of TNF-alpha significantly increased IL-6 secretion, which was further increased by IFN-gamma.

Figure 7A:
FIGS. 7A-B are graphs depicting secretion, measured by fluorescence, of various factors following incubation of ASC with TNF-alpha+IFN-gamma (unfilled bars) or control media (filled bars) in two separate experiments. C-D are graphs depicting fold-increase of secretion, measured by fluorescence, of GRO, IL-8, MCP-1, and RANTES (C), and IL-6, MCP-3, Angiogenin, Insulin-like Growth Factor Binding Protein-2 (IGFBP-2), Osteopontin, and Osteoprotegerin (D) following incubation of ASC with TNF-alpha alone, relative to incubation with control media (no cytokines).
Figure 7B:
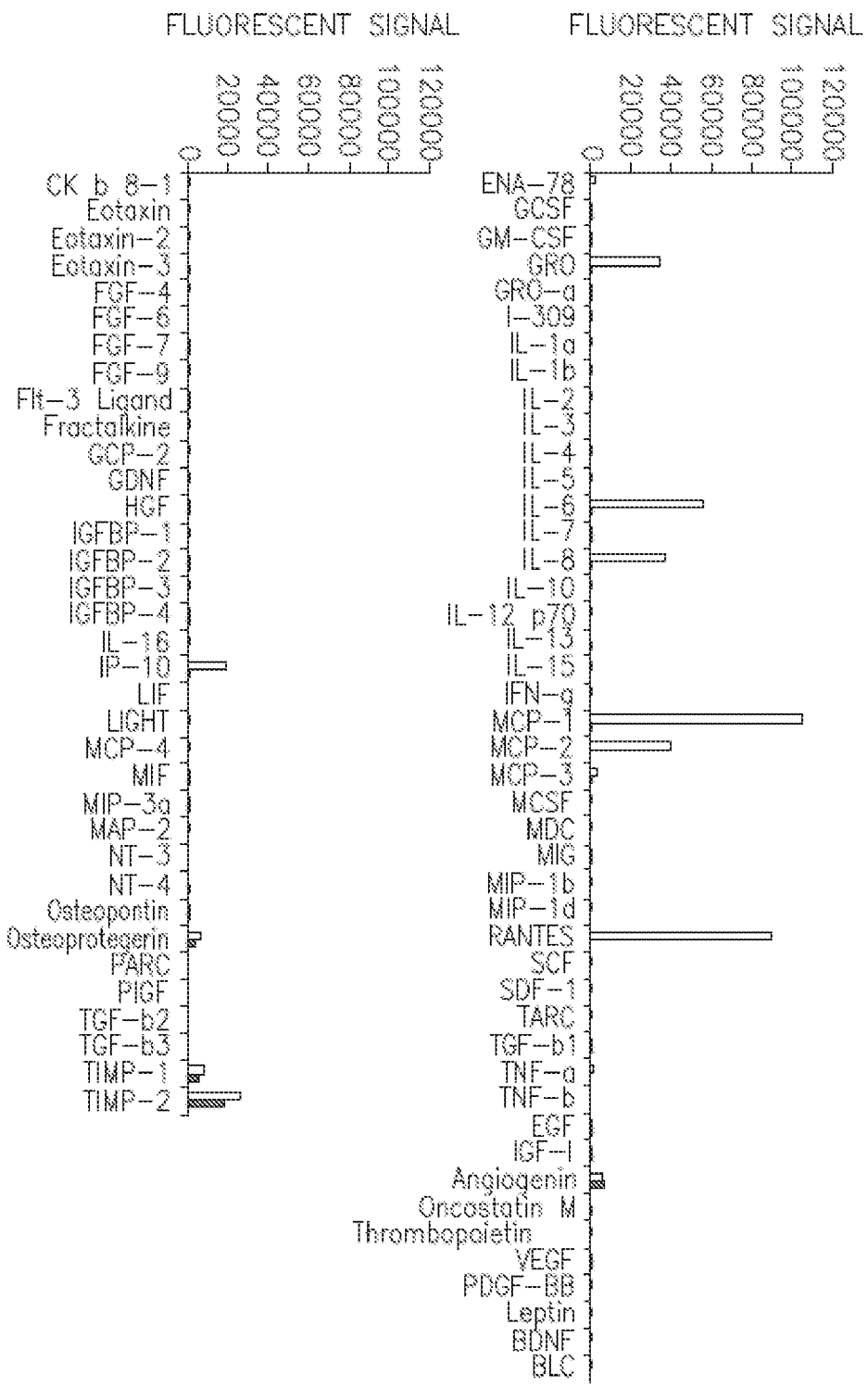
Figure 7C:
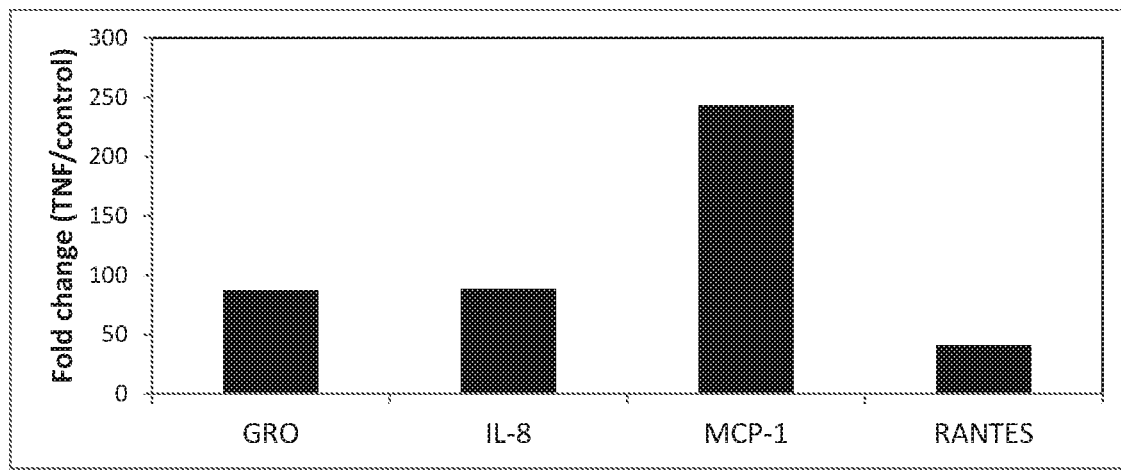
Figure 7D:
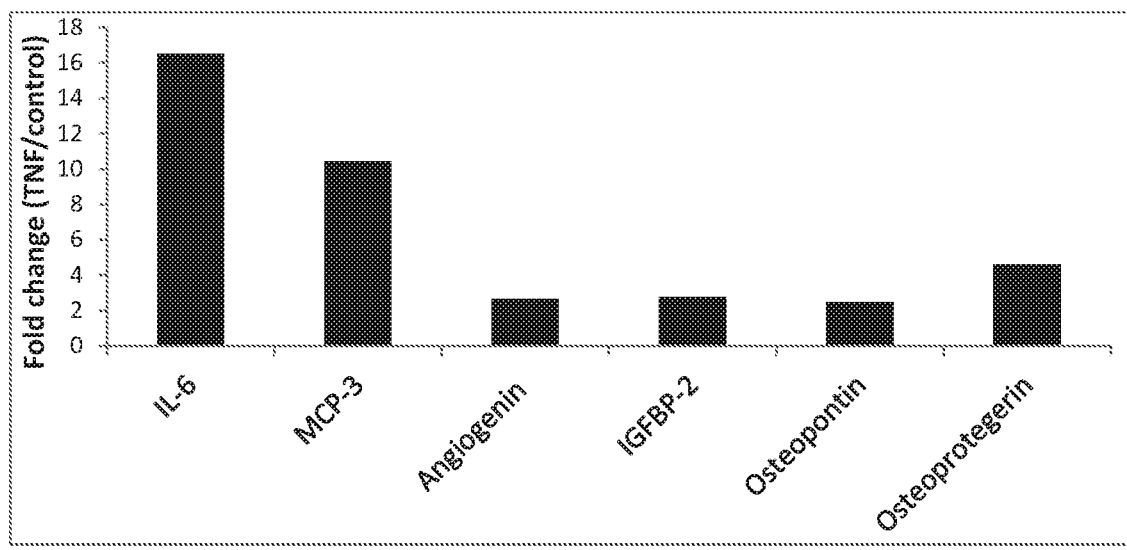

Expression of a panel of factors in the bioreactor media of Experiments 1-2 (see Tables 8-9), all performed in the absence of serum, was measured by a fluorescence-based cytokine array assay, revealing the increased expression of several factors, including GRO, IL-6, IL-8, MCP-1, MCP-2, MCP-3, RANTES, and IP-10 (Experiments 1-2 are shown in FIGS. 7A-B, respectively). In another experiment, TNF-alpha alone was compared to medium without cytokines (also in the absence of serum), showing increased expression of GRO, IL-8, MCP-1, RANTES, and, to a lesser extent, IL-6, MCP-3, Angiogenin, Insulin-like Growth Factor Binding Protein-2 (IGFBP-2), Osteopontin, and Osteoprotegerin (FIGS. 7C-D).

Figure 8A:
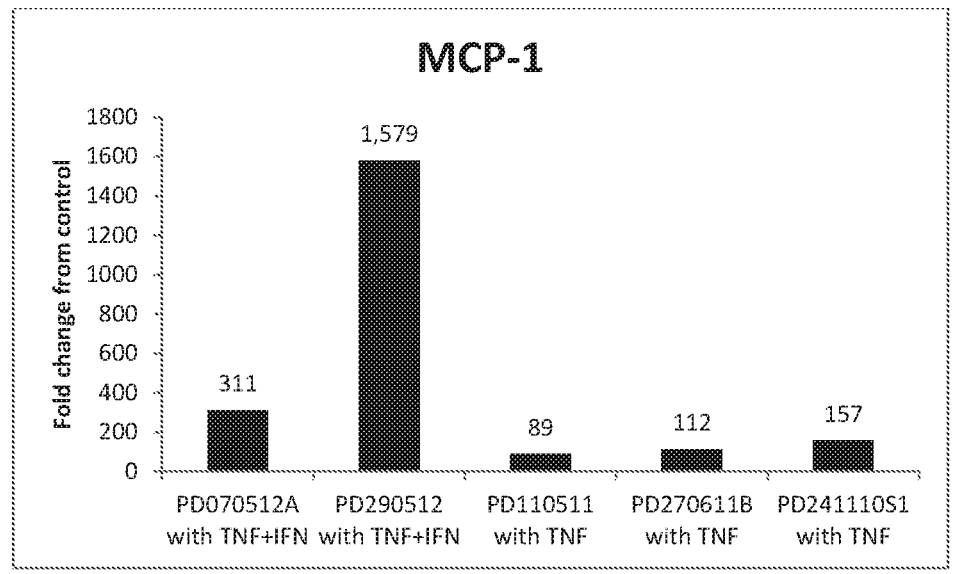
FIGS. 8A-B are graphs depicting fold-increase relative to control medium (containing no cytokines) in secretion of MCP-1 (A) and GM-CSF (B) in several experiments, as measured by ELISA.
Figure 8B:
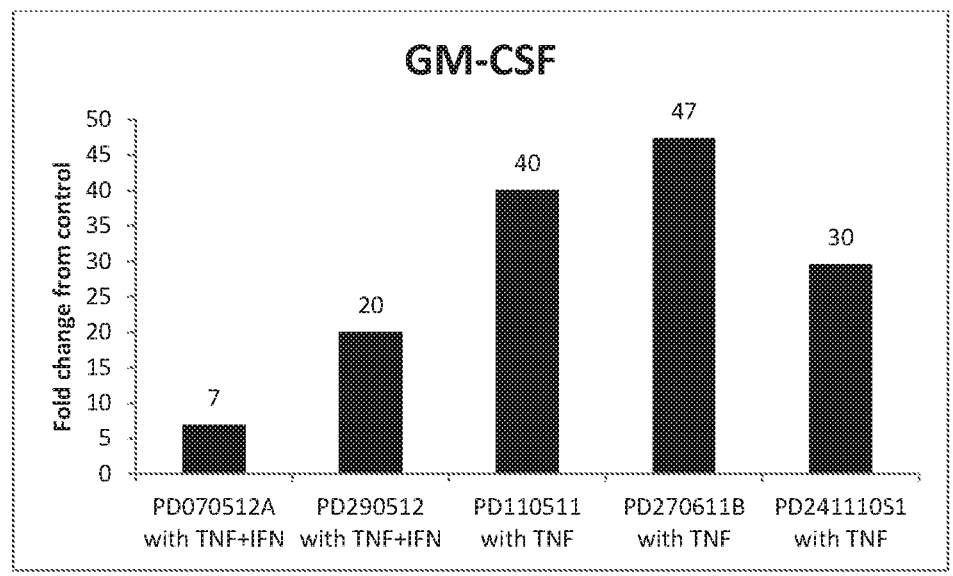
Figure 9A:
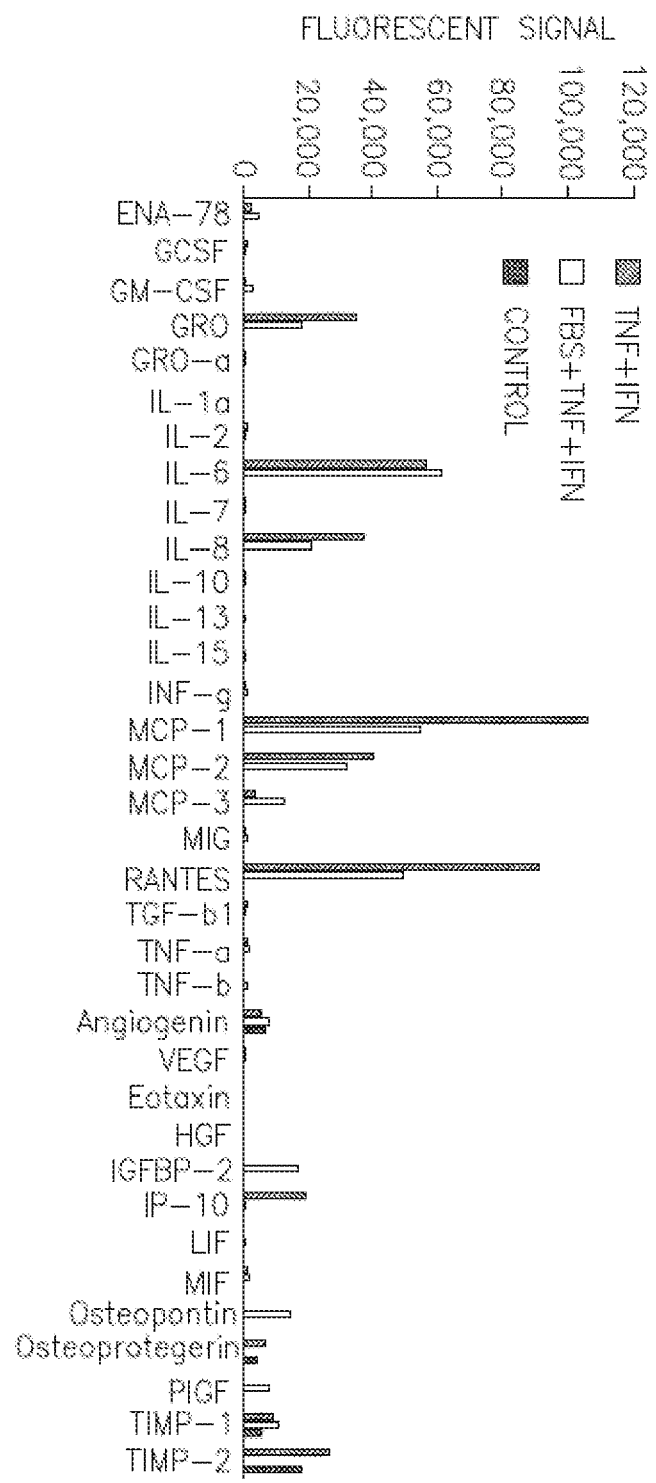
FIGS. 9A-B are graphs depicting secretion, in units of fluorescence signal, of various factors by TNF-alpha+IFN-gamma (A) or TNF-alpha alone (B) in the presence or absence of FBS. In (A), gray, white, and black bars indicate TNF-alpha+IFN-gamma; TNF-alpha+IFN-gamma+FBS; and control (no cytokines or serum), respectively. In (B), gray, white, and black bars indicate TNF-alpha alone; TNF-alpha+FBS; and control (no cytokines or serum), respectively.
Figure 9B:
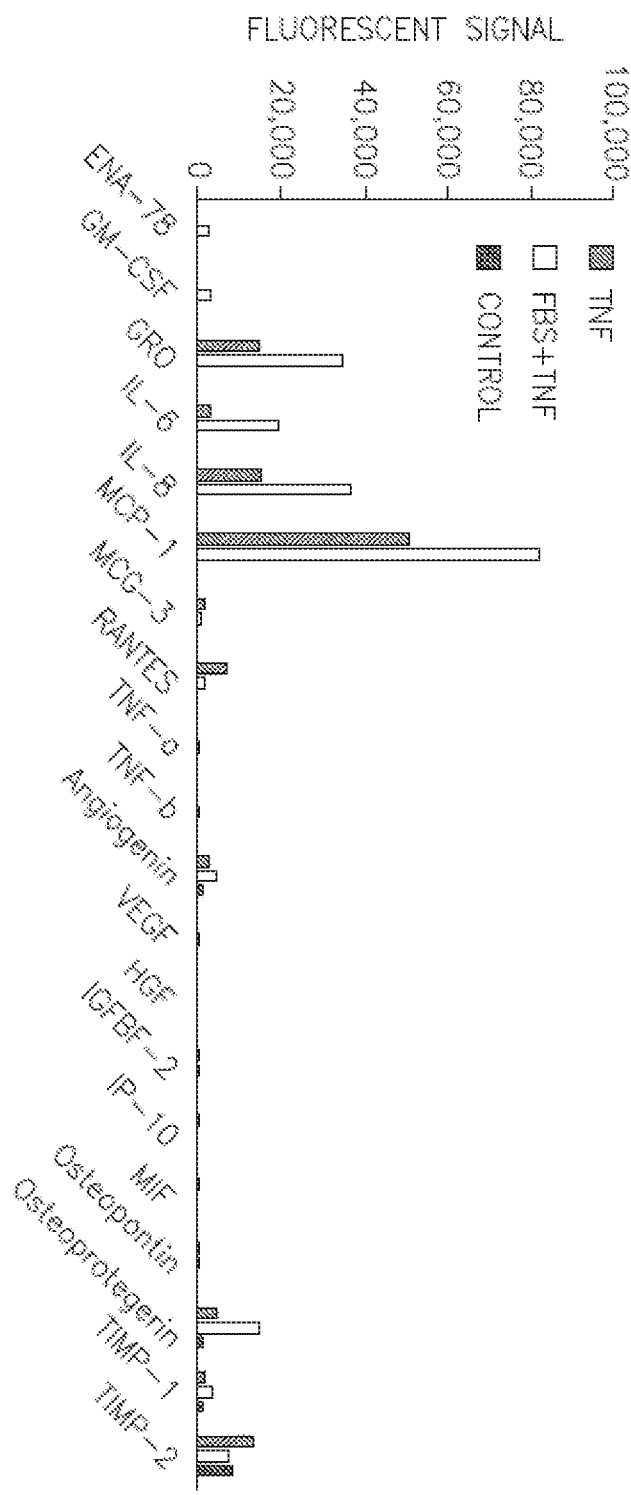
Figure 9D:
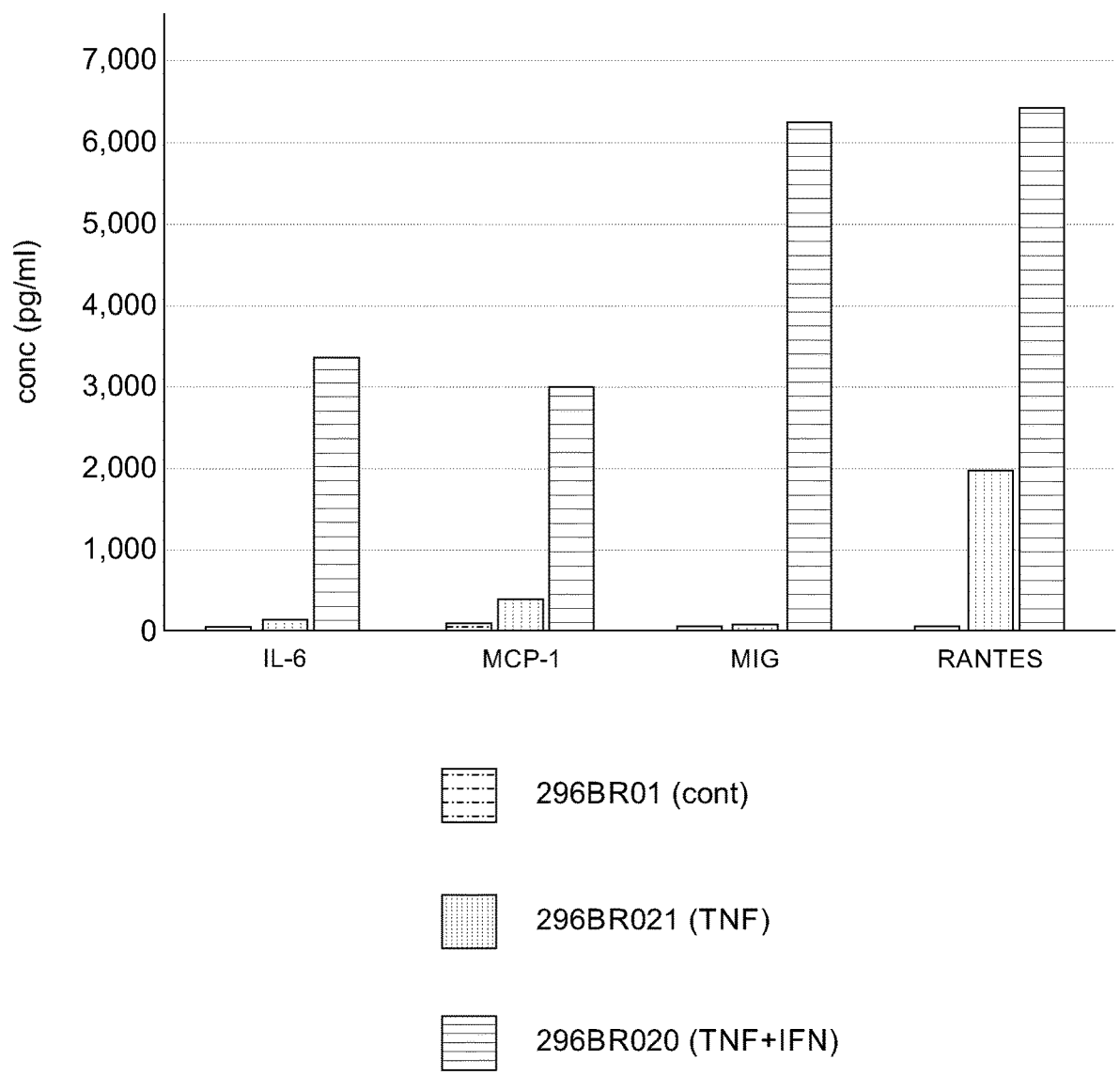
Figure 9E:
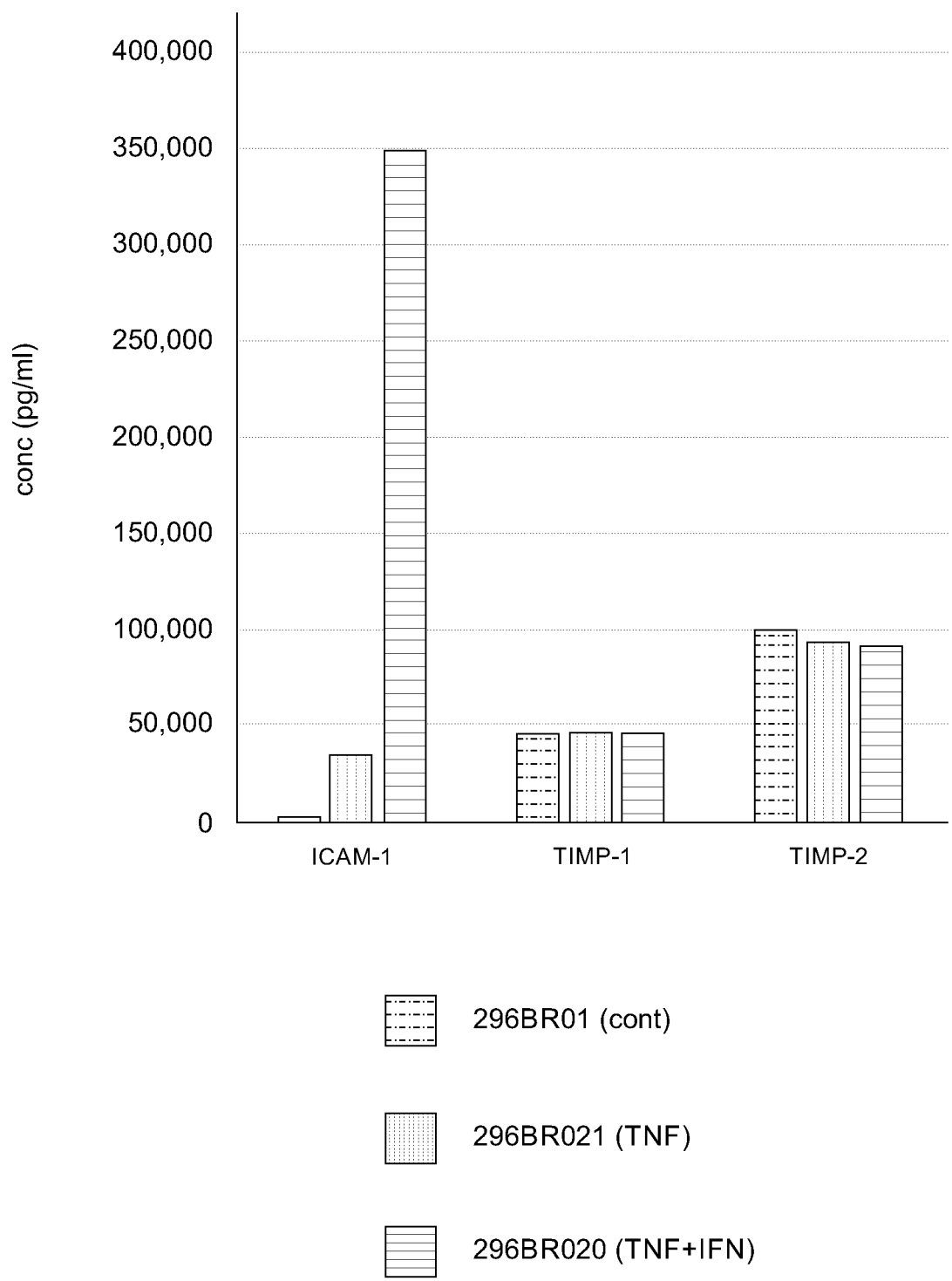
Figure 12A:
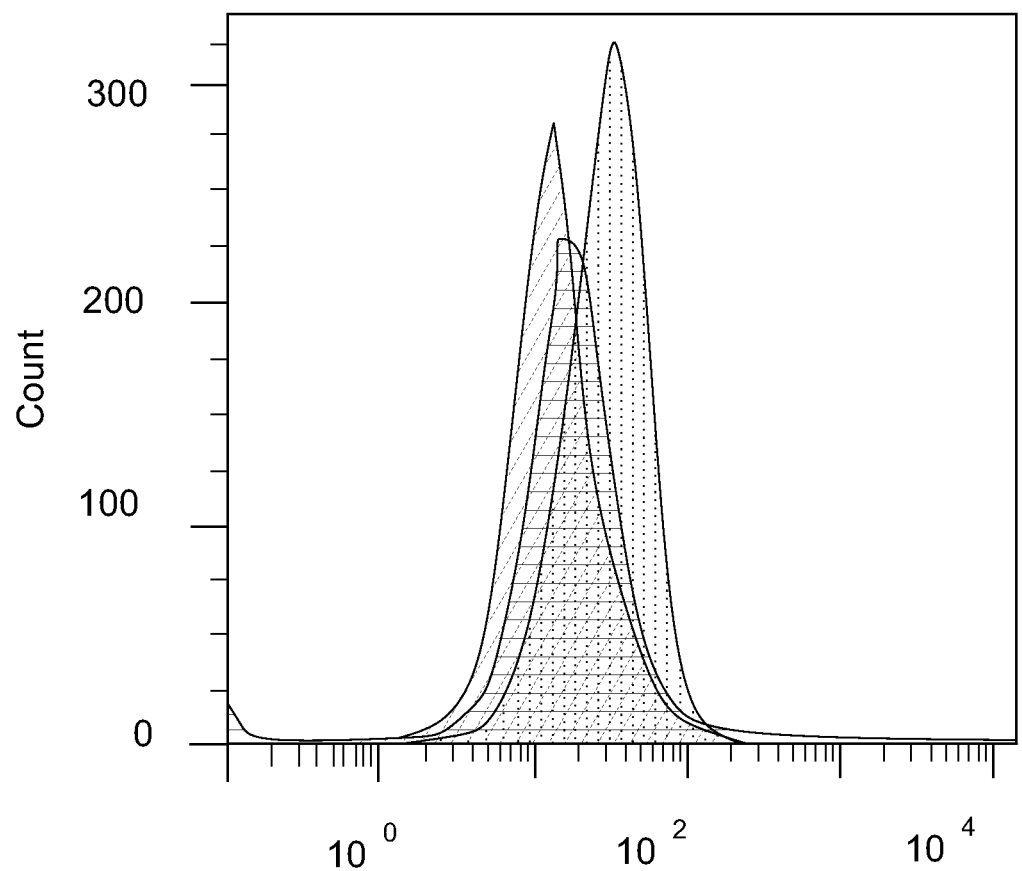
Figure 12B:
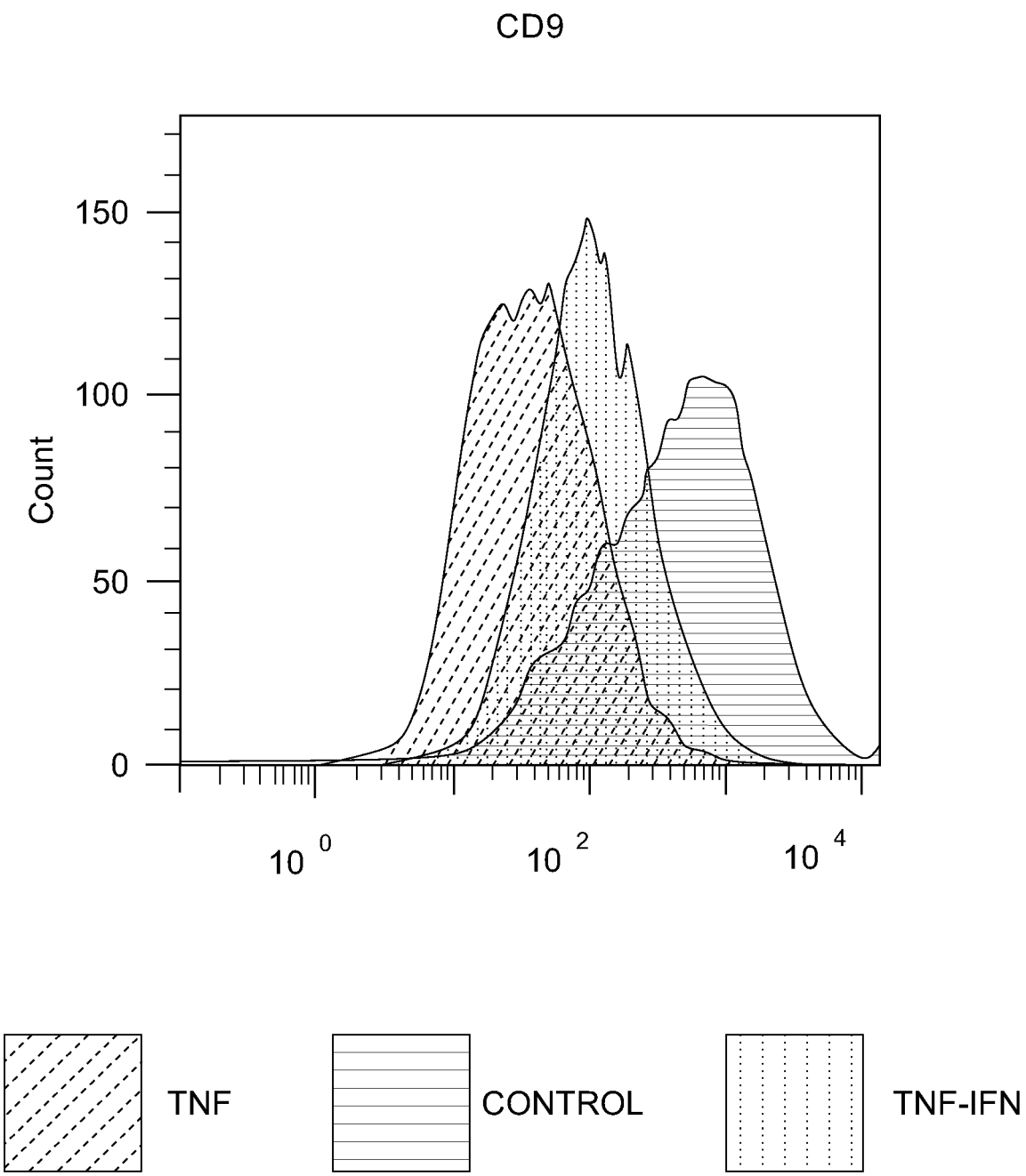
Figure 12C:
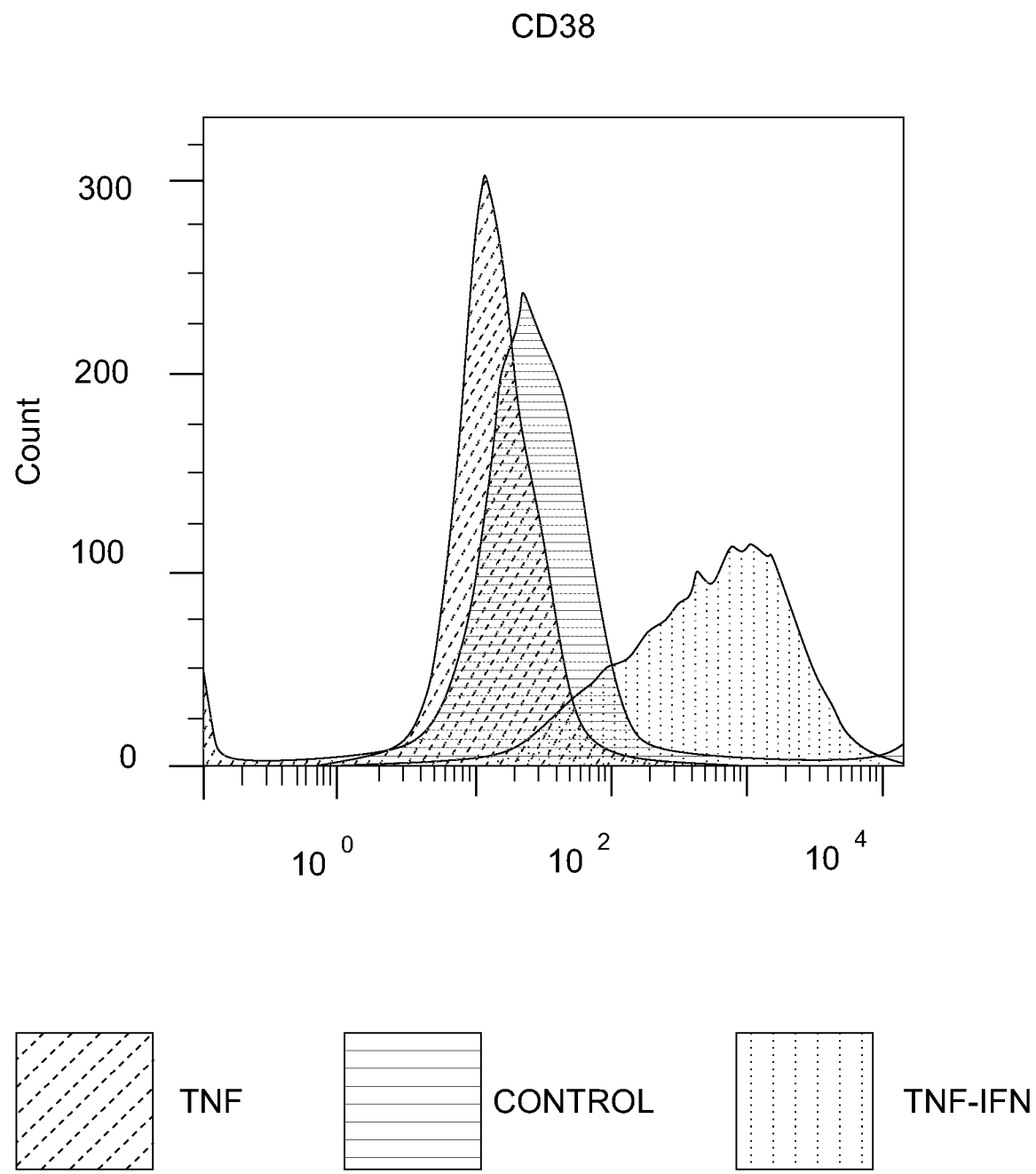
Figure 12D:
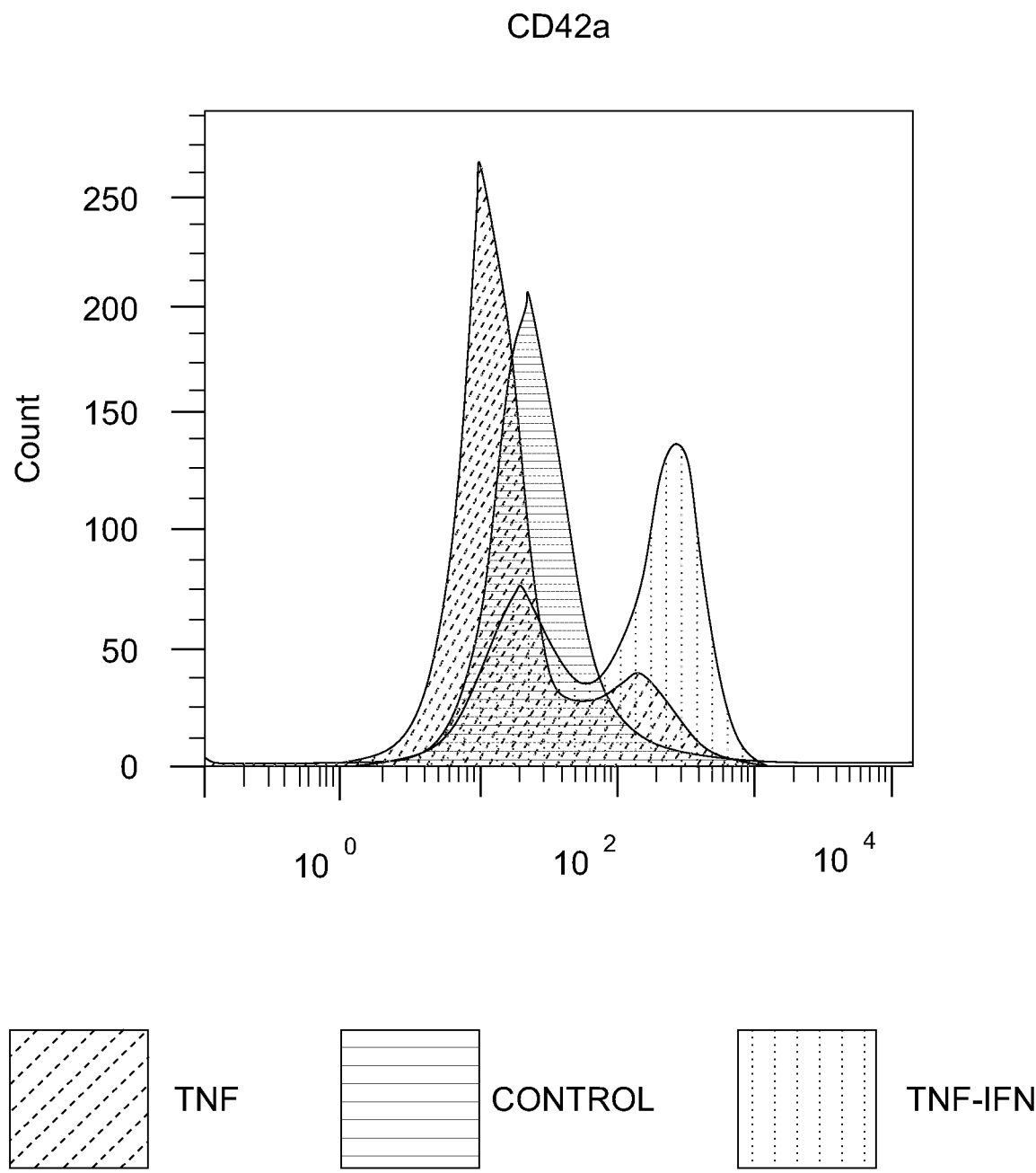
Figure 12E:
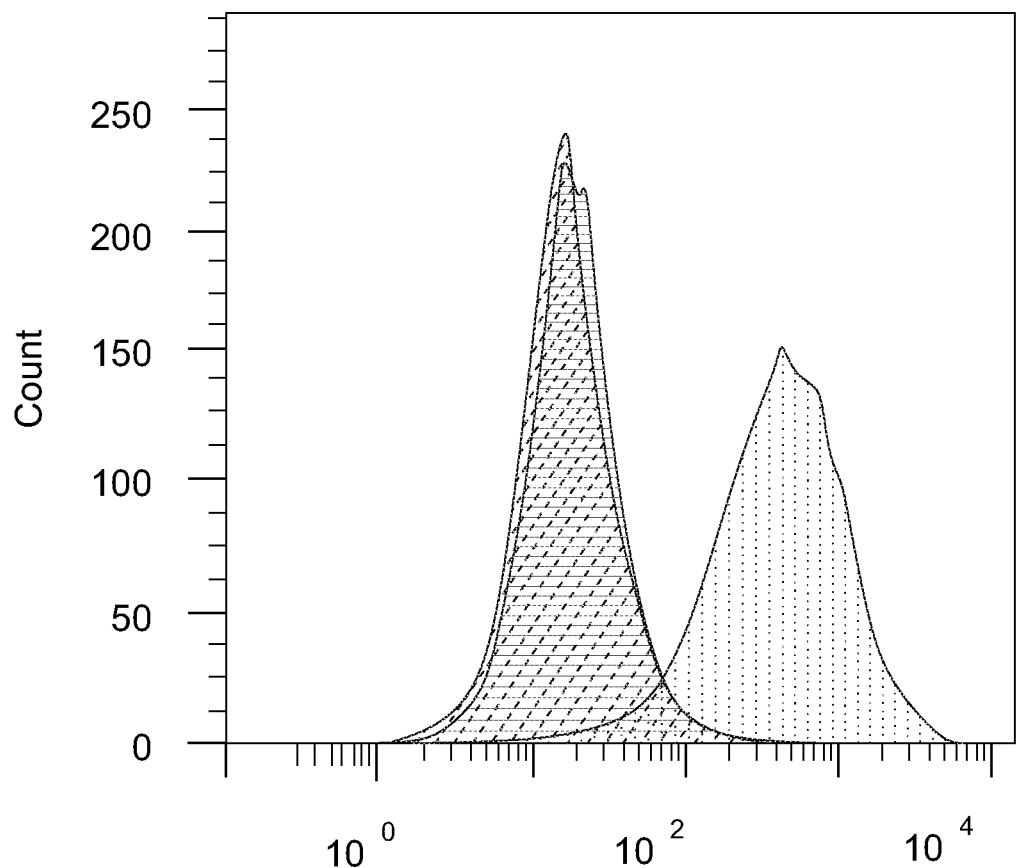
Figure 12G:
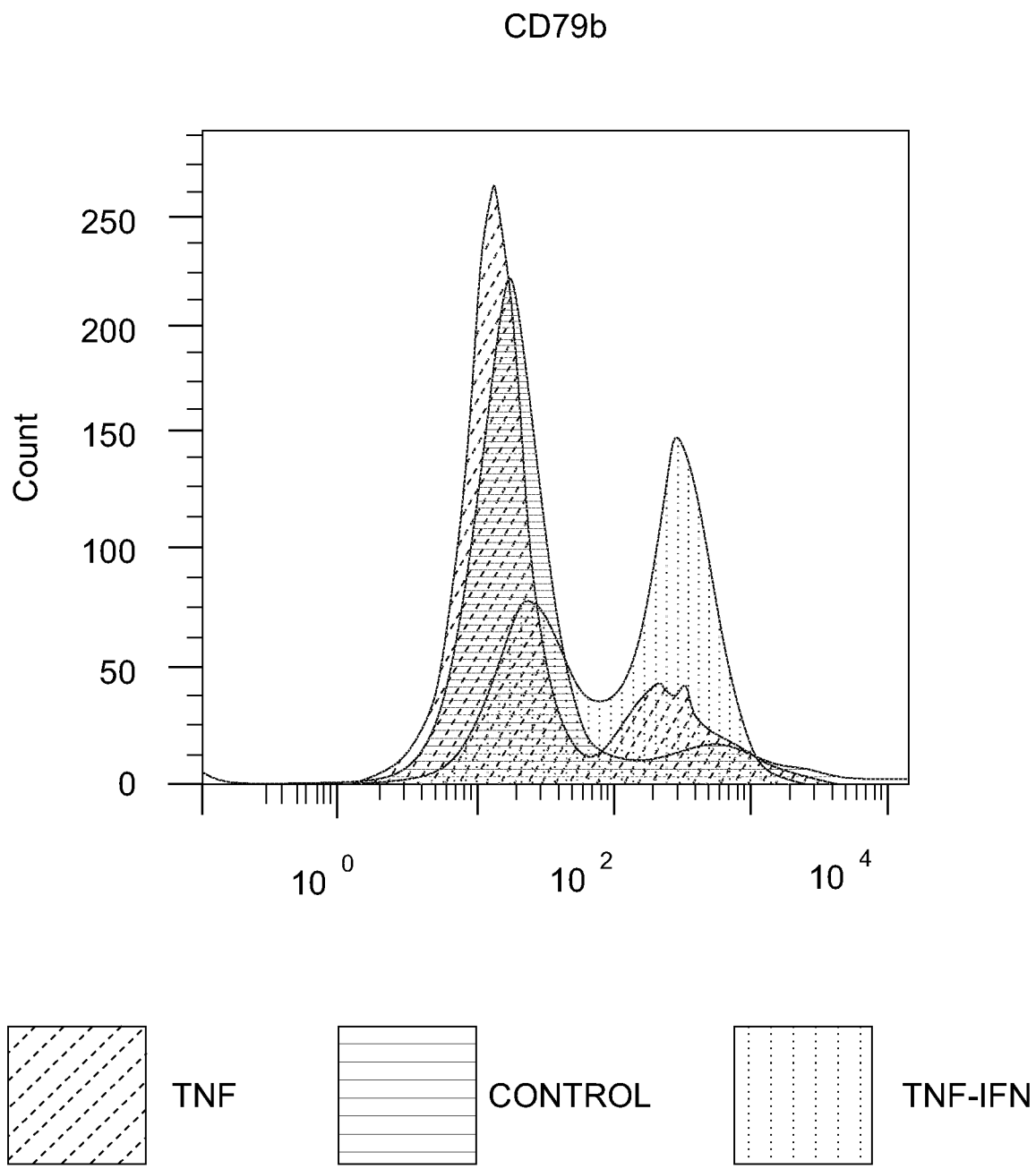
Figure 12H:
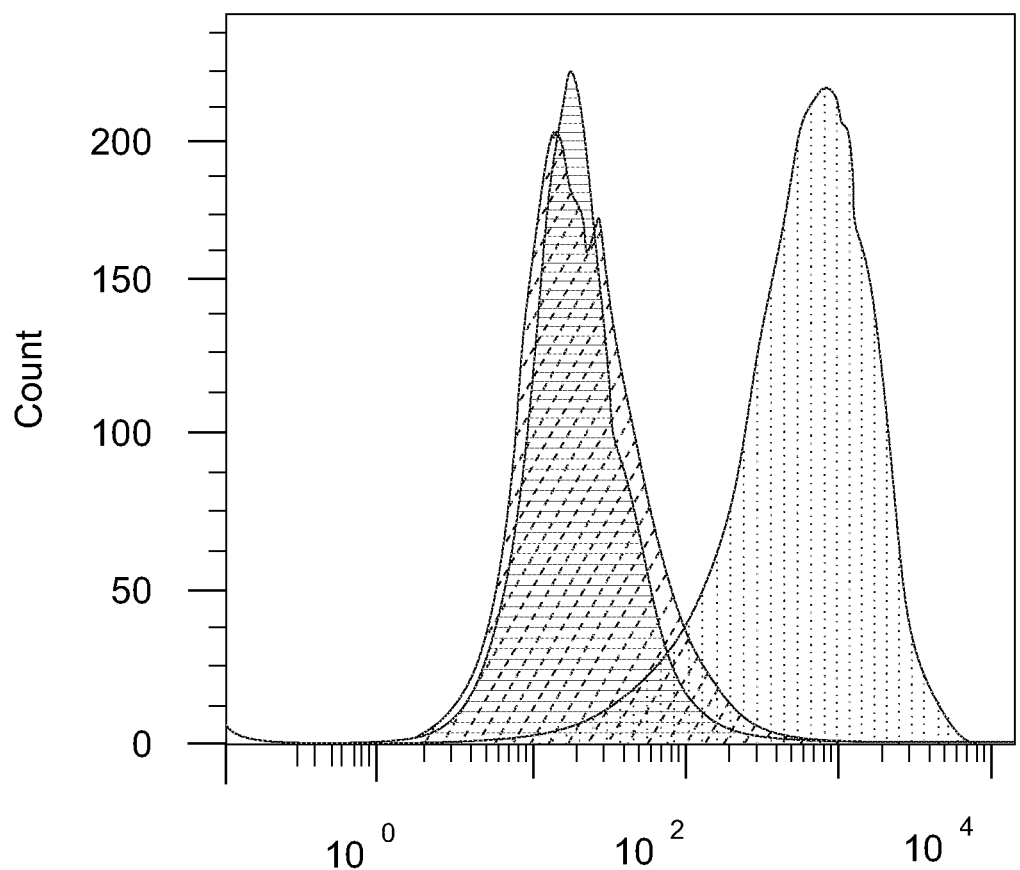
Figure 12J:
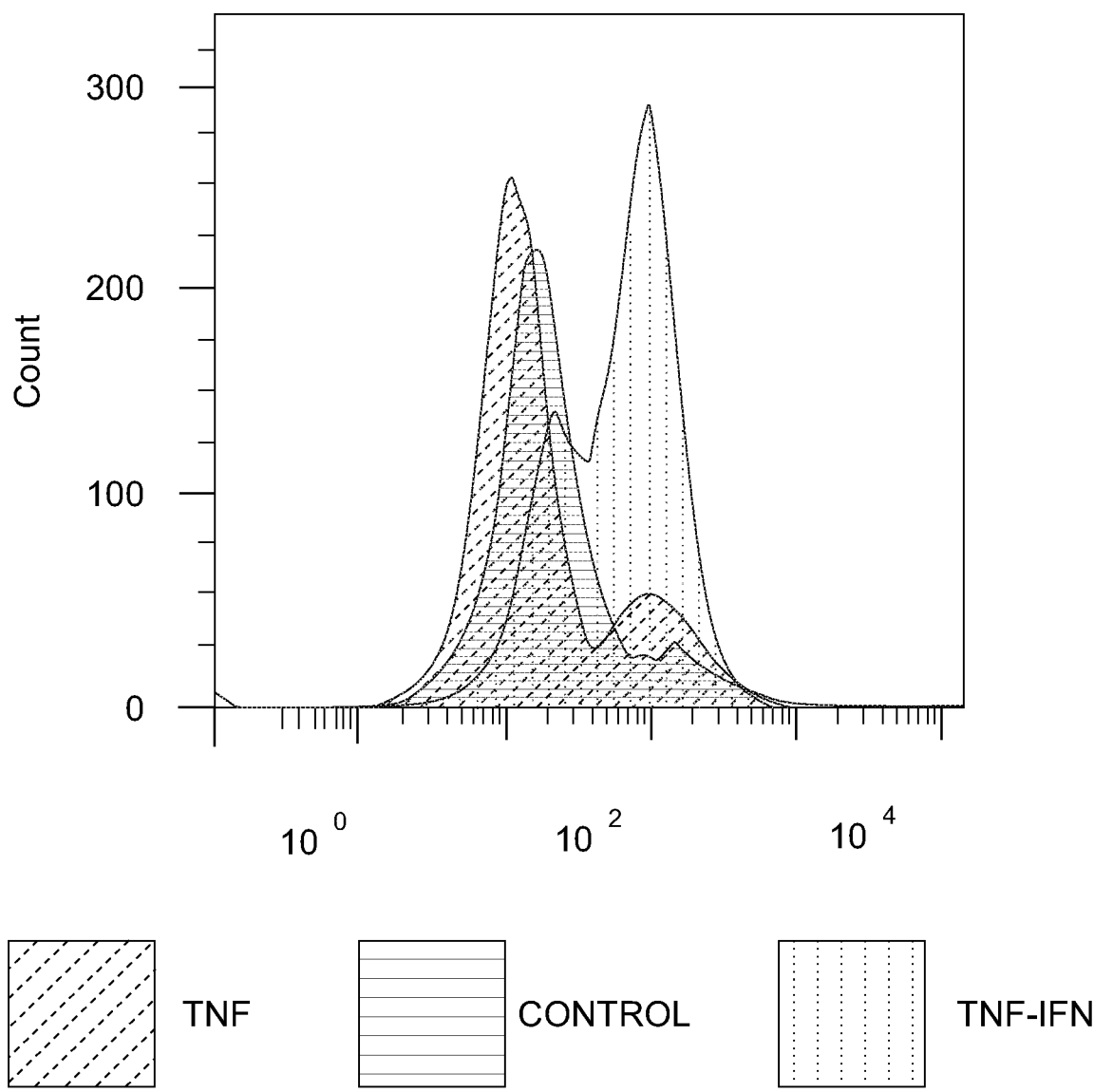
Figure 12K:
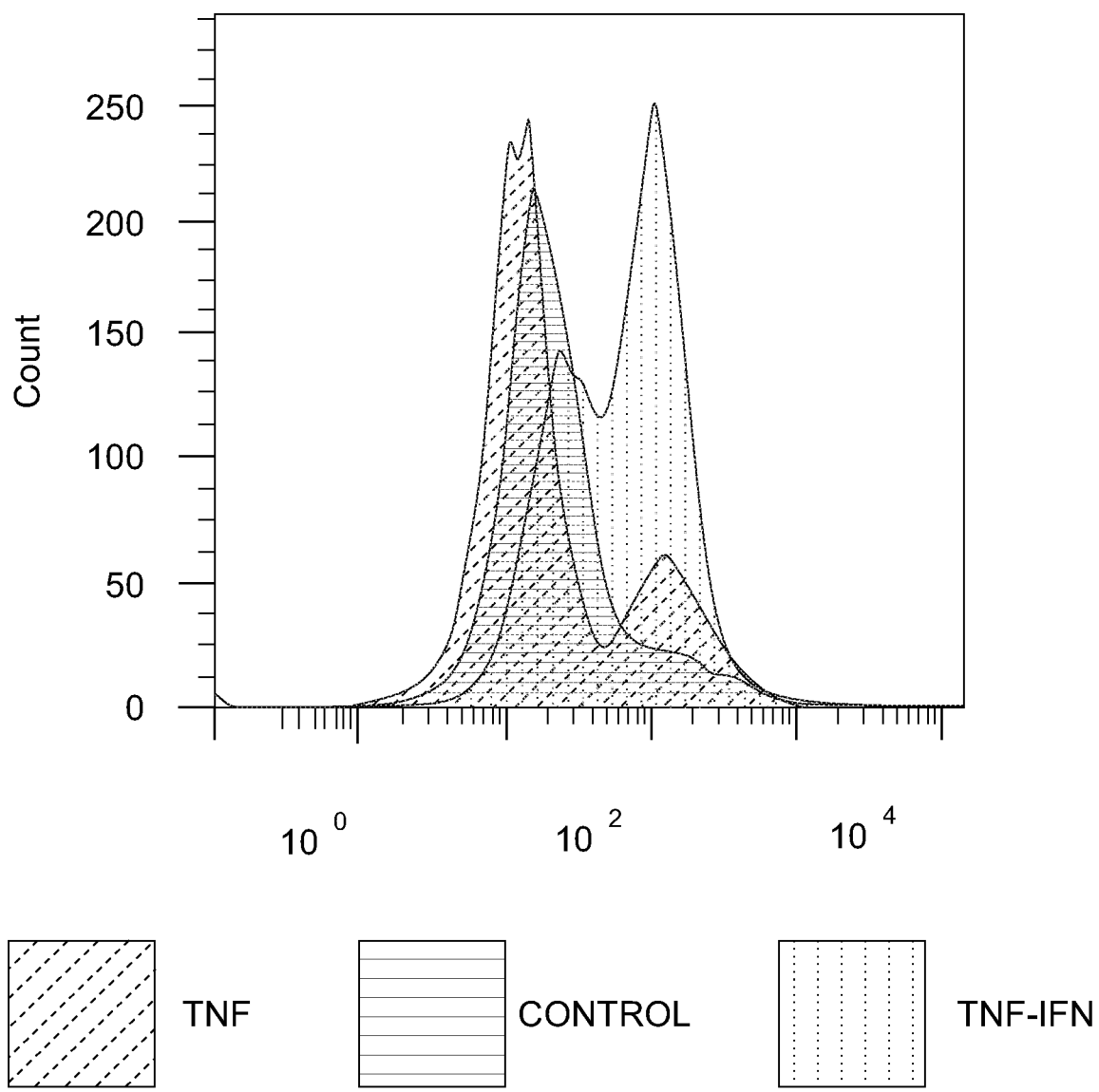
Figure 12L:
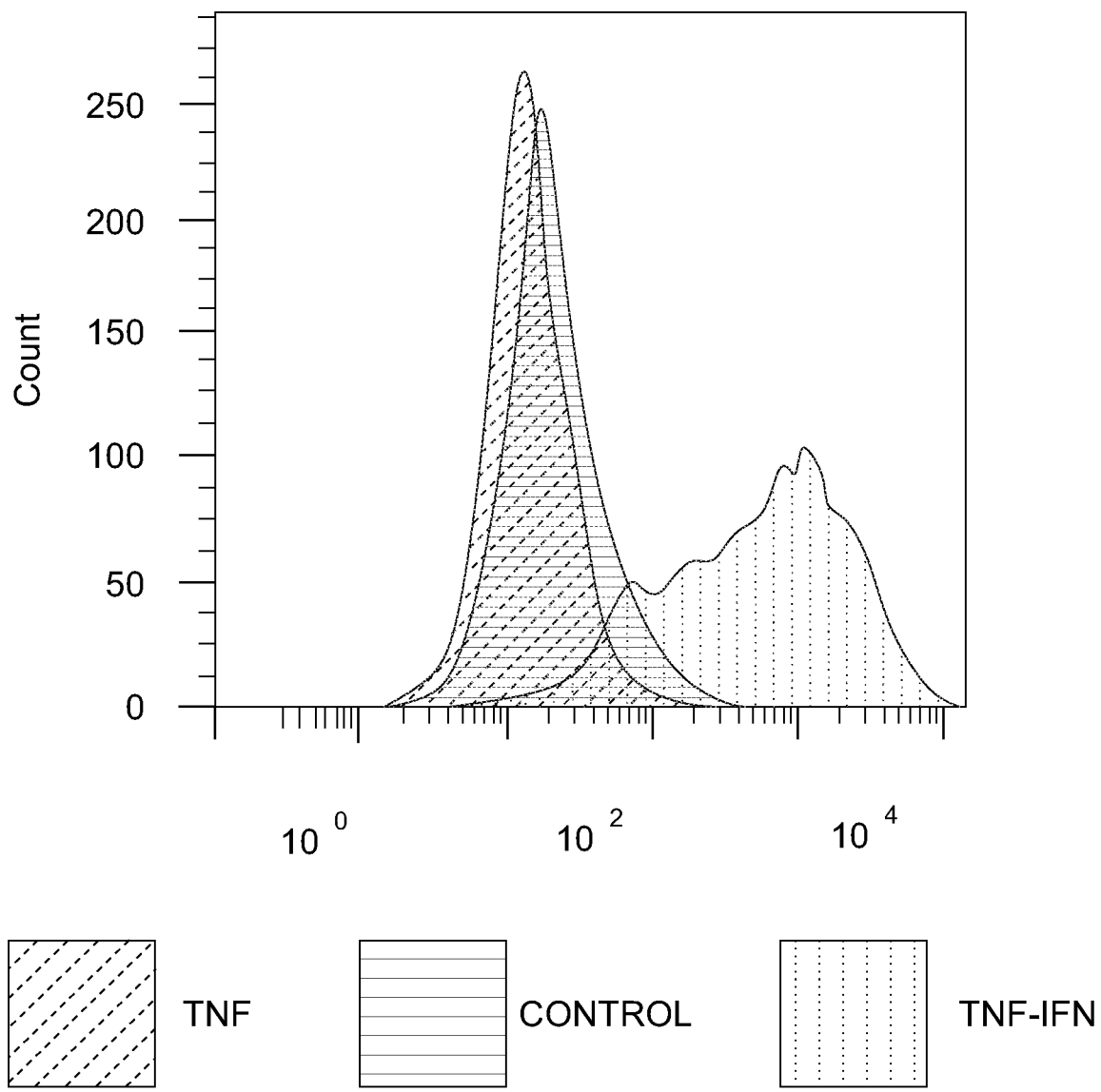

Increased expression of MCP-1 and GM-CSF in the bioreactor media was verified by quantitative ELISA in several experiments, all performed in the absence of serum. The results showed that TNF-alpha+IFN-gamma was superior to TNF-alpha alone for MCP-1 induction (FIG. 8A), while TNF-alpha alone appeared to be slightly superior for GM-CSF induction (FIG. 8B). The cytokine concentrations and fold-changes relative to control medium (containing no cytokines) from the TNF-alpha+IFN-gamma trial are shown in Table 9 below.

TABLE 9

MCP-1 and GM-CSF concentrations in bioreactor medium.

| Expt. No. | Conditions | MCP-1 in pg/ml/ (fold-increase) | GM-CSF in pg/ml/ (fold-increase) |
|---|---|---|---|
| 1 | TNF + IFN | 6365.4 (311) | 6.32 (6.9) |
|   | None | 20.5 | 0.91 |
| 2 | TNF + IFN | 9063.7 (1579) | 13.09 (20.0) |
|   | None | 5.8 | 0.65 |

The induction of several other factors, over several experiments utilizing TNF-alpha+IFN-gamma or TNF-alpha alone (all in the absence of serum), was detected by the aforementioned cytokine array. A number of proteins were consistently upregulated, a partial list of which is depicted in Table 10 below.

TABLE 10

Fold-enrichment (relative to no-cytokine control cells) of selected proteins upon incubation with TNF-alpha +/− IFN-gamma. Only fold-changes greater than 2 are depicted.

| Condition/ Expt. No. | TNF + IFN/ expt. 1 | TNF + IFN/ expt. 2 | TNF alone/ expt. 6 |
|---|---|---|---|
| Proteins | | | |
| ENA-78 | 13.0 | 11.4 | |
| GCSF | 4.6 | 3.3 | |
| GM-CSF | 3.7 | 3.1 | |
| GRO | 57.8 | 102.7 | 87 |
| GRO-a | 2.9 | 2.5 | |
| IL-2 | 3.8 | 3.2 | |
| IL-6 | 199.2 | 281.4 | 16.5 |
| IL-7 | 4.6 | 2.5 | |
| IL-8 | 32.6 | 80.5 | 88.7 |
| IL-10 | 3.2 | 3.5 | |
| IFN-g | 2.9 | 2.8 | |
| MCP-1 | 88.3 | 529.3 | 243.3 |
| MCP-2 | 88.3 | 198.5 | |
| MCP-3 | 160.7 | 18.0 | 10.4 |
| MIG | 158.2 | 3.2 | |
| RANTES | 4.4 | 452.1 | 41.3 |
| TGF-b1 | 256.7 | 3.5 | |
| VEGF | 4.3 | | |
| Eotaxin | 17.6 | 2.1 | |
| IGFBP-2 | 2.3 | | 2.8 |
| IP-10 | 75.0 | 94.7 | |
| MIF | 3.0 | 2.9 | |
| Angiogenin | | | 2.7 |
| Osteopontin | | | 2.5 |
| Osteoprotegerin | | | 4.6 |

Example 8: The Effect of Serum on Pro-Inflammatory Cytokine Treatment of ASC During 3D Culturing This experiment examined the effect of FBS on induction of the aforementioned panel of factors by TNF-alpha+IFN-gamma (FIG. 9A) or TNF-alpha alone (FIG. 9B) in a bioreactor. A similar set of major proteins was induced in the presence or absence of FBS. In the case of TNF-alpha alone, IL-6 was induced much more strongly in the presence of FBS than in its absence, while TNF-a+IFN-g provided even stronger induction than TNF-a+FBS. FIGS. 9 C-E depict secreted protein concentration, in units of pg/ml, of various factors by unstimulated cells or cells stimulated with TNF-a alone or TNF-a+IFN-g.

Example 9: Immunomodulatory Effect of ASC Pre-Treated with Pro-Inflammatory Cytokines Methods—PBMC IL-10 Secretion Assay On day 1, 150,000 untreated ASC, pre-treated ASC, or control medium (no cells), in a volume of 150 microliters (mcL) were seeded in wells of a 48-well plate and were incubated overnight. On day 2, 50,000 human PBMC in a volume of 100 mcL were seeded into the wells containing ASC or control medium. On day 3, 1.5 micrograms (mcg) of LPS in 50 mcL medium was added to the cells, and the cells were incubated for 5 hours at 37° C. Cell-free supernatants were collected from the wells, and ELISA was performed using the Quantikine® ELISA Human IL-10 kit.

Results

This experiment examined the effect of the pre-treated ASC on LPS-induced IL-10 secretion from PBMC. The IL-10 secretion elicited by pre-treated ASC was higher than untreated ASC.

Example 10: Additional Quantitative RANTES ELISA Assays on Pre-Treated ASC

ASC were incubated with 10 ng/ml TNF-alpha, alone or in combination with 10 ng/ml IFN-gamma, as described for Example 7. The cells were cryopreserved, then thawed, and then $5 \times 10^5$ cells were seeded in DMEM supplemented with 10% FBS and incubated under standard conditions. After 24 hours, the medium was replaced with 1-ml serum-free medium, and the cells were incubated another 24 hours under normoxic conditions. The medium was removed and assayed for RANTES secretion by ELISA, using the Quantikine® ELISA Human CCL5/RANTES kit (R&D Systems). The TNF-alpha+IFN-gamma-treated cells had sharply upregulated RANTES secretion compared to the other groups (Table 11). In a similar experiment, TNF-alpha+IFN-gamma treatment was tested in parallel with TNF-alpha alone, IFN-gamma alone, or no treatment. The average RANTES expression was more than 10-fold higher in the TNF-alpha+IFN-gamma-treated cells than any other group (FIG. 10).

TABLE 11

RANTES concentrations in culture medium in pg/ml.

| Expt. No. | Conditions | RANTES conc. | Standard dev. |
| --- | --- | --- | --- |
| 5 | No cytokines, no serum | 0 | 0 |
| 7 | No cytokines, serum. | 1 | 1 |
| 8 | No cytokines, serum | 0 | 0 |
| 5 | TNF-alpha, no serum | 75 | 2 |
| 7 | TNF-alpha, serum. | 577 | 20 |
| 8 | IFN-gamma + TNF-alpha + serum. | 3173* | 83 |

*Out of calibration curve.

Example 11: Global Gene Expression Array of Treated ASC

A global gene expression array was performed on ASC treated with inflammatory cytokines, as described for Example 7. 610 and 130 genes were differentially expressed (at least 1.5-fold change), relative to untreated cells, in cells treated with TNF-alpha+IFN-gamma or TNF-alpha alone, including 100 genes shared between the 2 samples.

Example 12: QRT-PCR Gene Expression Assays of ASC Treated with TNF-Alpha, IFN-Gamma, or TNF-Alpha+IFN-Gamma qRT-PCR assays were performed to measure the expression of selected proteins in placental cells either not treated with cytokines or treated with TNF-alpha and/or IFN-gamma, as described for Example 7. IDO1 (FIG. 11A), IL18BP (FIG. 11B), MCP1/CCL2 (FIG. 11C), IL1beta (FIG. 11D), HLA-DR (FIG. 11E), CD106 (VCAM) (FIG. 11F), and MMP3 (FIG. 1G) were upregulated, while IGFBP5 (FIG. 11H) and RGS4 (FIG. 11I) were downregulated in cytokine-treated cells. In many cases, the combination of the 2 cytokines greatly enhanced the effect.

Enhancement of RANTES secretion was also observed when an additional quantitative ELISA assay was performed for RANTES. The results are shown in Table 12.

TABLE 12

Additional RANTES ELISA results.

| Human | RANTES conc. (pg/ml) | STDEV |
| --- | --- | --- |
| No cytokines, FBS present. | 1 | 1 |
| No cytokines, FBS present. | 6 | 1 |
| No cytokines. FBS present | 2 | 1 |
| No cytokines, FBS present. | 0 | 0 |
| TNF-alpha. FBS present | 594 | 58 |
| TNF-alpha. FBS present. | 888 | 35 |
| TN-gamma. FBS present | 7 | 2 |
| TN-gamma. FBS present. | 45 | 5 |
| TNF-alpha + IFN-gamma. FBS present. | 35932 | 1224 |
| TNF-alpha + IFN-gamma. FBS present | 41896 | 419 |
| TNF-alpha + IFN-gamma. FBS present | 18662 | 874 |
| TNF-alpha + IFN-gamma. FBS present. | 34843 | 2272 |
| TNF-alpha + IFN-gamma. FBS present. | 46561 | 427 |

Example 13: Immune-Phenotype of ASC Treated with Inflammatory Cytokines

The immune-phenotype of the ASC that had been pre-treated with pro-inflammatory cytokines, as described for Example 7, was examined over several experiments. Consistently, the cells were over 90% positive for CD29, CD90, and CD54; over 85% positive for CD73 and CD105; and over 65% positive for CD49. Additionally, the cells were less than 1% positive for CD14, CD19, CD31, CD34, and CD39; less than 3% were positive for CD200; less than 6% were positive for GlyA; and less than 20% were positive for SSEA4.

In a separate set of experiments, expression of a panel of markers was compared between untreated cells and cells treated with TNF-alpha alone or TNF-alpha+IFN-gamma. Differences were found in treated relative to untreated cells in expression of CD9, CD26, CD38, CD40, CD42a, CD45RA, CD49f, CD56, CD66acde, CD74, CD77, CD79b, CD106, CD107a, CD107b, CD120a, CD162, CD243, CD274, CD275, CD282, CD326, and HLA-DR. The negative control and other representative plots (CD9, CD38, CD42a, CD74, CD77, CD79b, CD106, CD107a, CD243, CD275, and HLA-DR) are shown in FIGS. 12A-L.

Example 14: Altered Cytokine Treatment Conditions Improve Cell Vitality

ASC were stimulated with inflammatory cytokines in a similar manner to that described in Example 7, with two exceptions: 1. The cytokine exposure was for 24 hrs; and 2. Cytokines were spiked into the bioreactor medium, using a concentrated stock solution at the beginning of the 24-hr incubation, thus rapidly bringing the cytokine concentration up to the target concentration. Over the following 24 hours, fresh medium containing the target cytokine concentration was perfused into the bioreactor. The 24-hr incubation began 5 days after seeding the bioreactor, corresponding to exponential growth phase. By the conclusion of cytokine treatment, cellular growth had reached the point that the rate of doubling began to slow. The ASC were frozen. Thawed cells were seeded on tissue culture dishes, and population doubling time (PDT) was measured, by measuring and comparing cell densities in plates harvested 3 and 4 days after seeding.

Figure 13:
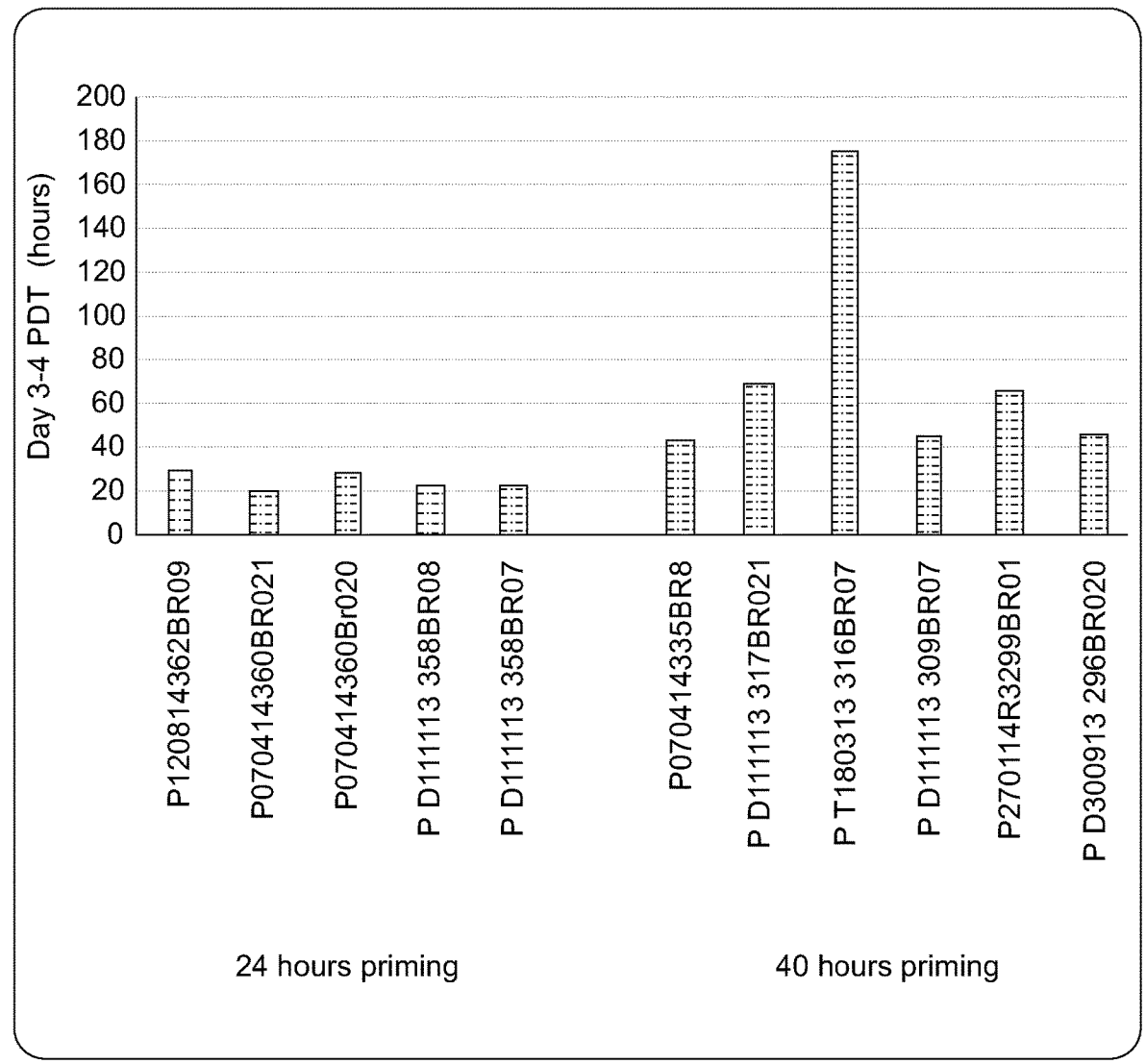
FIG. 13 is a plot showing population doubling time (PDT; vertical axis), in cells stimulated in a bioreactor with various concentration of cytokines (indicated in Table 13) for 40 hrs. (leftmost 7 groups) or 24 hrs. (rightmost 5 groups).

The 24-hr-stimulated cells exhibited a significant reduction in PDT (FIG. 13). Table 13 sets forth the conditions of each sample.

TABLE 13

Conditions of samples depicted in FIG. 13.

| Run | TNF/IFN concentration | Hours exposure | PDT |
|---|---|---|---|
| 277BR021 PT180313 | 10/10 | 40 | 49.7 |
| 296BR020 PD300913 | 10/10 | 40 | 74.2 |
| 299BR01 P270114R3 | 10/10 | 40 | 67.2 |
| 309BR07 PD111113S6 | 10/10 | 40 | 55.5 |
| 316BR07 PT180313 | 10/10 | 40 | 126.5 |
| 317BR021 PD111113S7 | 10/10 | 40 | 83 |
| 335BR08 P070414 | 10/10 | 40 | 95.2 |
| 358BR07 PD111113 | 10/10 | 24 | 19 |
| 358BR08 PD111113 | 1/1 | 24 | 19.3 |
| 360BR020 P070414 | 5/5 | 24 | 24.7 |
| 360BR021 P070414 | 10/10 | 24 | 19.4 |

Figure 14A:
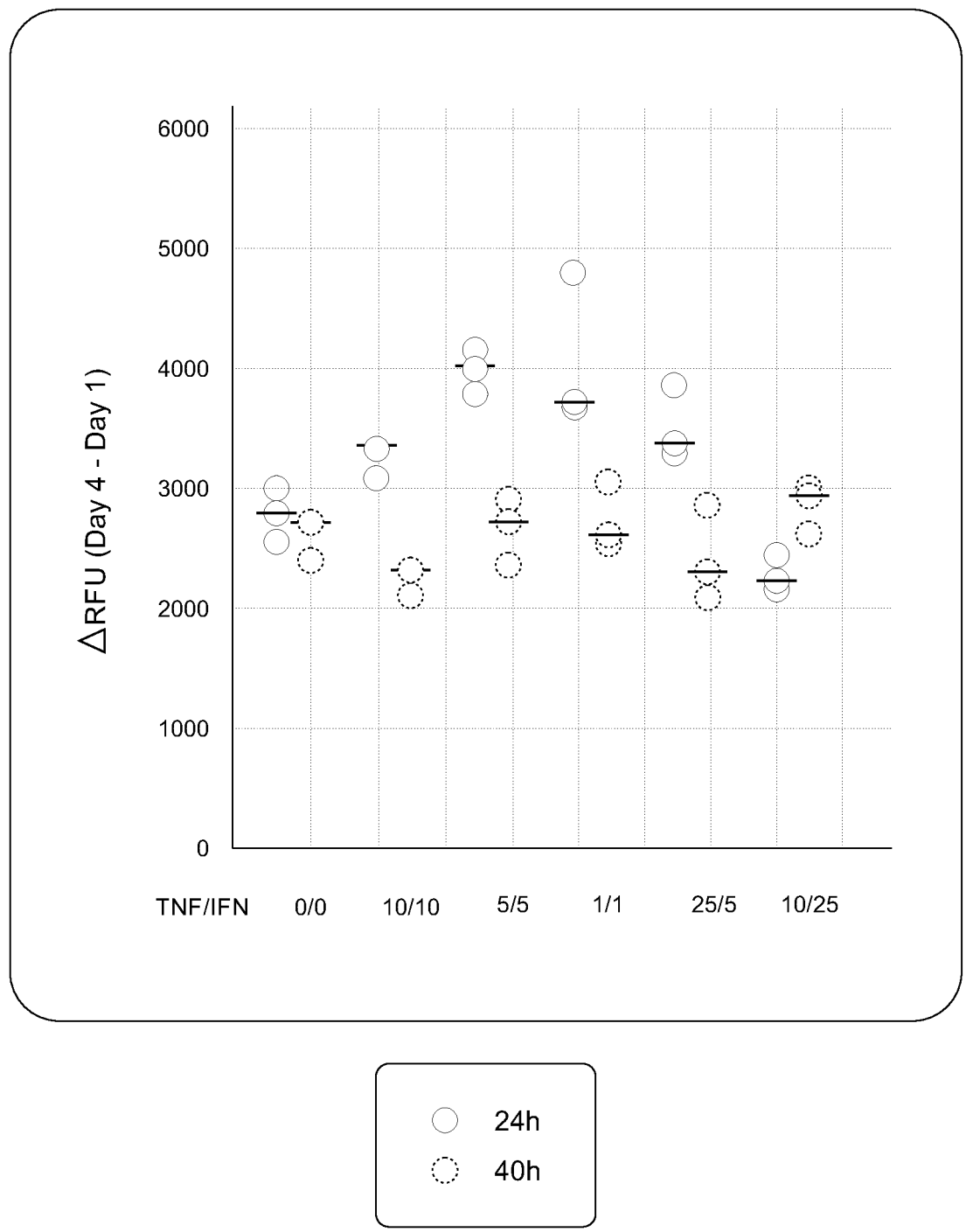
FIG. 14A is a plot showing change in relative Cyquant® fluorescence units (RFU; vertical axis) in cells stimulated with various concentration of cytokines (indicated on the horizontal axis), for 40 (dotted circles) or 24 (solid circles) hrs. Cyquant® fluorescence is proportional to DNA quantity and thus cell number, reflecting post-thaw cell growth. B-C are bar graphs showing induction of CCL2 (horizontal hatching), IL1B (vertical hatching), and IL-6 (unfilled) after stimulation for 24 hrs. (B) or 40 hrs (C), expressed as fold-change relative to the no cytokine group (vertical axis). D is a plot of post-thaw viability (vertical axis) after stimulation with various concentrations of TNF-a and IFN-g, whose respective concentrations are shown on the horizontal axis.
Figure 14B:
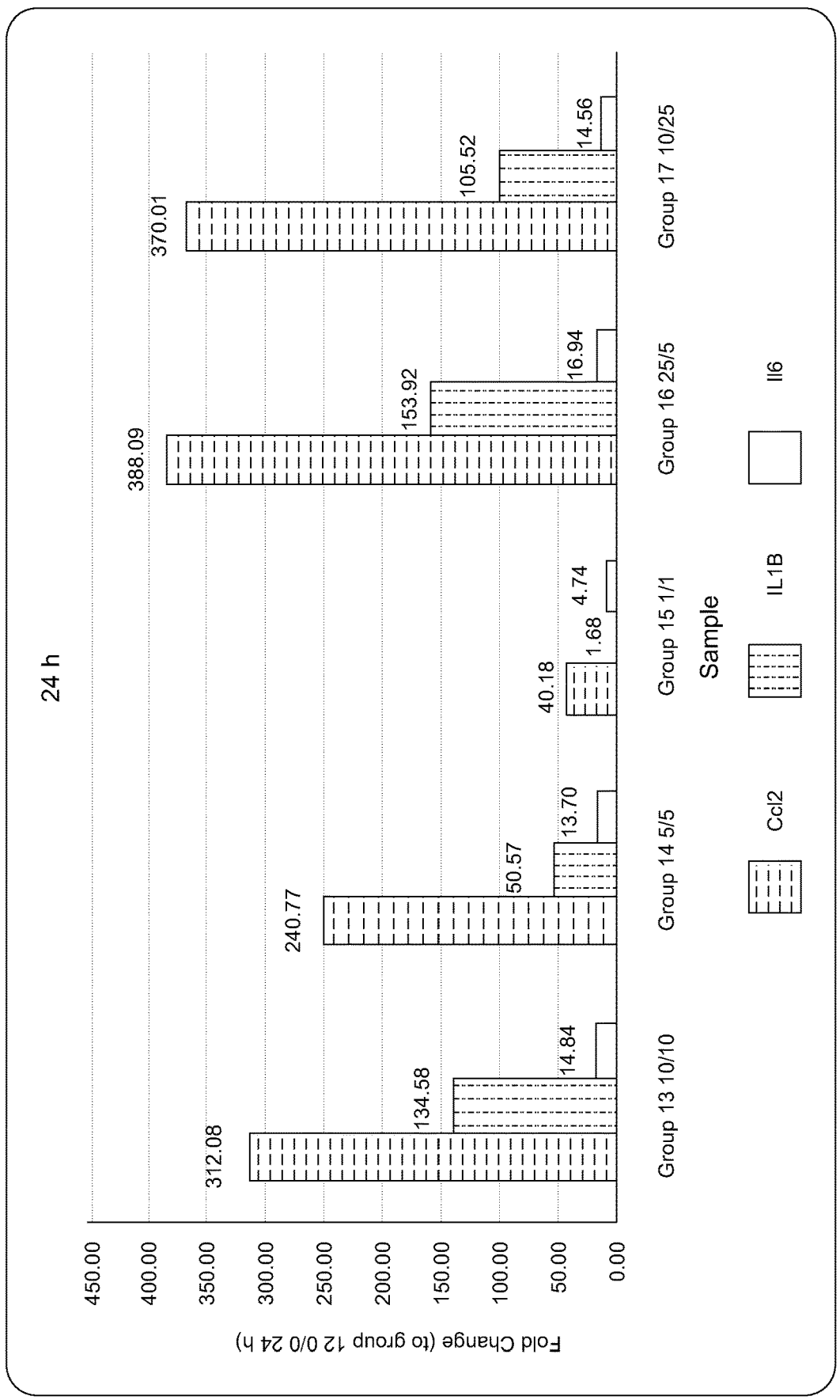
Figure 14C:
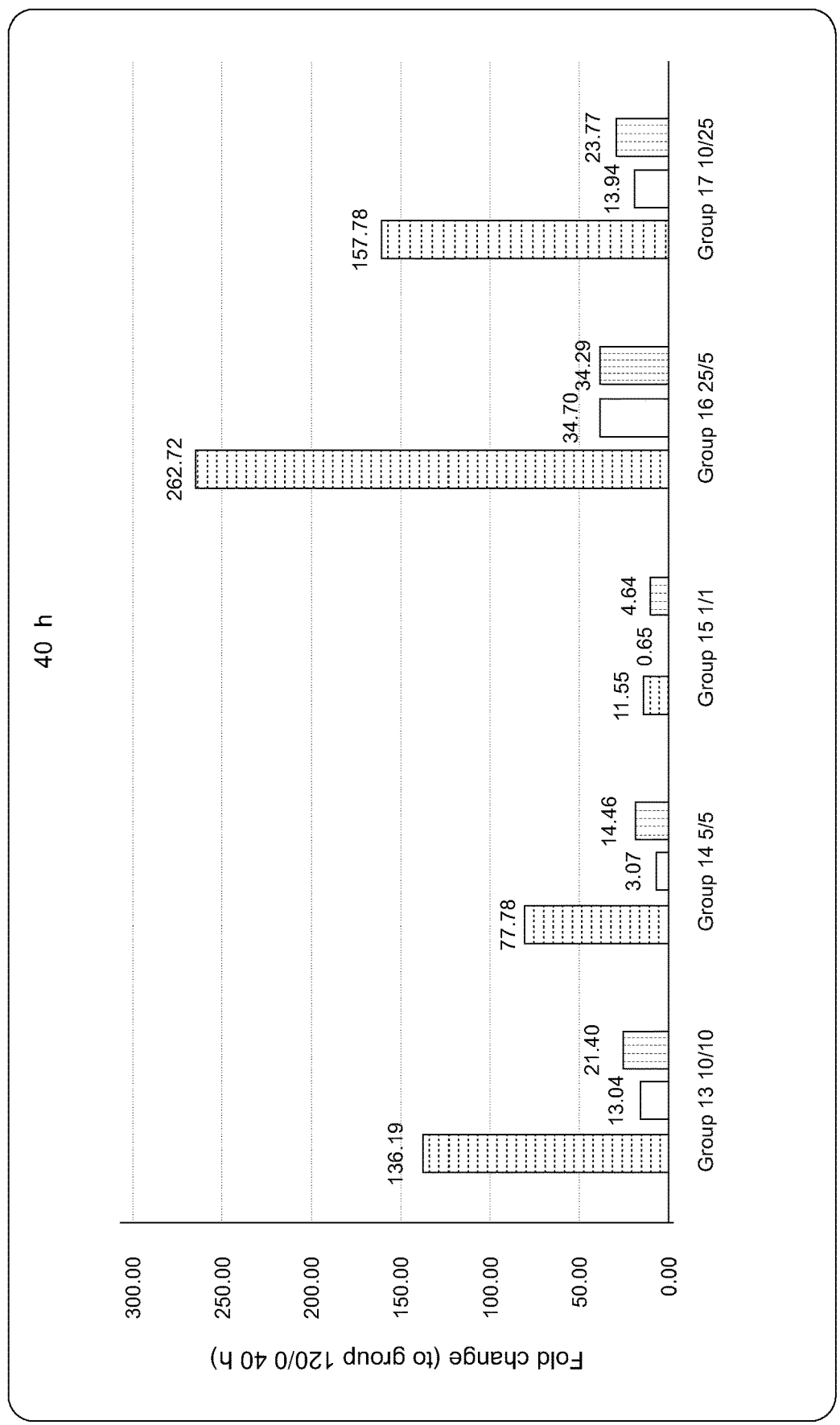
Figure 14D:
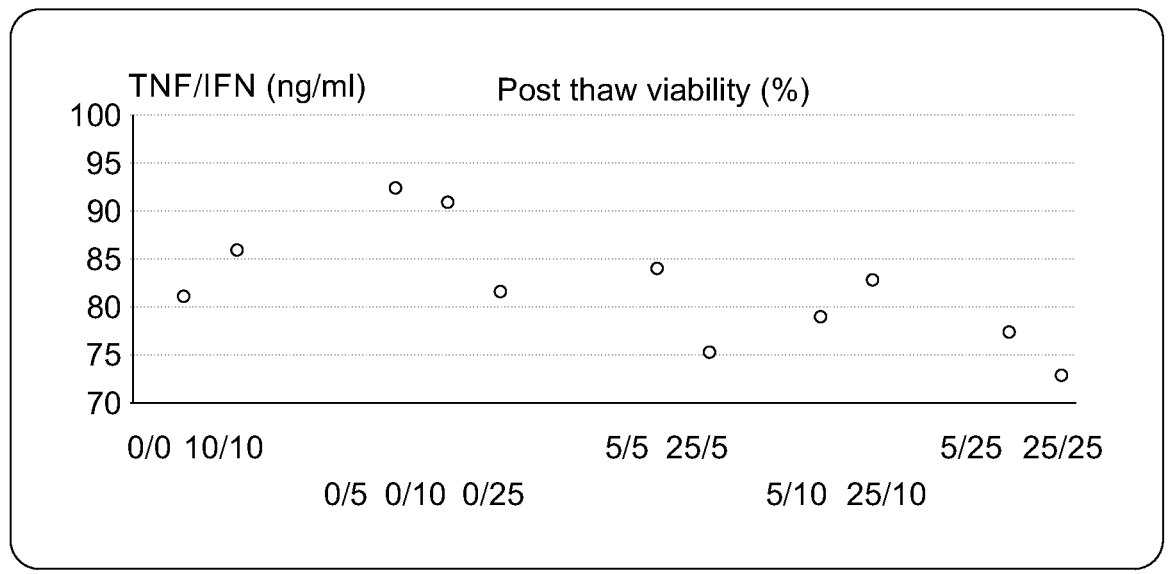

Example 15: Cytokine Treatment of ASC for 24 Hrs. Preserves Upregulation of Genes Induced by Cytokine Treatment Next, a head-to-head experiment was performed to complement the data from the previous Example. Cells from the end of Step 2-1 (this corresponds to the last step before bioreactor seeding see Example 1) were seeded in tissue culture dishes. 72-96 hours later, corresponding to exponential growth phase, cytokines were added to the dishes. Cells were then frozen, thawed, and again seeded in flasks for the aforementioned growth assay. Once again, cells exposed to cytokines for 24 hours exhibited superior vitality, as evidenced by their replication (FIG. 14A), while retaining upregulation of CCL2, IL1B, and IL6 (FIGS. 14B-C). Cells exposed to various concentration of cytokines retained post-thaw viability of over 70% (FIG. 14D).

Figure 15:
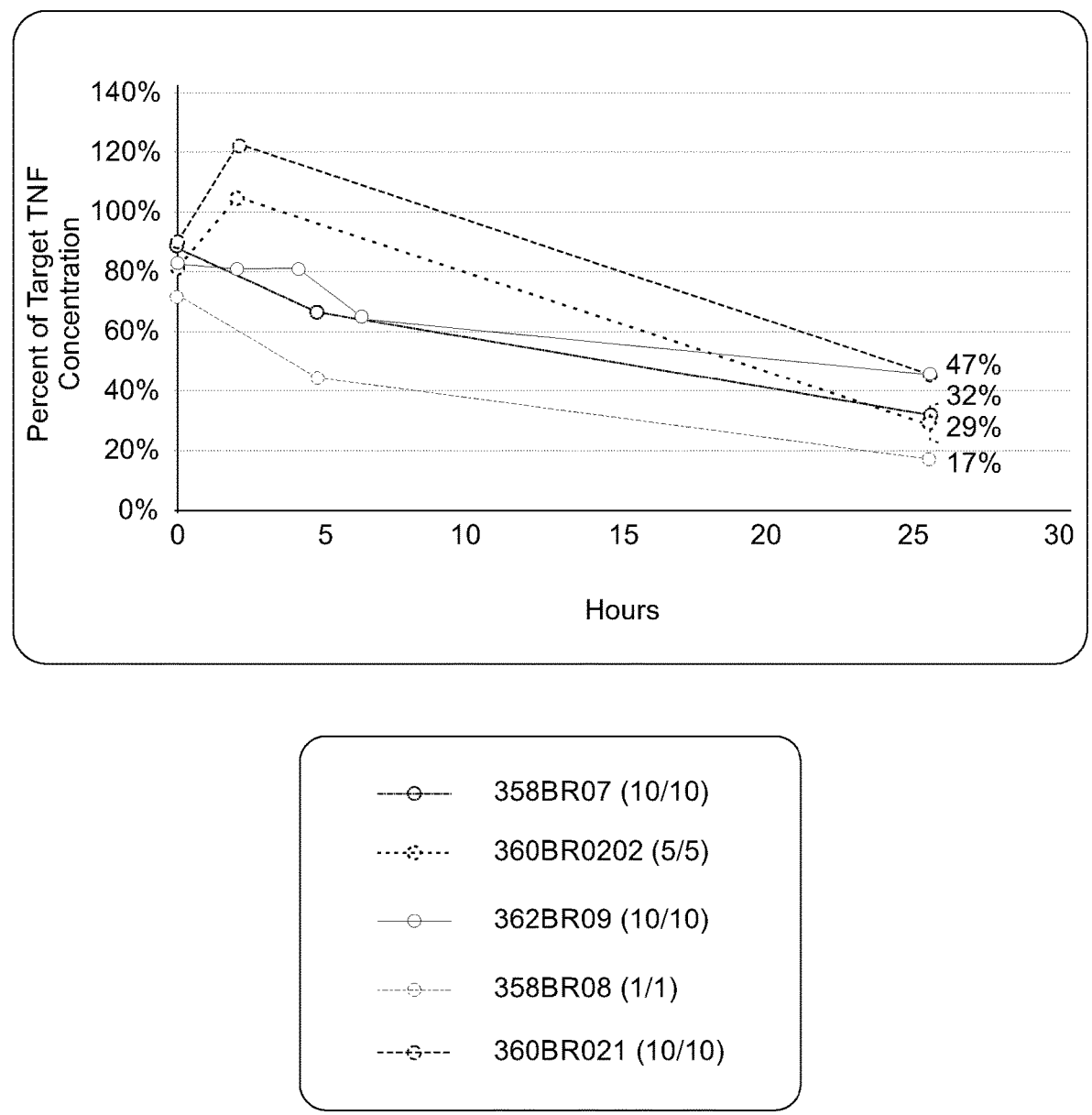
FIG. 15 is a plot showing TNF-alpha concentrations in the bioreactor at various time points during a bioreactor run, in 3 different runs given 10, 5, or 1 ng/ml each of IFN-g and TNF-a. Data groups are indicated in the figure.

Example 16: Differences Between Cytokine Concentrations Observed in the Feed Bag and the Bioreactor In this experiment, a bioreactor run was performed as described in Example 14. Although the feed bag holding the (cytokine-containing) medium was kept at 4° C., TNF-alpha concentrations in the bioreactor were reduced to 17%-47% of the original value (FIG. 15).

Example 17: Use of Pre-Treated ASC in Treating IBD

ASC pre-stimulated with TNF-a and IFN-g are tested in an animal model of inflammatory bowel disease (IBD), e.g. Crohn's disease or ulcerative colitis, for example by addition of dextran sodium sulfate (DSS; e.g. 0.5%, 1%, 2%, or 3%) to drinking water of (Muc2−/−) mice or another animal, for example as described in Heazlewood et al 2008 and the references cited therein; or by a rectal instillation of dinitrobenzensulfonic acid (DNBS) into rats or another animal, for example as described in Harel et al 2011 and the references cited therein. In still other experiments, human subjects with IBD are administered the described cells.

Example 18: Use of Pre-Treated ASC in Treating DTH

ASC pre-stimulated with TNF-a and IFN-g are tested in an animal model of an adaptive immune system-mediated inflammatory disorder, such as Delayed-Type Hypersensitivity (DTH). For example, DTH may be measured by inducing allergic contact dermatitis (ACD), for example by application of chemicals such as sodium lauryl sulfate, benzalkonium chloride, or croton oil, followed by subsequent application of the same chemical and assessment of inflammatory sequelae such as an eczematous skin reaction. This may be done, for example, for example as described in Martin S F 2013 and the references cited therein. In other experiments, another inflammatory substance is introduced into the soft tissue of a subject, to simulate another inflammatory disorder. In still other experiments, human subjects with an inflammatory disorder are administered the described cells.

Example 19: Use of Pre-Treated ASC in Treating CP/CPPS

ASC pre-stimulated with TNF-a and IFN-g are tested in an animal model of an innate immune system-mediated inflammatory disorder, such as non-bacterial chronic prostatitis (CP/CPPS). For example, CP/CPPS can be induced by injection of carrageenan into the prostate, for example as described in Chen C S et al 2013 and the references cited therein. In other experiments, another innate immune system-mediated inflammatory disorder is simulated in an experimental subject. In still other experiments, human subjects with an innate immune system-mediated inflammatory disorder are administered the described cells.

Example 20: Use of Pre-Treated ASC in Treating NMO

ASC pre-stimulated with TNF-a and IFN-g are tested in an animal model of neuromyelitis optica (NMO). For example, NMO can be induced by introduction of NMO-inducing antibodies into rat brains, for example anti-aquaporin 4 (AQP4) antibodies, with or without complement. This may be done, for example, using either systemic transfer (for example after induction of experimental autoimmune encephalomyelitis (EAE), which can be induced for example by administration of preparations of Myelin Oligodendrocyte Glycoprotein with adjuvant) or intracranial injection, as described in Saadoun S et al 2010, Saini H et al 2013, Wrzos et al 2014, Tradtrantip et al 2013, and Tradtrantip et al 2014; and the references cited therein. ASC are administered to the rat, for example intracerebrally at the same time as the NMO-inducing antibodies, or in other experiments intracranially, intramuscularly, intravascularly, or intravenously. Progression and severity of NMO is in some experiments determined by loss or damage of oligodendrocytes, oligodendrocyte precursor cells, and/or astroglial cells, or loss of glial fibrillary acidic protein (GFAP), AQP4, neurofilament (NF) or myelin from CNS tissue, or the presence of CD45-positive lymphocytes, ionized calcium-binding adaptor molecule-1 (Iba1), or activated complement (detectable by C9neo immunostaining), or by measuring plasma levels of human and rat inflammatory cytokines, such as IL-2 or IL-6; for example as described in the above references.

In some experiments, optic neuritis (ON) is induced, for example by introduction of NMO antibodies by retrobulbar infusion, intravitreal injection, or intracranial injection near the optic chiasm, for example as described in Asavapanumas N et al 2014; or by the use of myelin oligodendrocyte glycoprotein-specific (MOG-specific) TCR transgenic animals, for example as described in Bettelli El et al 2006. The severity of ON is determined in some experiments by detection of meningeal and/or parenchymal inflammatory lesions in the optic nerves, for example as described in the above references.

In still other experiments, human subjects with NMO and/or ON are administered the described cells.

Example 21: Use of Pre-Treated ASC in Treating Scleroderma

ASC pre-stimulated with TNF-a and IFN-g are tested in an animal model of scleroderma. For example, scleroderma can be induced in mice by repeated (approximately 24 doses over 4 weeks) subcutaneous injection of bleomycin (BLM), for example 100 mcg BLM/dose in saline solution. This may be done, for example, as described in Yamamoto T et al 1999, Yamamoto T et al 2005, Avouac J et al, 2013; and the references cited therein. The animals are administered either carrier or pre-stimulated ASC, for example by intramuscular injection on days 14 and 21 (or in other experiments on days 1 and 7), where day 1 refers to the first BLM injection. Progression and severity of scleroderma is in some experiments determined by assessing dermal fibrosis, as well as optional gross pathological examination to determine systemic fibrosis, for example as described in the above references. Dermal fibrosis may be determined by measuring dermal thickness and/or collagen staining to determine collagen density in the skin, or by measuring TGB-beta RNA levels in skin, by staining.

In still other experiments, human subjects with scleroderma are administered the described cells.

Example 22: Use of Pre-Treated ASC in Treating Limb Ischemia

ASC pre-stimulated with TNF-a and IFN-g are tested in an animal model of limb ischemia, for example by artery and/or vein ligation of mice or another animal, e.g. by the protocol described in Masaki et al 2002 and the references cited therein; or by artery excision of diabetic mice or another animal, for example as described in Huang et al 2012 and the references cited therein. In still other experiments, human subjects with limb ischemia are administered the described cells.

Example 23: Bone Marrow Migration Studies of Pre-Treated ASC

Methods
BM Cell Preparation and Cryopreservation.
Fresh mouse heparinized BM cells were collected from ICR mice (Harlan) into PBS+10% FBS+12.5 units/ml heparin, centrifuged, and washed in PBS. The cells were resuspended in 10 ml fresh chemotaxis buffer (RPMI with 0.5% albumin) and frozen at a concentration of $10 \times 10^6$ cells/ml.
CM Preparation.
Frozen ASC were thawed in full DMEM medium (Gibco) and diluted to a final cell concentration of $0.5 \times 10^6$ cells/4 ml DMEM medium. $0.5 \times 10^6$ cells per well were seeded in duplicate wells in a 6-well plate and incubated for 24 hours at 37° C., 5% C02, 21% 02. Cells were washed with PBS and incubated for 24 hours in 1 ml chemotaxis buffer per well. The CM from the duplicate wells was pooled and cleared by centrifugation, and the supernatant was retained.
BM Seeding.
BM cells were thawed and diluted in chemotaxis buffer to a concentration of $10 \times 10^6$ cell/ml. 100 mcl of the suspension was seeded $1 \times 10^6$ cells) onto the upper case of a 24-well Transwell plate in duplicates. 0.5 ml of CM or chemotaxis buffer only (negative control) was added in duplicates to the lower case of the Transwell plate, and plates were incubated with 5% C02, 95% air, at 37° C. for 24 hrs.

Cell Harvest.
The upper case was removed from each well. The lower cases of each well were mixed, and medium from the duplicate lower case wells were combined. The chemotaxis buffer or CM (with migrated BM cells) was transferred into test tubes. The wells were washed, and the wash was combined with the medium in the test tubes. The cells were centrifuged, the medium was discarded, and the cells were counted using a CyQUANT® NF Cell Proliferation Assay Kit Results
Several batches of ASC pre-treated with cytokines (in the presence of serum) were tested in a bone-marrow migration assay. While all cells showed increased migration relative to the negative control (buffer only), TNF-treated cells exhibited an enhancement in stimulation of migration, and TNF+IFN-treated cells exhibited a stronger enhancement (Table 14).

TABLE 14

Fold enhancement of bone-marrow migration.

| | Fold enhancement from negative control |
|---|---|
| Batch 1: TNF | 2.1 |
| Batch 1: TNF + IFN | 4.1 |
| Batch 1: No cytokines | 1.5 |
| Batch 2: TNF | 2.9 |
| Batch 2: TNF + IFN | 6.2 |
| Batch 2: No cytokines | 1.7 |

Example 24: Pre-Treated ASC for Facilitating HSC Engraftment

ASC pre-stimulated with TNF-a and IFN-g are tested in an animal model of HSC engraftment, for example a murine model that measures engraftment of human cells. Non-limiting examples of such models are described in Wiekmeijer A S et al. and the references cited therein.

Example 25: Use of ASC in Treating Pulmonary Fibrosis

ASC are tested in a culture model of pulmonary fibrosis. C57BL/6 mice are administered a single intra nasal application of bleomycin (BLM) sulfate (0.1 iu BLM/50 µl/mouse), followed 4 hours later by intratracheal administration of $5 \times 10^5$ ASC. The weight of the mice and their lung function is assessed by treadmill performance and oxygen saturation 7, 14, and 21 days afterwards. At 21 days, mice are sacrificed, and lung histology and collagen content are examined.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace alternatives, modifications and variations that fall within the spirit and broad scope of the claims and description. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the invention.

REFERENCES

Additional References are Cited in Text

Asavapanumas N et al, Experimental mouse model of optic neuritis with inflammatory demyelination produced by passive transfer of neuromyelitis optica-immunoglobulin G. J Neuroinflammation. 2014 Jan. 27; 11:16.

Avouac J et al. Critical role of the adhesion receptor DNAX accessory molecule-1 (DNAM-1) in the development of inflammation-driven dermal fibrosis in a mouse model of systemic sclerosis. Ann Rheum Dis 2013; 72:1089-1098.

Bettelli El at al, Myelin oligodendrocyte glycoprotein-specific T and B cells cooperate to induce a Devic-like disease in mice. J Clin Invest. 2006 September; 116(9): 2393-402.

Chen C S et al, Evidences of the inflammasome pathway in chronic prostatitis and chronic pelvic pain syndrome in an animal model. Prostate. 2013 March; 73(4):391-7.

Clayton A et al, Analysis of antigen presenting cell derived exosomes, based on immuno-magnetic isolation and flow cytometry. J Immunol Methods. 2001; 247(1-2): 163-74.

Crescitelli R et al, Distinct RNA profiles in subpopulations of extracellular vesicles: apoptotic bodies, microvesicles and exosomes. J Extracell Vesicles. 2013 Sep. 12; 2.

Dominici et al. Minimal criteria for defining multipotent mesenchymal stromal cells. The International Society for Cellular Therapy position statement. Cytotherapy. 2006; 8(4):315-7.

Harel et al. Enhanced transferrin receptor expression by proinflammatory cytokines in enterocytes as a means for local delivery of drugs to inflamed gut mucosa. PLoS One. 2011; 6(9):e24202.

Huang P H et al. Far infra-red therapy promotes ischemia-induced angiogenesis in diabetic mice and restores high glucose-suppressed endothelial progenitor cell functions. Cardiovasc Diabetol. 2012 Aug. 15; 11:99. doi: 10.1186/1475-2840-11-99.

Heazlewood C K et al. Aberrant mucin assembly in mice causes endoplasmic reticulum stress and spontaneous inflammation resembling ulcerative colitis. PLoS Med. 2008 Mar. 4; 5(3):e54.

Jeon Y J et al, Comparative Analysis of Human Mesenchymal Stem Cells Derived From Bone Marrow, Placenta, and Adipose Tissue as Sources of Cell Therapy. J Cell Biochem. 2016 May; 117(5):1112-25.

Kavanagh D P et al, Pretreatment of Mesenchymal Stem Cells Manipulates Their Vasculoprotective Potential While Not Altering Their Homing Within the Injured Gut. Stem Cells. 2015 September; 33(9):2785-97.

Li H et al, Interferon-γ and tumor necrosis factor-α promote the ability of human placenta-derived mesenchymal stromal cells to express programmed death ligand-2 and induce the differentiation of CD4(+)interleukin-10(+) and CD8(+)interleukin-10(+)Treg subsets. Cytotherapy. 2015 November; 17(11):1560-71.

Martin S F. Induction of contact hypersensitivity in the mouse model. Methods Mol Biol. 2013; 961:325-35.

Masaki I et al. Angiogenic gene therapy for experimental critical limb ischemia: acceleration of limb loss by overexpression of vascular endothelial growth factor 165 but not of fibroblast growth factor-2. Circ Res. 2002 May 17; 90(9):966-73.

Mathias R A et al, Isolation of extracellular membranous vesicles for proteomic analysis.

Saadoun S et al, Intra-cerebral injection of neuromyelitis optica immunoglobulin G and human complement produces neuromyelitis optica lesions in mice. Brain. 2010 February; 133(Pt 2):349-61.

Saini H et al, Passively transferred human NMO-IgG exacerbates demyelination in mouse experimental autoimmune encephalomyelitis. BMC Neurol. 2013 Aug. 8; 13:104.

Silva K A et al. Surgical methods for full-thickness skin grafts to induce alopecia areata in C3H/HeJ mice. Comp Med. 2013 October; 63(5):392-7.

Swaisgood C M et al. Development of a sarcoidosis murine lung granuloma model using *Mycobacterium* superoxide dismutase A peptide. Am J Respir Cell Mol Biol. 2011 February; 44(2):166-74.

Talaat R M et al. Therapeutic effect of dimethyl dimethoxy biphenyl dicarboxylate on collagen-induced arthritis in rats. Chin J Integr Med. 2014 Mar. 2. [Epub ahead of print]

Tradtrantip L et al, Enzymatic deglycosylation converts pathogenic neuromyelitis optica anti-aquaporin-4 immunoglobulin G into therapeutic antibody. Ann Neurol. 2013 January; 73(1):77-85.

Tradtrantip L et al, Potential therapeutic benefit of c1-esterase inhibitor in neuromyelitis optica evaluated in vitro and in an experimental rat model. PLoS One. 2014 Sep. 5; 9(9):e106824.

Wang Z et al. Corilagin attenuates aerosol bleomycin-induced experimental lung injury. Int J Mol Sci. 2014 May 30; 15(6):9762-79.

Wiekmeijer A S et al. Sustained Engraftment of Cryopreserved Human Bone Marrow CD34(+) Cells in Young Adult NSG Mice. Biores Open Access. 2014; 3(3):110-6.

Wrzos C et al, Early loss of oligodendrocytes in human and experimental neuromyelitis optica lesions. Acta Neuropathol. 2014 April; 127(4):523-38.

Yamamoto T et al. Animal model of sclerotic skin. I: Local injections of bleomycin induce sclerotic skin mimicking scleroderma. J Invest Dermatol 1999; 112:456-62.

Yamamoto T et al. Cellular and molecular mechanisms of bleomycin-induced murine scleroderma: current update and future perspective. Exp Dermatol 2005; 14:81-95.

What is claimed is:

1. A method of increasing CCL5 secretion from adherent stromal cells (ASC), said method comprising the step of incubating ASC from placental or adipose tissue in a three-dimensional (3D) culture in a cytokine-containing growth medium, wherein one or more cytokines have been added to said cytokine-containing growth medium, wherein:

said one or more cytokines comprise Tumor Necrosis Factor alpha (TNF-alpha), wherein the TNF-alpha is present at a concentration between 1-12 nanograms/milliliter, said 3D culture is performed in a bioreactor, and incubating said ASC in said cytokine-containing growth medium is commenced during exponential phase,
thereby increasing CCL5 secretion from ASC.

2. The method of claim 1, said method comprising the steps of: (a) incubating said ASC from placental or adipose tissue in a 3D culture in a first growth medium, wherein no pro-inflammatory cytokines have been added to said first growth medium; and (b) subsequently performing the step of incubating said ASC in said cytokine-containing growth medium.

3. The method of claim 1, further comprising the subsequent step of harvesting said ASC by removing said ASC from said 3D culture.

4. The method of claim 1, wherein said 3D culture comprises a synthetic adherent material.

5. The method of claim 1, wherein the step of incubating said ASC in said cytokine-containing growth medium comprises: (i) adding a bolus of said TNF-alpha to a medium in said bioreactor, thereby generating said cytokine-containing growth medium; and (ii) operably connecting said cytokine-containing growth medium with an external reservoir comprising an additional amount of said TNF-alpha.

6. The method of claim 1, wherein said cytokine-containing growth medium further comprises Interferon-Gamma (IFN-gamma).

7. The method of claim 6, wherein said IFN-gamma is present at a concentration between 1-12 nanograms/milliliter.

8. The method of claim 1, wherein said ASC originate from placenta tissue.

9. The method of claim 1, wherein said ASC originate from adipose tissue.

10. ASC produced by the method of claim 1.

11. A population of cells, wherein the majority of said population expresses, on a population level, each of CD10, CD29, CD38, and CD40.

12. A population of cells, wherein the majority of said population expresses, on a population level, each of CD10, CD29, HLA-DR, and CD74.

13. The population of cells of claim 11, wherein said population is at least 40% positive for at least one of a marker selected from: CD42a, CD45Ra, CD77, CD243, and CD275.

14. A pharmaceutical composition comprising the ASC of claim 10.

15. A bioreactor comprising the ASC of claim 10.

16. The population of cells of claim 11, wherein the majority of said population further expresses CD90.

17. A pharmaceutical composition comprising the population of cells of claim 11.

18. A bioreactor comprising the population of cells of claim 11.

19. The population of cells of claim 12, wherein the majority of said population further expresses CD90.

20. A pharmaceutical composition comprising the population of cells of claim 12.

21. A bioreactor comprising the population of cells of claim 12.

* * * * *